(12) United States Patent
Holvoet et al.

(10) Patent No.: US 10,704,097 B2
(45) Date of Patent: Jul. 7, 2020

(54) OXIDATIVE STRESS AND CARDIOVASCULAR DISEASE EVENTS

(71) Applicant: KATHOLIEKE UNIVERSITEIT LEUVEN, Leuven (BE)

(72) Inventors: Paul Holvoet, Kessel-Lo (BE); Stefan Janssens, Heverlee (BE); Peter Sinnaeve, Blanden (BE)

(73) Assignee: KATHOLIEKE UNIVERSITEIT LEUVEN, Leuven (BE)

( * ) Notice: Subject to any disclaimer, the term of this patent is extended or adjusted under 35 U.S.C. 154(b) by 0 days.

(21) Appl. No.: 15/248,381

(22) Filed: Aug. 26, 2016

(65) Prior Publication Data

US 2017/0016071 A1    Jan. 19, 2017

Related U.S. Application Data

(63) Continuation-in-part of application No. PCT/BE2015/000006, filed on Feb. 26, 2015.

(30) Foreign Application Priority Data

Feb. 27, 2014  (GB) .................................. 1403410.2
Jul. 22, 2014   (GB) .................................. 1412949.8
May 27, 2016  (GB) .................................. 1609373.4

(51) Int. Cl.
*C12Q 1/6883* (2018.01)

(52) U.S. Cl.
CPC ...... *C12Q 1/6883* (2013.01); *C12Q 2600/112* (2013.01); *C12Q 2600/158* (2013.01); *C12Q 2600/16* (2013.01)

(58) Field of Classification Search
None
See application file for complete search history.

(56) References Cited

U.S. PATENT DOCUMENTS

| | | |
|---|---|---|
| 5,800,992 A | 9/1998 | Fodor et al. |
| 6,020,135 A | 2/2000 | Levine et al. |
| 6,033,860 A | 3/2000 | Lockhart et al. |
| 6,040,138 A | 3/2000 | Lockhart et al. |
| 6,344,316 B1 | 2/2002 | Lockhart et al. |
| 7,031,845 B2 | 4/2006 | Scott et al. |
| 7,047,141 B2 | 5/2006 | Dorris et al. |
| 7,052,842 B2 | 5/2006 | Kawase et al. |
| 7,138,506 B2 | 11/2006 | Fagan |
| 7,189,509 B2 | 3/2007 | Shao et al. |
| 7,211,390 B2 | 5/2007 | Rothberg et al. |
| 7,221,785 B2 | 5/2007 | Curry et al. |
| 7,244,559 B2 | 7/2007 | Rothberg et al. |
| 7,264,929 B2 | 9/2007 | Rothberg et al. |
| 7,276,592 B2 | 10/2007 | Bergmann et al. |
| 7,302,348 B2 | 11/2007 | Ghosh et al. |
| 7,321,829 B2 | 1/2008 | Remacle et al. |
| 7,323,308 B2 | 1/2008 | Barts |
| 7,335,470 B2 | 2/2008 | Mohammed et al. |
| 7,335,762 B2 | 2/2008 | Rothberg et al. |
| 7,347,921 B2 | 3/2008 | Barth et al. |
| 7,348,181 B2 | 3/2008 | Walt et al. |
| 7,353,116 B2 | 4/2008 | Webb et al. |
| 7,371,516 B1 | 5/2008 | Burchard |
| 7,439,346 B2 | 10/2008 | Johnson et al. |
| 2007/0031841 A1* | 2/2007 | Liew .................... C12Q 1/6883 435/6.14 |

FOREIGN PATENT DOCUMENTS

| | | |
|---|---|---|
| EP | 2554679 A1 | 2/2013 |
| WO | 2007007177 A2 | 1/2007 |
| WO | 2010006414 A1 | 1/2010 |
| WO | 2010129919 A1 | 11/2010 |
| WO | 2010133970 A1 | 11/2010 |
| WO | 2011020906 A2 | 2/2011 |

OTHER PUBLICATIONS

Ulrich (Human Muation (2002), pp. 1-8).*
Cheung et al (Nature Genetics, 2003, vol. 33, pp. 422-425).*
Benner et al (Trends in Genetics (2001) vol. 17, pp. 414-418).*
Cao et al ( BMC Genomics(2004) vol. 5, pp. 1-10).*
Garrido (Cell Death and Differentiation (2006) vol. 13, pp. 1423-1433).*
Stiburek (Molecular Biology of the Cell (volue 23, pp. 1010-1023).*
Whitworth (JACC (1986) vol. 8, pp. 1271-1276).*
Saito-Hisaminato et al. (DNA research (2002) vol. 9, pp. 35-45).*
Mierer (Heart (2008) vol. 95, pp. 900-908).*
Cai ( European J Biochem (1996) vol. 241, pp. 83-92).*
Alberti et al. "Harmonizing the Metabolic Syndrome: a Joint Interim Statement of the International Diabetes Federation Task Force on Epidemiology and Prevention; National Heart, Lung, and Blood Institute; American Heart Association; World Heart Federation; International Atherosclerosis Society; and International Association for the Study of Obesity", Oct. 20, 2009, Circulation vol. 120, pp. 1640-1645.
Bartel, "MicroRNAs: Genomics, Biogenesis, Mechanism, and Function," Cell, Jan. 23, 2004 vol. 116, pp. 281-297.
Bonauer et al., "Vascular microRNAs.", Current Drug Targets, vol. 11, No. 8, 2010, pp. 943-949.
Cooper et al., "A Comparison of the PROCAM and Framingham Point-Scoring Systems for Estimation of Individual Risk of Coronary Heart Disease in the Second Northwick Park Heart Study", 2005, Atherosclerosis, vol. 181, pp. 93-100.

(Continued)

*Primary Examiner* — Steven Pohnert
(74) *Attorney, Agent, or Firm* — Workman Nydegger

(57) ABSTRACT

The present invention relates to diagnosis and/or prognosis of cardiovascular disease and cardiovascular events. A prognostic risk score in relation to the cardiovascular events, more particular after intervention, can be determined by counting the number of deregulated genes (or derived proteins) in their isolated monocytes. Deregulation means low expression of COX1 and/or COX4I1, and/or TFAM, and/or RUNX2.

11 Claims, 6 Drawing Sheets

Specification includes a Sequence Listing.

(56) References Cited

OTHER PUBLICATIONS

Duncan et al., "Low-grade Systemic Inflammation and the Development of Type 2 Diabetes: the Atherosclerosis Risk in Communities Study", Diabetes, Jul. 2003, vol. 52, pp. 1799-1805.
Ford et al., "Prevalence of the Metabolic Syndrome Among US Adults: Findings From the Third National Health and Nutrition Examination Survey." JAMA, vol. 287, No. 3, pp. 356-359, Jan. 16, 2002.
Ford Earl S., "Trends in Predicted 10-year Risk of Coronary Heart Disease and Cardiovascular Disease Among U.S. adults from 1999 to 2010," Journal of the American College of Cardiology, vol. 61, No. 22, 2013, pp. 2249-2252.
Grundy et al., "Definition of Metabolic Syndrome: Report of the National Heart, Lung, and Blood Institute/American Heart Association Conference on Scientific Issues Related to Definition." Circulation, NHLBI/AHA Conference Proceedings, vol. 109, Jan. 27, 2004, e13-e18, pp. 433-438.
Garnier et al. "Depressed Mitochondrial Transcription Factors and Oxidative Capacity in Rat Failing Cardiac and Skeletal Muscles," J Physiol., vol. 551, No. 2, 2003, pp. 491-501.
Grundy, "Obesity, Metabolic Syndrome, and Cardiovascular Disease," The Journal of Clinical Endocrinology and Metabolism, vol. 89, No. 6, Jun. 2004, pp. 2595-2600.
Heneghan et al., "Role of microRNAs in Obesity and the Metabolic Syndrome",Obesity Reviews, Journal Compilation International Association for the Study of Obesity, vol. 11, 2009, pp. 354-361.
Holvoet et al., "Circulating Oxidized LDL is a Useful Marker for Identifying Patients with Coronary Artery Disease," Arterioscler Thromb Vasc Biol, Journal of the American Heart Association, vol. 21, May 2001, pp. 844-848.
Holvoet et al., "The Metabolic Syndrome, Circulating Oxidized LDL, and Risk of Myocardial Infarction in Well-Functioning Elderly People in the Health, Aging, and Body Composition Cohort," Diabetes, vol. 53, Apr. 2004, pp. 1068-1073.
Holvoet et al. "Association of High Coronary Heart Disease Risk Status with Circulating Oxidized LDL in the Well-Functioning Elderly: Findings From the Health, Aging, and Body Composition Study", Arterioscler Thromb Vasc Biol, Journal of the American Heart Association, vol. 23, Aug. 2003, pp. 1444-1448.
Holvoet et al., "Association Between Circulating Oxidized Low-Density Lipoprotein and Incidence of the Metabolic Syndrome," JAMA, vol. 299, May 21, 2008, pp. 2287-2293.
Iliopoulos et al., "STAT3 Activation of miR-21 and miR-181b-1 via PTEN and CYLD are Part of the Epigenetic Switch Linking Inflammation to Cancer", Mol Cell, vol. 39, No. 4, Aug. 27, 2010, pp. 493-506.
Ling C et al., "Epigenetics: A Molecular Link Between Environmental Factors and Type 2 Diabetes," Diabetes, vol. 58, Dec. 2009, pp. 2718-2725.
Moon et al., "Reactive Oxygen Species Mediates Disialoganglioside GD3-induced Inhibition of ERK1/2 and Matrix Metalloproteinase-9 Expression in Vascular Smooth Muscle Cells," The FASEB Journal, vol. 20, Jul. 2006, pp. 1387-1395.
Muntner et al., "Prevalence of Non-Traditional Cardiovascular Disease Risk Factors Among Persons with Impaired Fasting Glucose, Impaired Glucose Tolerance, Diabetes, and the Metabolic Syndrome: Analysis of the Third National Health and Nutrition Examination Survey (NHANES III)," AEP, vol. 14, No. 9, Oct. 2004, pp. 686-695.
International Search Report from PCT Application No. PCT/BE2015/000006, dated Jul. 6, 2015.
Racay et al. "Ischemia-Reperfusion Induces Inhibition of Mitochondrial Protein Synthesis and Cytochrome c Oxidase Activity in Rat Hippocampus," Physiologial Research, vol. 58, 2009, pp. 127-138.
Ridker et al., "C-Reactive Protein, the Metabolic Syndrome, and Risk of Incident Cardiovascular Events: An 8-Year Follow-Up of 14 719 Initially Healthy American Women", Circulation, vol. 107, Jan. 28, 2003, pp. 391-397.
Ridker et al., "Plasma Concentration of Interleukin-6 and the Risk of Future Myocardial Infarction Among Apparently Healthy Men", Circulation, vol. 101, Apr. 18, 2000, pp. 1767-1772.
Sposito et al. "Most of the Patients Presenting Myocardial Infarction Would Not be Eligible for Intensive Lipid-Lowering Based on Clinical Algorithms or Plasma C-Reactive Protein," Atherosclerosis, vol. 214, 2011, pp. 148-150.
European Office Action from EP Application No. 15723114.3, dated Aug. 22, 2017.

* cited by examiner

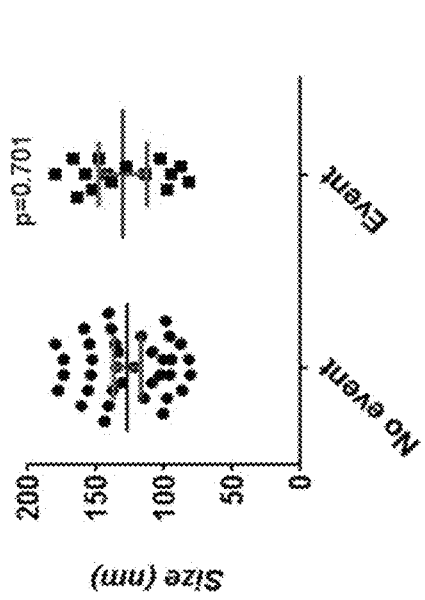
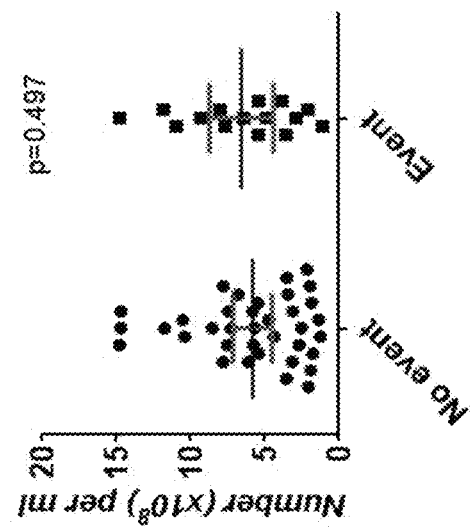
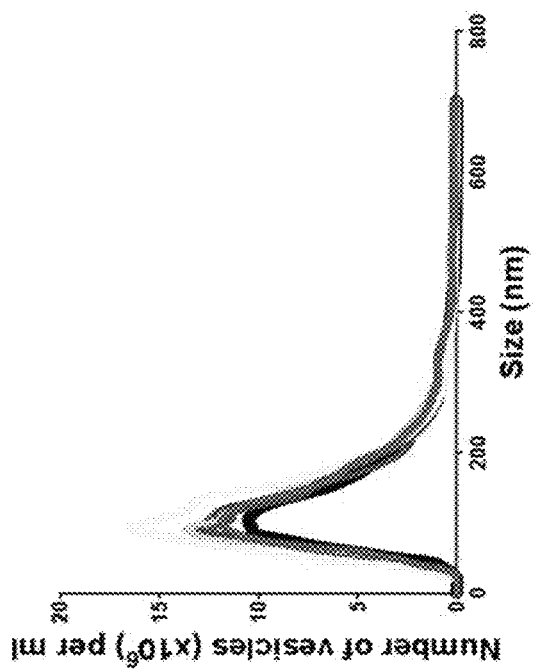
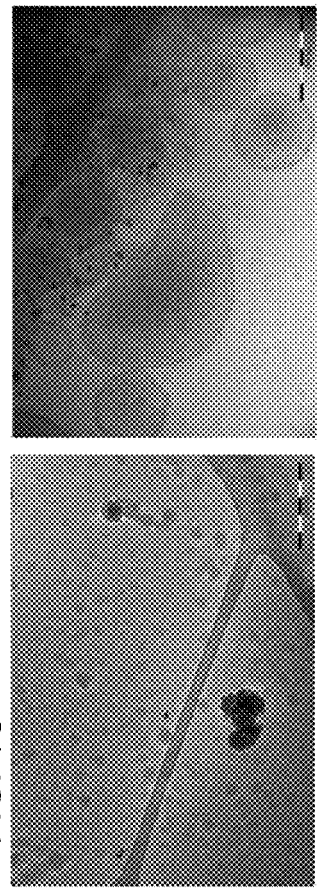
FIG. 1A
FIG. 1B
FIG. 1C
FIG. 1D

OXIDATIVE STRESS AND CARDIOVASCULAR DISEASE EVENTS

BACKGROUND OF THE INVENTION

Field of the Invention

The present invention relates generally to a new cluster of molecules in white blood cells, particularly monocytes that affect the oxidative stress and resistance to oxidation in association with the occurrence of cardiovascular diseases and the predisposition to new cardiovascular events.

Several documents are cited throughout the text of this specification. Each of the documents herein (including any manufacturer's specifications, instructions etc.) are hereby incorporated by reference. However, there is no admission that any document cited is indeed prior art of the present invention.

REFERENCE TO SEQUENCE LISTING SUBMITTED VIA EFS-WEB

This application includes an electronically submitted sequence listing in .txt format. The .txt file contains a sequence listing entitled "19893-19-Sequence_Listing.txt" created on Aug. 26, 2016 and is 33 kilobytes in size. The sequence listing contained in this .txt file is part of the specification and is hereby incorporated by reference herein in its entirety.

DESCRIPTION OF THE RELATED ART

Several risk-predicting algorithms such as the Framingham risk score (FRS) (1) and the PROCAM risk score (2) have been and are used to estimate the risk of cardiovascular diseases in a person without previously diagnosed disease. Risk factors in FRS are male gender, age, smoking, high blood pressure, high LDL-cholesterol, low HDL-cholesterol. T2DM patients are considered to be at high risk independent of their other risk factors. Risk factors in PROCAM are the same (for some with adjusted cut-off values, but high triglycerides are added. In addition, several risk factors particularly associated with obesity have been clustered in the metabolic syndrome (MetS), defined by the presence of at least three out of five symptoms or risk factors (i.e., central obesity, high blood pressure, elevated blood cholesterol/low HDL levels, elevated triglyceride levels, and insulin resistance) (3, 4). Persons having MetS are at risk of developing type 2 diabetes (T2DM) and cardiovascular diseases (5, 6). But given the difference in prevalence of several triads of MetS components, and the differences in risk associated with those different triads, the sole presence of MetS cannot predict an individual person's risk of developing cardiovascular diseases. Lately, emerging risk factors such as inflammation molecules like high-sensitivity C-reactive protein (hs-CRP) and interleukin-6 (IL-6), adipocytokines like adiponectin, and systemic markers of oxidative stress like oxidized LDL (ox-LDL) have been added to those algorithms and/or syndromes. However, a recent study showed that most of the patients presenting myocardial infarction would not be eligible for intensive therapy based on risk-predicting algorithms and plasma hs-CRP. (7). In agreement with these findings, our data show that the established risk factors included in the above mentioned algorithms and/or syndrome, together with the emerging risk factors do not allow to discriminate between patients who develop or don't develop new cardiovascular events, especially when patients are extensively treated by cholesterol lowering drugs like statins, and blood pressure and glucose lowering drugs. Indeed, our examples show that the age, gender, BMI, blood pressure, lipids, and levels of glucose and insulin, and the occurrence of MetS, and levels of hs-CRP, IL-6 and ox-LDL did not differ between patients who developed or did not develop new cardiovascular events. Therefore, there is need of new biomarkers to identify high-risk patients despite extensive treatment that results in lowering established and emerging risk factors. At best, these biomarkers should be causally involved in the development of cardiovascular diseases.

One disease process of crucial importance contributing to MetS and cardiovascular diseases is subclinical chronic low-grade inflammation (8). Population studies showed a strong correlation between pro-inflammatory biomarkers (such as hs-CRP, interleukin-6 (IL-6), and tumor necrosis factor-α (TNF-α)) and perturbations in glucose homeostasis, obesity, and atherosclerosis (9). In addition, increased inflammation (10, 11) and ox-LDL (12-15) were found to be associated with MetS and cardiovascular diseases. Inflammation and ox-LDL induce reactive oxygen species (ROS) which in turn induce the oxidation of proteins and lipids causing a vicious circle of persistent inflammation. Recent studies exploring the mechanisms linking ROS and inflammation found that ROS derived from mitochondria (mtROS) act as signal-transducing molecules that provoke endothelial dysfunction associated with uncoupling of nitric oxide synthase, induce the infiltration and activation of inflammatory cells, and increase apoptosis of endothelial and vascular smooth muscle cells contributing to plaque instability (16). Therefore, we identified molecules in monocytes and derived macrophages which regulate the formation of mtROS, in particular those which are related to the inflammatory toll-like receptor 2/NF-κB signaling pathway in the induction of pro-inflammatory cytokines and mtROS production in relation to insulin resistance, type 2 diabetes and atherosclerosis. Although mtROS were found to play an active role in several pathogenic mechanisms, there is still need for specific and sensitive assays to evaluate mitochondrial oxidative stress in relation to the occurrence of cardiovascular diseases and the development of new cardiovascular events. Our invention identifies RNA biomarkers which are associated with the presence of cardiovascular diseases and predict future cardiovascular events in patients. Our observations in obese diabetic mice showing the inverse relation between these markers and markers of instable plaques, such as high number of macrophages and high levels of ox-LDL, give mechanistic support to our finding that these markers are identifying unstable patients.

Candidate regulating molecules of above mentioned disease processes are microRNAs (miRs). They are highly conserved non-coding RNA molecules (about 22 nucleotides), which control gene expression either by inducing mRNA degradation or by blocking translation (17). Indeed, miRs have been associated with inflammation, oxidative stress, impaired adipogenesis and insulin signaling and apoptosis and angiogenesis in relation with obesity. All these processes contribute to the development of type 2 diabetes, atherosclerosis and associated cardiovascular disorders (18-20). A number of miRNAs of the present invention have previously been identified. For example, WO2010133970 discloses that miR-103 is upregulated in liver cells of obese mice and that inhibition of miR-103 leads to an improvement of several obesitas/insulin resistance parameters. Iliopoulos et al. (2010) disclosed that miR-181b-1 is pro-inflammatory in endothelial or cancer cells. They also show that miR-181b-1 directly inhibits expression of CYLD, which in its turn is known to inhibit NF-κB activity (21). WO2010129919 focuses on the influence of let-7 (including let-7a-let-7i) on asthma and lung inflammation. It shows that let-7a, and likely the other let-7 miRNAs, directly targets IL-13 expression. Furthermore, in vivo experiments show that inhibition of miR-155 (a let-7 family member) reduces inflammation in lungs.

Accordingly, a select panel of biomarkers which comprises RNAs and/or miRNAs associated with inflammation may be used to indicate whether a patient is at risk for experiencing (or having, suffering from, undergoing, progressing towards onset of, or developing) a cardiovascular event. The biomarkers may also be used to determine if the patient has a cardiovascular disorder (or disease), for example, coronary stenosis, and may be used to determine if a patient is responding to treatment for a cardiovascular disorder. Notably, the use of specific RNAs and/or miRNAs for predicting cardiovascular events is disclosed, as is the additive value of RNA and miRNA biomarkers. The biomarkers disclosed herein are molecules which regulate cellular and mitochondrial oxidative stress and inflammation.

DESCRIPTION OF THE DRAWINGS

The present invention will become more fully understood from the detailed description given herein below and the accompanying drawings which are given by way of illustration only and thus do not limit the present invention.

FIG. 1: Characterization of CD-14+ positive microvesicles isolated from plasma by MACS. FIG. 1A: representative distribution profiles of microvesicles isolated form plasma of patients; profiles were analyzed with Malvern Nanoparticle Tracking Analysis (NTA) system. FIG. 1B: cryo-TEM image of isolated microvesicles showing that most microvesicles had sizes ranging from 40 to 60 nm and some ranging in size from 100 to 200 nm; FIG. 1C: median size; FIG. 1D: number of microvesicles in plasma of controls and of CAD patients without and with new event.

FIG. 2: Expression of MT-COI and COX4I1 in microvesicles.

SUMMARY OF THE INVENTION

Figure 2A:
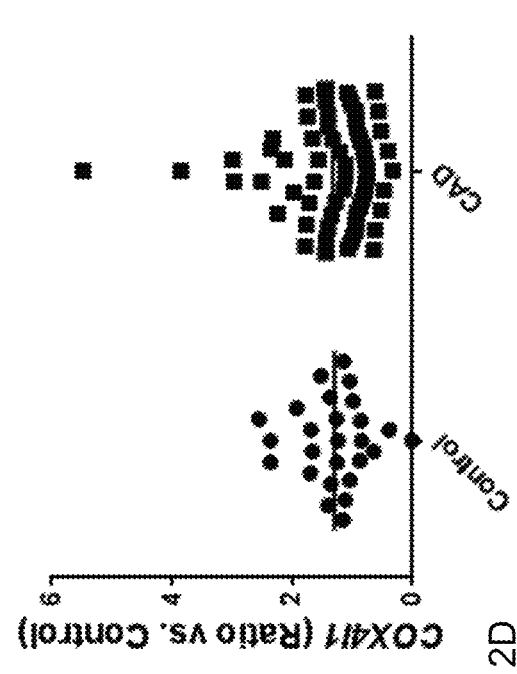
FIG. 2A: patients without CAD.
Figure 2B:
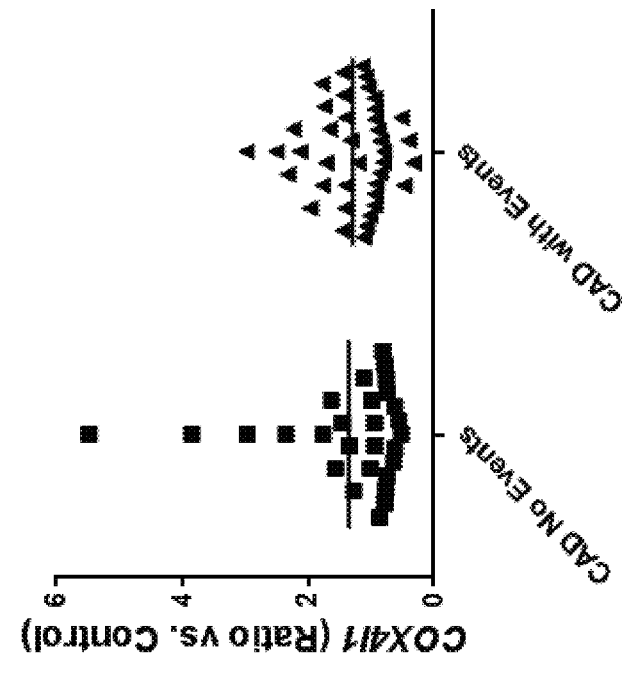
FIG. 2B: patients with CAD.
Figure 2C:
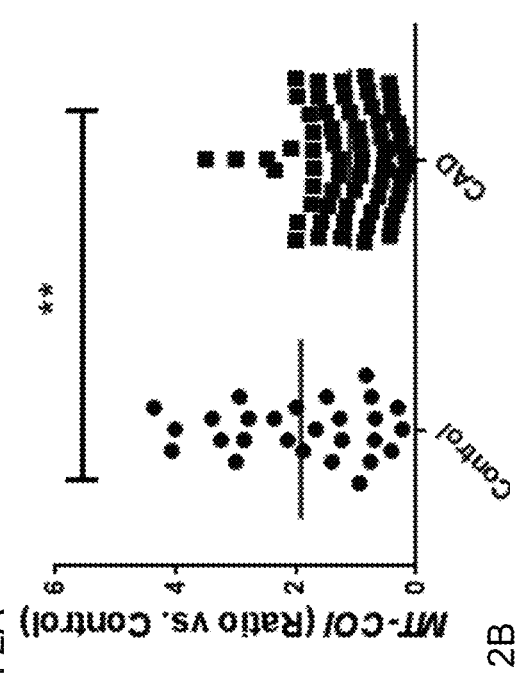
FIG. 2C: CAD patients without new event.
Figure 2D:
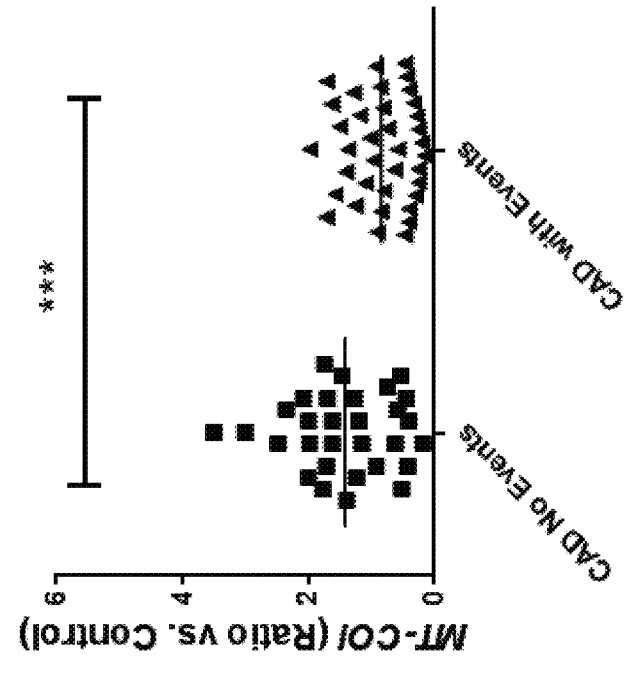
FIG. 2D: CAD patients with new event. RNA analysis of extracts of microvesicles was performed using TaqMan RNA assays. Quality control on the post-qPCR data was performed using qbase+. The results confirm that the experiment is performed according to our internal quality standards. Replicate variability falls within the set limit of 0.5 cycles for 94.27% of sample-target combinations. Expression was normalized to 5 reference genes: B2M (beta-2-microglobulin), PPIA (peptidylprolyl isomerase A), RPL13A (ribosomal protein L13a), RPS18 (ribosomal protein S18) and YWHAZ (tyrosine 3-monooxygenase/tryptophan 5-monooxygenase activation protein, zeta).

The present invention relates generally to a new cluster of molecules in white blood cells, particularly monocytes, which affects the oxidative stress and resistance to oxidation in association with the occurrence of cardiovascular diseases and the development of new cardiovascular events. This cluster of molecules is used to identify the optimal method or system for determining the risk of cardiovascular diseases associated with activated monocytes.

Accordingly, one aspect of the present disclosure is a method for identifying a patient at risk for experiencing one or more cardiovascular events, comprising: (a) obtaining a biological sample from the patient; (b) measuring expression of COX1 in the biological sample; and (c) comparing the expression of COX1 with reference measurements; wherein decreased expression of COX1 in the biological sample as compared to the reference measurements indicates that the patient is at risk for experiencing one or more cardiovascular events.

In some embodiments, the method further comprises measuring expression of COX4I1 in the biological sample in step (b), and comparing the expression of COX1 and COX4I1 with reference measurements, wherein reduced expression of COX1 and COX4I1 in the biological sample as compared to the reference measurements indicates that the patient is at risk for experiencing cardiovascular events. In certain embodiments, the method further comprises measuring expression of TFAM and RUNX2 in the biological sample in step (b), and comparing the expression of COX1, COX4I1, TFAM, and RUNX2 with reference measurements, wherein reduced expression of COX1, COX4I1, TFAM, and RUNX2 compared to the reference measurements indicates that the patient is at risk for experiencing cardiovascular events.

Yet another aspect of the present disclosure is a method for identifying a patient at risk for experiencing one or more cardiovascular events, comprising: (a) obtaining a biological sample from the patient; (b) measuring expression of COX1, COX4I1, TFAM, RUNX2, and miR-30b in the biological sample; and (c) comparing the expression of COX1, COX4I1, TFAM, RUNX2, and miR-30b with reference measurements; wherein decreased expression of COX1, COX4I1, TFAM, RUNX2, and miR-30b in the biological sample as compared to the reference measurements indicates that the patient is at risk for experiencing one or more cardiovascular events. In some embodiments, the method further comprises measuring expression of miR-26a in the biological sample in step (b); and (c) comparing the expression of COX1, COX4I1, TFAM, RUNX2, miR-30b, and miR-26a with reference measurements; wherein decreased expression of COX1, COX4I1, TFAM, RUNX2, miR-30b, and miR-26a in the biological sample as compared to the reference measurements indicates that the patient is at risk for experiencing one or more cardiovascular events.

In some embodiments, the method further comprises measuring expression of COX1 in the biological sample in step (b), and comparing the expression of miR-30b and COX1 with reference measurements, wherein reduced expression of miR-30b and COX1 in the biological sample as compared to the reference measurements indicates that the patient is at risk for experiencing cardiovascular events. In certain embodiments, the method further comprises measuring expression of COX4I1 in the biological sample in step (b), and comparing the expression of miR-30b and COX1 and COX4I1 with reference measurements, wherein reduced expression of miR-30b and COX1 and COX4I1 compared to the reference measurements indicates that the patient is at risk for experiencing cardiovascular events. In other embodiments, the method further comprises measuring expression of TFAM in the biological sample in step (b), and comparing the expression of miR-30b and COX1, COX4I1 and TFAM with reference measurements, wherein reduced expression of miR-30b and COX1, COX4I1 and TFAM compared to the reference measurements indicates that the patient is at risk for experiencing cardiovascular events. In other embodiments, the method further comprises measuring expression of COX1 in the biological sample in step (b), and comparing the expression of miR-30b and COX1 with reference measurements, wherein reduced expression of miR-26a and COX1 in the biological sample as compared to the reference measurements indicates that the patient is at risk for experiencing cardiovascular events. In certain embodiments, the method further comprises measuring expression of COX4I1 in the biological sample in step (b), and comparing the expression of miR-26a and COX1 and COX4I1 with reference measurements, wherein reduced expression of miR-26a and COX1 and COX4I1 compared to the reference measurements indicates that the patient is at risk for experiencing cardiovascular events. In other embodiments, the method further comprises measuring expression of TFAM in the biological sample in step (b), and comparing the expression of miR-26a and COX1, COX4I1 and TFAM with reference measurements, wherein reduced expression of miR-26a and COX1, COX4I1 and TFAM compared to the reference measurements indicates that the patient is at risk for experiencing cardiovascular events.

In some embodiments, the patient has at least one risk factor for cardiovascular disease. For example, the patient may have risk factors for cardiovascular disease are selected from advanced age, history of smoking, elevated LDL, decreased HDL, elevated triglycerides, elevated blood glucose, type 2 diabetes, metabolic syndrome, elevated blood pressure, obesity, elevated inflammation (characterized by high hs-CRP, IL-6, or low IL-10 and adiponectin), and elevated oxidized stress (characterized by high ROS or oxidized LDL).

In certain embodiments, the patient has a coronary stenosis. The patient may be at risk for developing a coronary stenosis, whether the patient was previously diagnosed with a stenosis or not.

In some embodiments, the patient has previously experienced one or more cardiovascular events. In certain embodiments, the patient has not previously experienced a cardiovascular event. The cardiovascular event may be selected from cardiovascular death, myocardial infarction, stroke or transient ischemic attack, recurrent ischemia requiring PCI, recurrent angina requiring PCI, coronary bypass surgery, and surgery or stenting of coronary or peripheral arteries, or development of heart failure.

In some embodiments, the one or more cardiovascular events occur within 3 years of identifying the patient at risk. For example, the cardiovascular event may occur within 1 year of identifying the patient at risk.

In certain embodiments, the biological sample is a blood sample. The blood sample may comprise monocytes. In some embodiments, the blood sample comprises microvesicles, for example exosomes. In some embodiments, expression comprises gene expression, for example, RNA expression. In other embodiments, the biological sample is a coronary artery aspirate or tissue or a vascular tissue sample.

DETAILED DESCRIPTION OF THE INVENTION

One aspect of the present disclosure relates to the identification of patients who have suffered from cardiovascular disease and/or patients who will experience cardiovascular events in the future. The identification methods are based on detection, measurement, and comparison to reference measurements of molecules which are related to oxidative stress and cellular resistance to oxidation. In particular, expression of these molecules may be associated with activated monocytes. Thus, patients who will develop cardiovascular events may show alterations in expression of these molecules, for example elevated or reduced levels of these molecules in monocytes as compared to control patients.

A. Definitions

Unless defined otherwise, technical and scientific terms used herein have the same meaning as commonly understood by one of ordinary skill in the art to which this invention belongs. Singleton et al., Dictionary of Microbiology and Molecular Biology 2nd ed., J. Wiley & Sons (New York, N.Y. 1994), Microarrays in Clinical Diagnostics (© 2005 Humana Press Inc.) provide one skilled in the art with a general guide to many of the terms used in the present application.

For purposes of the present invention, the following terms are defined below.

Myeloid refers to the non-lymphocytic groups of white blood cells, including the granulocytes, monocots and platelets.

Activated monocytes are monocytes that are associated with increased inflammation, often due to activation of the toll-like receptor (TLR)-2 (and/or -4), a decrease in the interleukin-1 receptor-associated kinase (IRAK)-3 (sometimes called IRAKM) and an increase in NFκB activity (22, 23), and/or an increased production of reactive oxygen species (ROS) and oxidative stress, often due to loss of antioxidant enzymes like superoxide dismutase (SOD1 or SOD3), and or gain of SOD2 (15, 24), and/or a loss of insulin signaling and IR, for example by loss of expression of the insulin receptor substrate (IRS)-1 and -2 (25). Activation of monocytes renders them more prone to infiltration in tissues (e.g. adipose, brain, vascular, pancreas, liver) often due to increased expression of the monocyte chemotactic protein 1 (MCP1 or otherwise called chemokine CC motif ligand or CCL2) (26). Once infiltrated, these activated monocytes are more prone to give rise to inflammatory and cytotoxic M1 macrophages instead of anti-inflammatory and cytoprotective M2 macrophages (27-30). In addition, they lose their capacity to activate their anti-inflammatory (e.g. increase in IRAK3) and antioxidant (e.g. increase in antioxidant SOD1 and/or SOD3 and decrease in SOD2 and ROS) mechanisms, and thus their capacity to switch their polarization from M1 to M2 in response to adiponectin (31, 32).

Arteriosclerosis, also called hardening of the arteries, is characterized by abnormal thickening and hardening of the walls of arteries, with a resulting loss of elasticity. The major form of arteriosclerosis is atherosclerosis, in which plaques consisting of macrophages, fatty deposits in foam cells, or atheromas, form on the inner walls of the arteries. These fatty deposits are largely due to the uptake of oxidized LDL by macrophages. In addition to fatty deposits, deposition of fat, cholesterol, calcium, and other substances in the arterial wall contributes to plaque growth. Moreover, deposition of tough, rigid collagen inside the vessel wall and around the atheroma increases the stiffness of the artery wall. Atherosclerosis causes three main problems. First, the atheromatous plaques, though long accommodated by artery enlargement ('remodeling'), eventually lead to stenosis (narrowing) of the artery and, therefore, an insufficient blood supply to the organ it feeds. If the compensating artery enlargement is excessive, a net aneurysm occurs. Finally, the accumulation of lipids renders the atherosclerotic plaques more prone to rupture, leading to thrombus formation resulting in myocardial infarction or stroke (see acute coronary syndromes below).

Arteriolosclerosis (hardening of small arteries, the arterioles) is the result of collagen deposition, but also muscle wall thickening and deposition of protein ("hyaline"). Calcification, sometimes even ossification (formation of complete bone tissue) occurs within the deepest and oldest layers of the sclerosed vessel wall.

Cardiovascular disease is any disease affecting the cardiovascular system, in addition to vascular disease such as those of the brain and kidney, and peripheral arterial disease. Cardiovascular disease frequently results from underlying conditions such as atherosclerosis and hypertension. Types of cardiovascular disease include but are not limited to coronary artery disease, cardiomyopathy, hypertensive heart disease, heart failure, and cardiac dysrhythmias, inflammatory heart disease (endocarditis, inflammatory cardiomegaly, myocarditis, valvular heart disease, cerebrovascular disease, stroke, peripheral arterial disease, congenital heart disease, and rheumatic heart disease.

Cardiovascular events refer to any incidents that may cause damage to the heart muscle. Examples of cardiovascular events include but are not limited to cardiovascular death, myocardial infarction, stroke or transient ischemic attack, recurrent ischemia requiring percutaneous coronary intervention (PCI), recurrent angina requiring PCI, coronary bypass surgery, and/or surgery or stenting of peripheral arteries, or development of heart failure, arrhythmias, heart valve disease, cardiomyopathy, thrombosis, carotid and/or coronary artery disease.

Coronary artery disease (CAD) also known as atherosclerotic heart disease, coronary heart disease, or ischemic heart disease (IHD), is the most common type of heart disease and cause of heart attacks. The disease is caused by plaque building up along the inner walls of the arteries of the heart, which narrows the arteries and reduces blood flow to the heart.

While the symptoms and signs of coronary artery disease are noted in the advanced state of disease, most individuals with coronary artery disease show no evidence of disease. For decades as the disease progresses subclinically before the first onset of symptoms, until often a "sudden" heart attack finally arises. Symptoms of stable ischemic heart disease include angina (characteristic chest pain on exertion) and decreased exercise tolerance. Unstable IHD presents itself as chest pain or other symptoms at rest, or rapidly worsening angina. The risk of artery narrowing increases with age, smoking, high blood cholesterol, diabetes, high blood pressure, and is more common in men and those who have close relatives with CAD.

IHD is conventionally diagnosed with the help of with:
Baseline electrocardiography (ECG)
Exercise ECG—Stress test
Exercise radioisotope test (nuclear stress test, myocardial scintigraphy)
Echocardiography (including stress echocardiography)
Coronary angiography
Intravascular imaging technology including intracoronary ultrasound, virtual histology and coronary optical coherence tomography
Magnetic resonance imaging (MRI)

Acute Coronary Syndrome

Diagnosis of acute coronary syndrome generally takes place in the emergency department, where ECGs may be performed sequentially to identify "evolving changes" (indicating ongoing damage to the heart muscle). Diagnosis is clear-cut if ECGs show elevation of the "ST segment", which in the context of severe typical chest pain is strongly indicative of an acute myocardial infarction (MI); this is termed a STEMI (ST-elevation MI), and is treated as an emergency with either urgent coronary angiography and percutaneous coronary intervention (angioplasty with or without stent insertion) or with thrombolysis ("clot buster" medication), whichever is available. In the absence of ST-segment elevation, heart damage (necrosis) is detected by cardiac markers (blood tests that identify heart muscle damage). If there is evidence of damage (i.e. infarction) in the absence of ST-segment elevation on the electrocardiogram, the chest pain is attributed to a "non-ST elevation MI" (NSTEMI). If there is no evidence of damage, the term "unstable angina" is used. This process usually necessitates admission to hospital, and close observation on a coronary care unit for possible complications (such as cardiac arrhythmias—irregularities in the heart rate).

Depending on the risk stratification, stress testing or angiography may be used to identify and treat coronary artery disease in patients who have had an NSTEMI or unstable angina.

Thrombogenicity refers to the tendency of a material in contact with the blood to produce a thrombus, or clot. It not only refers to fixed thrombi but also to emboli, thrombi which have become detached and travel through the bloodstream. Thrombogenicity can also encompass events such as the activation of immune pathways and the complement system. All materials are considered to be thrombogenic with the exception of the endothelial cells which line the vasculature. Certain medical implants appear non-thrombogenic due to high flow rates of blood past the implant, but in reality, all are thrombogenic to a degree.

Percutaneous coronary intervention (PCI) is performed to open blocked coronary arteries caused by coronary artery disease (CAD) and to restore arterial blood flow to the heart tissue without open-heart surgery. Percutaneous transluminal coronary angioplasty (PTCA) and stenting are examples of PCI.

Percutaneous transluminal coronary angioplasty (PTCA) is a technique in the treatment of atherosclerotic coronary heart disease and angina pectoris in which some plaques in the arteries of the heart are flattened against the arterial walls, resulting in improved circulation. The procedure involves threading a catheter through the vessel to the atherosclerotic plaque, inflating and deflating a small balloon at the tip of the catheter several times, and then removing the catheter. The procedure is performed under radiographic or ultrasonic visualization. When it is successful, the plaques remain compressed and the symptoms of heart disease, including the pain of angina, are decreased. The alternative to this treatment is coronary bypass surgery, which is more expensive and dangerous and requires longer hospitalization and rehabilitation.

When during PTCA a stent is placed into the body, the procedure is called stenting. There are different kinds of stents. Most are made of a metal or plastic mesh-like material. However, stent grafts are made of fabric. An intraluminal coronary artery stent is a small, self-expanding, metal mesh tube that is placed inside a coronary artery after balloon angioplasty to prevent the artery from re-closing. A drug-eluting stent is coated with a medicine that helps further prevent the arteries from re-closing. Like other coronary artery stents, it is left permanently in the artery.

An ischemic stroke is death of an area of brain tissue (cerebral infarction) resulting from an inadequate supply of blood and oxygen to the brain due to blockage of an artery. Ischemic stroke usually results when an artery to the brain is blocked, often by a blood clot or a fatty deposit due to atherosclerosis. Symptoms occur suddenly and may include muscle weakness, paralysis, lost or abnormal sensation on one side of the body, difficult speech, confusion, problems with vision, dizziness, and loss of balance and coordination. Diagnosis is usually based on symptoms and results of a physical examination, imaging tests, and blood tests. Treatment may include drugs to break up blood clots or to make blood less likely to clot, sometimes percutaneous intervention, followed by rehabilitation. About one third of people recover all or most of normal function after an ischemic stroke. Ischemic stroke occurs when local blood flow is suddenly limited by vessel occlusion. The rate of neuronal death varies with blood flow. If blood flow falls to less than 15 mL/100 g/min, energy failure and subsequent cell death occur within minutes. Even suboptimal flow for longer periods may cause the cells to die by an apoptotic mechanism over days to weeks. Rapid restoration of blood flow is essential to save brain tissue. The mechanism of stroke involving the PCA territory is variable. It is commonly due to embolization from the heart, the aortic arch, the vertebral artery, or the basilar artery. Other mechanisms include intrinsic atherosclerotic disease and vasospasm Glycemia concerns the presence of glucose in the blood. It is a medical term meaning that the blood glucose is elevated, typically above 100 mg/dl. Other terms are impaired glucose tolerance (IGT) or prediabetes.

Insulinemia concerns an abnormally large concentration of insulin in the blood.

Insulin resistance (IR) is the diminished ability of cells to respond to the action of insulin in transporting glucose (sugar) from the bloodstream into muscle and other tissues. IR typically develops with obesity and heralds the onset of T2DM. It is as if insulin is "knocking" on the door of muscle. The muscle hears the knock, opens up, and lets glucose in. But with IR, the muscle cannot hear the knocking of the insulin (the muscle is "resistant"). The pancreas makes more insulin, which increases insulin levels in the blood and causes a louder "knock." Eventually, the pancreas produces far more insulin than normal and the muscles continue to be resistant to the knock. As long as one can produce enough insulin to overcome this resistance, blood glucose levels remain normal. Once the pancreas is no longer able to keep up, blood glucose starts to rise, initially after meals, eventually even in the fasting state. IR is an early feature and finding in the pathogenesis of T2DM. IR is the condition in which normal amounts of insulin are inadequate to produce a normal insulin response from fat, muscle and liver cells. IR in fat cells reduces the effects of insulin and results in elevated hydrolysis of stored triglycerides in the absence of measures which either increase insulin sensitivity or which provide additional insulin. Increased mobilization of stored lipids in these cells elevates free fatty acids in the blood plasma. IR in muscle cells reduces glucose uptake (and so local storage of glucose as (glycogen), whereas IR in liver cells reduces storage of glycogen, making it unavailable for release of glucose into the blood when blood insulin levels fall (normally only when blood glucose levels are at low storage: Both lead to elevated blood glucose levels. High plasma levels of insulin and glucose due to IR often lead to metabolic syndrome and T2DM, including its complications. In 2000, there were approximately 171 million people, worldwide, with diabetes. The numbers of diabetes patients will expectedly more than double over the next 25 years, to reach a total of 366 million by 2030 (WHO/IDF, 2004). The two main contributors to the worldwide increase in prevalence of diabetes are population ageing and urbanization, especially in developing countries, with the consequent increase in the prevalence of obesity (WHO/IDF, 2004). Diet intervention and physical training to induce weight loss, PPARγ agonists and statins, and metformin are frequently used to improve insulin sensitivity (33, 34).

Diabetes, type 2 (T2DM) is one of the two major types of diabetes, the type in which the beta cells of the pancreas produce insulin but the body is unable to use it effectively because the cells of the body are resistant to the action of insulin. Although this type of diabetes may not carry the same risk of death from ketoacidosis, it otherwise involves many of the same risks of long-term complications as type 1 diabetes (in which there is a lack of insulin). The aim of treatment is to normalize the blood glucose in an attempt to prevent or minimize complications. People with T2DM may experience marked hyperglycemia, but most do not require insulin injections. In fact, 80% of all people with T2DM can be treated with diet, exercise, and, if needed be, oral hypoglycemic agents (drugs taken by mouth to lower the blood sugar, such as metformin). T2DM requires good dietary control including the restriction of calories, lowered consumption of simple carbohydrates and fat with increased consumption of complex carbohydrates and fiber. Regular aerobic exercise is also an important method for treating T2DM diabetes since it decreases IR and helps burn excessive glucose. Regular exercise also may help lower blood lipids and reduce some effects of stress, both important factors in treating diabetes and preventing complications. T2DM is also known as insulin-resistant diabetes, non-insulin dependent diabetes, and adult-onset diabetes.

Dyslipidemia (From dys-+lipid (fat)+-emia (in the blood) =essentially, disordered lipids in the blood) is a disorder of lipoprotein metabolism. Dyslipidemias may be manifested by elevation of the triglyceride concentrations, and a decrease in the "good" high-density lipoprotein (HDL) cholesterol concentration in the blood. Dyslipidemia comes under consideration in many situations including diabetes, a common cause of lipidemia. For adults with diabetes, it has been recommended that the levels HDL-cholesterol, and triglyceride be measured every year. Optimal HDL-cholesterol levels are equal to or greater than 40 mg/dL (1.02 mmol/L), and desirable triglyceride levels are less than 150 mg/dL (1.7 mmol/L). PPARα agonists are used to treat dyslipidemia (35).

HDL-cholesterol concerns lipoproteins, which are combinations of lipids (fats) and proteins, are the form in which lipids are transported in the blood. The high-density lipoproteins transport cholesterol from the tissues of the body to the liver so it can be eliminated (in the bile). HDL-cholesterol is therefore considered the "good" cholesterol. The higher the HDL-cholesterol level, the lower the risk of coronary artery disease. Even small increases in HDL-cholesterol reduce the frequency of heart attacks. For each 1 mg/dl increase in HDL-cholesterol there is a 2 to 4% reduction in the risk of coronary heart disease. Although there are no formal guidelines, proposed treatment goals for patients with low HDL-cholesterol are to increase HDL-cholesterol to above 35 mg/dl in men and 45 mg/dl in women with a family history of coronary heart disease; and to increase HDL-cholesterol to approach 45 mg/dl in men and 55 mg/dl in women with known coronary heart disease. The first step in increasing HDL-cholesterol levels is life style modification. Regular aerobic exercise, loss of excess weight (fat), and cessation of cigarette smoking cigarettes will increase HDL-cholesterol levels. Moderate alcohol consumption (such as one drink a day) also raises HDL-cholesterol. When life style modifications are insufficient, medications are used. Medications that are effective in increasing HDL-cholesterol include nicotinic acid (niacin), fibrates, estrogen, and to a lesser extent, the statin drugs. But some of these (e.g. niacin) have not been proven to improve outcome. Newer drugs including the CETP inhibitors increase HDL but have so far failed to demonstrate a benefit in preventing CV events, and appear to have undesirable side effects as well.

Triglycerides are the major form of fat. A triglyceride consists of three molecules of fatty acid combined with a molecule of the alcohol glycerol. Triglycerides serve as the backbone of many types of lipids (fats). Triglycerides come from the food we eat as well as from being produced by the body. Triglyceride levels are influenced by recent fat and alcohol intake, and should be measured after fasting for at least 12 hours. A period of abstinence from alcohol is advised before testing for triglycerides. Markedly high triglyceride levels (greater than 500 mg/dl) can cause inflammation of the pancreas (pancreatitis). Therefore, these high levels should be treated aggressively with low fat diets and medications, if needed.

Hypercholesterolemia is manifested by elevation of the total cholesterol due to elevation of the "bad" low-density lipoprotein (LDL) cholesterol in the blood. Optimal LDL-cholesterol levels for adults with diabetes are less than 100 mg/dL (2.60 mmol/L), and 70 mg/dL in secondary prevention.

Low-density lipoprotein (LDL) belongs to the lipoprotein particle family. Its size is approx. 22 nm and its mass is about 3 million Daltons; but, since LDL particles contain a changing number of fatty acids, they actually have a mass and size distribution. Each native LDL particle contains a single apolipoprotein B-100 molecule (Apo B-100, a protein with 4536 amino acid residues) that circles the fatty acids, keeping them soluble in the aqueous environment. In addition, LDL has a highly-hydrophobic core consisting of polyunsaturated fatty acid known as linoleate and about 1500 esterified cholesterol molecules. This core is surrounded by a shell of phospholipids and unesterified cholesterol as well as a single copy of B-100 large protein (514 kD). Cholesterol is an animal sterol that is normally synthesized by the liver. The main types, low-density lipoprotein (LDL) and high-density lipoprotein (HDL) carry cholesterol from and to the liver, respectively. LDL-cholesterol concerns thus the cholesterol in low-density lipoproteins. Cholesterol is required in the membrane of mammalian cells for normal cellular function, and is either synthesized in the endoplasmic reticulum, or derived from the diet, in which case it is delivered by the bloodstream in low-density lipoproteins. These are taken into the cell by LDL receptor-mediated endocytosis in clathrin-coated pits, and then hydrolyzed in lysosomes. Ox-LDL-cholesterol concerns a LDL-cholesterol that has been bombarded by free radicals; it is thought to cause atherosclerosis; the 'bad' cholesterol; a high level in the blood is thought to be related to various pathogenic conditions.

Hypertension or High blood pressure is defined as a repeatedly elevated blood pressure exceeding 140 over 90 mmHg—a systolic pressure above 140 with a diastolic pressure above 90. Chronic hypertension is a "silent" condition. Stealthy as a cat, it can cause blood vessel changes in the back of the eye (retina), abnormal thickening of the heart muscle, kidney failure, and brain damage. For diagnosis, there is no substitute for measurement of blood pressure. Not having your blood pressure checked (or checking it yourself) is an invitation to hypertension. No specific cause for hypertension is found in 95% of cases. Hypertension is treated with regular aerobic exercise, weight reduction (if overweight), salt restriction, and medications.

Metabolic syndrome (MetS) is a combination of medical disorders that increase the risk of developing cardiovascular disease and T2DM. It affects a large number of people, and prevalence increases with age. Some studies estimate the prevalence in the USA to be up to 25% of the population. MetS is also known as metabolic syndrome X, syndrome X, IR syndrome, Reaven's syndrome or CHAOS. MetS components were defined as detailed in the Third Report of the National Cholesterol Education Program Expert Panel on Detection, Evaluation, and Treatment of High Blood Cholesterol in adults (ATPIII) report: 1) waist circumference≥102 cm in men and ≥88 cm in women; 2) fasting triglycerides≥150 mg/dl (1.70 mmol/l); 3) HDL-cholesterol<40 mg/dl (1.03 mmol/l) in men and <50 mg/dl (1.29 mmol/l) in women; 4) blood pressure≥130/85 mmHg or on anti-hypertensive medication; 5) fasting-glucose≥100 mg/dl (5.55 mmol/l) or on anti-diabetic medication (3). Recently, hs-CRP has been defined as an independent risk factor of T2DM and cardiovascular diseases. Persons with hs-CRP blood values of at least 3 mg/L are at higher risk. Therefore, persons with the MetS disorder phenotype are persons with at least three components out of six components.

The inflammatory state of a cell can be measured by determining well-known inflammatory parameters associated with said cell. These parameters include certain chemokines and cytokines, including but not limited to IFN-γ, IL-1, IL-6, IL-8, and TNF-α. An increased inflammatory state of a cell refers to an increased amount of inflammatory parameters associated with said cell compared to a control cell. Similarly, a normal or decreased inflammatory state of a cell refers to a similar or decreased amount, respectively, of inflammatory parameters associated with said cell compared to a control cell.

Similarly, the oxidative stress state of a cell can be measured by determining well-known oxidative stress parameters, such as e.g. the amount of reactive oxygen species (ROS). An increased, normal or decreased oxidative stress state of a cell refers, respectively, to an increased, similar or decreased amount of oxidative stress parameters associated with said cell compared to a control cell.

"Sample" or "biological sample" as used herein can be any organ, tissue, cell, or cell extract isolated from a subject, a cell-derived vesicle, such as a sample isolated from a mammal having a metabolic syndrome disorder or at risk for a metabolic syndrome disorder (e.g., based on family history or personal history). For example, a sample can include, without limitation, cells or tissue (e.g., from a biopsy or autopsy), peripheral blood, whole blood, red cell concentrates, platelet concentrates, leukocyte concentrates, blood cell proteins, blood plasma, platelet-rich plasma, a plasma concentrate, a precipitate from any fractionation of the plasma, a supernatant from any fractionation of the plasma, blood plasma protein fractions, purified or partially purified blood proteins or other components, serum, tissue or fine needle biopsy samples, or any other specimen, or any extract thereof, obtained from a patient (human or animal), test subject, healthy volunteer, or experimental animal. A subject can be a human, rat, mouse, non-human primate, etc. A sample may also include sections of tissues such as frozen sections taken for histological purposes. A "sample" may also be a cell or cell line created under experimental conditions, that is not directly isolated from a subject.

In a particular embodiment the sample is selected from the group consisting of (a) a liquid containing cells; (b) a tissue-sample; (c) a cell-sample; (d) a cell-derived vesicle; (e) a cell biopsy; more in particular the sample comprises hematopoietic cells or blood cells; even more in particular the sample comprises at least one myeloid cell or debris thereof. In an even further embodiment the sample comprises at least one of monocytes or peripheral blood mononuclear cells or debris thereof.

In addition, a sample can also be a blood-derived sample, like plasma or serum. In another particular embodiment, the RNAs of the present invention can be quantified or qualified on isolated microvesicles (MVs), particularly on monocyte-derived MVs. They bear surface receptors/ligands of the original cells and have the potential to selectively interact with specific target cells. They are involved in cell-to-cell communication including the communication between adipocytes and macrophages and between circulating monocytes and vascular endothelial cells. Due to the presence of specific surface receptors/ligands, peripheral blood MVs can be divided in origin-based subpopulations which can be used to determine (mi)RNA expression profiles in MVs derived from one specific cell type. In detail, peripheral blood MVs derived from mononuclear phagocyte cell lineage can be detected with anti-CD14, anti-CD16, anti-CD206, anti-CCR2, anti-CCR3 and anti-CCR5 antibodies. By labeling the antibodies with a fluorescent group or magnetic particles, these cell-specific MVs can be isolated using FACS or magnetic cell separation technology. In the MV various names have been used, including particles, microparticles, vesicles, MVs, nanovesicles, exosomes, dexosomes, argosomes, ectosomes, etc. Exosomes are considered to be small (30-100 nm in diameter) membranous vesicles which are formed by the inward budding of multivesicular bodies (MVBs) and are released from the cell into the microenvironment following the fusion of MVBs with the plasma membrane. Inward budding of endosomal membranes results in the progressive accumulation of intraluminal vesicles (ILVs) within large MVBs. Transmembrane proteins are incorporated into the invaginating membrane while the cytosolic components are engulfed within the ILVs. In practice, most human studies have examined mixed populations containing both exosomes and shedding microvesicles (also called ectosomes or microparticles); only a few studies have rigorously distinguished between the two. Accordingly, exosomes and shedding microvesicles are collectively called microvesicles in this application, as agreed on by our peers (36)

A "control" or "reference" includes a sample obtained for use in determining base-line expression or activity. Accordingly, a control sample may be obtained by a number of means or from a defined patient population, such as subjects do not have a coronary stenosis, or patients who have not experienced a cardiovascular event; or from cells or cell lines derived from such subjects. A control also includes a previously established standard, such as a previously characterized pool of RNA or protein extracts from monocytes of at least 20 subjects who do not have a coronary stenosis, or any of the other diseases as described herein. Accordingly, any test or assay conducted according to the invention may be compared with the established standard and it may not be necessary to obtain a control sample for comparison each time, allowing to comparing changes with time in the same individual with the same standard.

The term "array" or "microarray" in general refers to an ordered arrangement of hybridizable array elements such as polynucleotide probes on a substrate. An "array" is typically a spatially or logically organized collection, e.g., of oligonucleotide sequences or nucleotide sequence products such as RNA or proteins encoded by an oligonucleotide sequence. In some embodiments, an array includes antibodies or other binding reagents specific for products of a candidate library. The array element may be an oligonucleotide, DNA fragment, polynucleotide, or the like, as defined below. The array element may include any element immobilized on a solid support that is capable of binding with specificity to a target sequence such that gene expression may be determined, either qualitatively or quantitatively.

When referring to a pattern of expression, a "qualitative" difference in gene expression refers to a difference that is not assigned a relative value. That is, such a difference is designated by an "all or nothing" valuation. Such an all or nothing variation can be, for example, expression above or below a threshold of detection (an on/off pattern of expression). Alternatively, a qualitative difference can refer to expression of different types of expression products, e.g., different alleles (e.g., a mutant or polymorphic allele), variants (including sequence variants as well as post-translationally modified variants), etc. In contrast, a "quantitative" difference, when referring to a pattern of gene expression, refers to a difference in expression that can be assigned a value on a graduated scale, (e.g., a 0-5 or 1-10 scale, a ++++ scale, a grade 1 grade 5 scale, or the like; it will be understood that the numbers selected for illustration are entirely arbitrary and in no-way are meant to be interpreted to limit the invention). Microarrays are useful in carrying out the methods disclosed herein because of the reproducibility between different experiments. DNA microarrays provide one method for the simultaneous measurement of the expression levels of large numbers of genes. Each array consists of a reproducible pattern of capture probes attached to a solid support. Labeled RNA or DNA is hybridized to complementary probes on the array and then detected for instance by laser scanning. Hybridization intensities for each probe on the array are determined and converted to a quantitative value representing relative gene expression levels. See the patent publications Nos. U.S. Pat. Nos. 6,040,138, 5,800,992 and 6,020,135, 6,033,860, 6,344,316, 7,439,346, 7,371,516, 7,353,116, 7,348,181, 7,347,921, 7,335,762, 7,335,470, 7,323,308, 7,321,829, 7,302,348, 7,276,592, 7,264,929, 7,244,559, 7,221,785, 7,211,390, 7,189,509, 7,138,506, 7,052,842, 7,047,141 and 7,031,845 which are incorporated herein by reference. High-density oligonucleotide arrays are particularly useful for determining the gene expression profile for a large number of RNA's in a sample.

A "DNA fragment" includes polynucleotides and/or oligonucleotides and refers to a plurality of joined nucleotide units formed from naturally-occurring bases and cyclofuranosyl groups joined by native phosphodiester bonds. This term effectively refers to naturally-occurring species or synthetic species formed from naturally-occurring subunits. "DNA fragment" also refers to purine and pyrimidine groups and moieties which function similarly but which have no naturally-occurring portions. Thus, DNA fragments may have altered sugar moieties or inter-sugar linkages. Exemplary among these are the phosphorothioate and other sulfur containing species. They may also contain altered base units or other modifications, provided that biological activity is retained. DNA fragments may also include species that include at least some modified base forms. Thus, purines and pyrimidines other than those normally found in nature may be so employed. Similarly, modifications on the cyclofuranose portions of the nucleotide subunits may also occur as long as biological function is not eliminated by such modifications.

The term "polynucleotide," when used in singular or plural generally refers to any polyribonucleotide or polydeoxribonucleotide, which may be unmodified RNA or DNA or modified RNA or DNA. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. Thus, DNAs or RNAs with backbones modified for stability or for other reasons are "polynucleotides" as that term is intended herein. Moreover, DNAs or RNAs comprising unusual bases, such as inosine, or modified bases, such as tritiated bases, are included within the term "polynucleotides" as defined herein. In general, the term "polynucleotide" embraces all chemically, enzymatically and/or metabolically modified forms of unmodified polynucleotides, as well as the chemical forms of DNA and RNA characteristic of cells, including simple and complex cells.

The term "oligonucleotide" refers to a relatively short polynucleotide, including, without limitation, single-stranded deoxyribonucleotides, single- or double-stranded ribonucleotides, RNA: DNA hybrids and double-stranded DNAs. Oligonucleotides, such as single-stranded DNA oligonucleotides, are often synthesized by chemical methods, for example using automated oligonucleotide synthesizers that are commercially available. However, oligonucleotides can be made by a variety of other methods, including in vitro recombinant DNA-mediated techniques and by expression of DNAs in cells.

The terms "differentially expressed gene", "differential gene expression" and their synonyms, which are used interchangeably, refer to a gene whose expression is activated to a higher or lower level in a subject, relative to its expression in a normal or control subject, to a historical value in the same individual, and/or to a standard. A differentially expressed gene may be either activated or inhibited at the nucleic acid level or protein level, or may be subject to alternative splicing to result in a different polypeptide product. Such differences may be evidenced by a change in mRNA levels, surface expression, secretion or other partitioning of a polypeptide, for example. Differential gene expression may include a comparison of expression between two or more genes, or a comparison of the ratios of the expression between two or more genes, or even a comparison of two differently processed products of the same gene, which differ between normal subjects and subjects suffering from a disease, or between various stages of the same disease. Differential expression includes both quantitative, as well as qualitative, differences in the temporal or cellular expression pattern in a gene or its expression products. As used herein, "differential gene expression" can be present when there is, for example, at least an about a one to about two-fold, or about two to about four-fold, or about four to about six-fold, or about six to about eight-fold, or about eight to about ten-fold, or greater than about 11-fold difference between the expression of a given gene in a patient of interest compared to a suitable control. However, folds change less than one is not intended to be excluded and to the extent such change can be accurately measured, a fold change less than one may be reasonably relied upon in carrying out the methods disclosed herein.

In some embodiments, the fold change may be greater than about five or about 10 or about 20 or about 30 or about 40.

The phrase "gene expression profile" as used herein, is intended to encompass the general usage of the term as used in the art, and generally means the collective data representing gene expression with respect to a selected group of two or more genes, wherein the gene expression may be upregulated, downregulated, or unchanged as compared to a reference standard A gene expression profile is obtained via measurement of the expression level of many individual genes. The expression profiles can be prepared using different methods. Suitable methods for preparing a gene expression profile include, but are not limited to reverse transcription loop-mediated amplification (RT-LAMP), for instance one-step RT-LAMP, quantitative RT-PCR, Northern Blot, in situ hybridization, slot-blotting, nuclease protection assay, nucleic acid arrays, and immunoassays. The gene expression profile may also be determined indirectly via measurement of one or more gene products (whether a full or partial gene product) for a given gene sequence, where that gene product is known or determined to correlate with gene expression.

The phrase "gene product" is intended to have the meaning as generally understood in the art and is intended to generally encompass the product(s) of RNA translation resulting in a protein and/or a protein fragment. The gene products of the genes identified herein may also be used for the purposes of diagnosis or treatment in accordance with the methods described herein.

A "reference gene expression profile" as used herein, is intended to indicate the gene expression profile, as defined above, for a pre selected group which is useful for comparison to the gene expression profile of a subject of interest. For example, the reference gene expression profile may be the gene expression profile represented by a collection of RNA samples from "normal" or "control" individuals that has been processed as a single sample. "Normal" or control individuals mean individuals without metabolic disorder phenotype, T2DM, and coronary stenosis. The reference gene expression profile may also mean the profile in a historical sample obtained from the same individual before an intervention with a dietary, physical, pharmaceutical or any other intervention such as PTCA, stenting, PCI, or coronary bypass surgery. Alternatively, a standard cDNA containing gene-specific sequences can be used as the reference. The "reference gene expression profile" may vary and such variance will be readily appreciated by one of ordinary skill in the art.

The phrase "reference standard" as used herein may refer to the phrase "reference gene expression profile" or may more broadly encompass any suitable reference standard which may be used as a basis of comparison with respect to the measured variable. For example, a reference standard may be an internal control, the gene expression or a gene product of a "healthy" or "normal" subject, a housekeeping gene, or any unregulated gene or gene product. The phrase is intended to be generally non-limiting in that the choice of a reference standard is well within the level of skill in the art and is understood to vary based on the assay conditions and reagents available to one using the methods disclosed herein.

"Gene expression profiling" as used herein, refers to any method that can analyze the expression of selected genes in selected samples.

The phrase "gene expression system" as used herein, refers to any system, device or means to detect gene expression and includes diagnostic agents, candidate libraries, oligonucleotide sets or probe sets.

The terms "diagnostic oligonucleotide" or "diagnostic oligonucleotide set" generally refers to an oligonucleotide or to a set of two or more oligonucleotides that, when evaluated for differential expression their corresponding diagnostic genes, collectively yields predictive data.

Such predictive data typically relates to diagnosis, prognosis, selection of therapeutic agents, monitoring of therapeutic outcomes, and the like. In general, the components of a diagnostic oligonucleotide or a diagnostic oligonucleotide set are distinguished from oligonucleotide sequences that are evaluated by analysis of the DNA to directly determine the genotype of an individual as it correlates with a specified trait or phenotype, such as a disease, in that it is the pattern of expression of the components of the diagnostic oligonucleotide set, rather than mutation or polymorphism of the DNA sequence that provides predictive value. It will be understood that a particular component (or member) of a diagnostic oligonucleotide set can, in some cases, also present one or more mutations, or polymorphisms that are amenable to direct genotyping by any of a variety of well known analysis methods, e.g., Southern blotting, RFLP, AFLP, SSCP, SNP, and the like.

The phrase "gene amplification" refers to a process by which multiple copies of a gene or gene fragment are formed in a particular cell or cell line. The duplicated region (a stretch of amplified DNA) is often referred to as "amplicon." Usually, the amount of the messenger RNA (mRNA) produced, i.e., the level of gene expression, also increases in the proportion of the number of copies made of the particular gene expressed.

A "gene expression system" refers to any system, device or means to detect gene expression and includes diagnostic agents, candidate libraries oligonucleotide, diagnostic gene sets, oligonucleotide sets, array sets, or probe sets.

As used herein, a "gene probe" refers to the gene sequence arrayed on a substrate.

As used herein, a "nucleotide probe" refers to the oligonucleotide, DNA fragment, polynucleotide sequence arrayed on a substrate.

The terms "splicing" and "RNA splicing" are used interchangeably and refer to RNA processing that removes introns and joins exons to produce mature mRNA with continuous coding sequence that moves into the cytoplasm of a eukaryotic cell.

"Stringency" of hybridization reactions is readily determinable by one of ordinary skill in the art, and generally is an empirical calculation dependent upon probe length, washing temperature, and salt concentration. In general, longer probes require higher temperatures for proper annealing, while shorter probes need lower temperatures.

Hybridization generally depends on the ability of denatured DNA to re-anneal when complementary strands are present in an environment below their melting temperature. The higher the degree of desired homology between the probe and hybridizable sequence the higher is the relative temperature which can be used. As a result, it follows that higher relative temperatures would tend to make the reaction conditions more stringent, while lower temperatures less so. For additional details and explanation of stringency of hybridization reactions, see Ausubel et al., Current Protocols in Molecular Biology, Wiley Interscience Publishers, (1995) and in Current Protocols in Molecular Biology Copyright © 2007 by John Wiley and Sons, Inc., 2008.

As used herein, a "gene target" refers to the sequence derived from a biological sample that is labeled and suitable for hybridization to a gene probe affixed on a substrate and a "nucleotide target" refers to the sequence derived from a biological sample that is labeled and suitable for hybridization to a nucleotide probe affixed on a substrate.

The term "treatment" refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented. The practice of the present invention will employ, unless otherwise indicated, conventional techniques of molecular biology (including recombinant techniques), microbiology, cell biology and biochemistry, which are within the skill of the art.

"MicroRNA", also written as miRNA or miR, refers to any type of interfering RNAs, including but not limited to, endogenous microRNAs and artificial microRNAs. Endogenous microRNAs are small RNAs naturally present in the genome which are capable of modulation the productive utilization of mRNA. An artificial microRNA can be any type of RNA sequence, other than endogeneous microRNA, which is capable of modulation the productive utilization of mRNA. For instance, it includes sequences previously identified as siRNA, regardless of the mechanism of downstream processing of the RNA. A microRNA sequence can be an RNA molecule composed of any one or more of these sequences. Several types of agents are known that modulate microRNAs. These include, but are not limited to microRNA mimics and microRNA inhibitors.

A "miRNA mimic" is an agent used to increase the expression and/or function of a miRNA. The miRNA mimic can also increase, supplement, or replace the function of a natural miRNA. In one embodiment, the miRNA mimic may be a polynucleotide comprising the mature miRNA sequence. In another embodiment, the miRNA mimic may be a polynucleotide comprising the pri-miRNA or premiRNA sequence. The miRNA mimic may contain chemical modifications, such as locked nucleic acids, peptide nucleic acids, sugar modifications, such as 2'-O-alkyl (e.g. 2'-O-methyl, 2'-β-methoxyethyl), 2'-fluoro, and 4' thio modifications, and backbone modifications, such as one or more phosphorothioate, morpholino, or phosphonocarboxylate linkages.

A "miRNA inhibitor" is an agent that inhibits miRNA function in a sequence-specific manner. In one embodiment, the miRNA inhibitor is an antagomir. "Antagomirs" are single-stranded, chemically-modified ribonucleotides that are at least partially complementary to the miRNA sequence. Antagomirs may comprise one or more modified nucleotides, such as 2'-O-methyl-sugar modifications. In some embodiments, antagomirs comprise only modified nucleotides. Antagomirs may also comprise one or more phosphorothioate linkages resulting in a partial or full phosphorothioate backbone. To facilitate in vivo delivery and stability, the antagomir may be linked to a cholesterol moiety at its 3' end. Antagomirs suitable for inhibiting miRNAs may be about 15 to about 50 nucleotides in length, more preferably about 18 to about 30 nucleotides in length, and most preferably about 20 to about 25 nucleotides in length. "Partially complementary" refers to a sequence that is at least about 75%, 80%, 85%, 90%, 95%, 96%, 97%, 98%, or 99% complementary to a target polynucleotide sequence. The antagomirs may be at least about 75%, 80%, 85%, 90%, 95%, 96%, 97%, 98%, or 99% complementary to a mature miRNA sequence. In some embodiments, the antagomirs are 100% complementary to the mature miRNA sequence.

B. Description of the Molecules

The present disclosure relates to molecules which may be used as biomarkers for cardiovascular diseases and cardiovascular events. The molecules are described below, and reference is made to the NCBI gene and protein databases, for example, the version as updated 8 Feb. 2015.

(i) Cytochrome c Oxidase, Subunit I; COX1

The mRNAs coding for the mitochondria-encoded respiratory chain subunits COX1, COX2 and COX3 have specific translational regulators that have been defined in yeast that positively or negatively regulate translation. The remaining cytochrome oxidase (Cox) subunits are encoded by the nucleus.

Mss51 inactivation by the COX14-COA1-COA3 complex shuts off COX1 translation, preventing the assembly of cytochrome oxidase. In yeast, Cox2 is translated as a precursor (pCox2) with an amino-terminal 15 amino acid extension. Both termini are transported across the membrane and Cox2 is kept in an assembly-competent state by Cox20 (37). Next, Cox1 assembles with the first nuclear-encoded subunits, Cox6 and Cox5. Whether this association occurs prior to or after the insertion of co-factors into COX1 is unclear. Mutant analyses revealed that the Cox1-Cox5-Cox6 complex can subsequently form different assembly intermediates in the absence of either Cox2 or Cox3. A mitochondrial DNA mutation in COX1 leads to strokes, seizures, and lactic acidosis (38). Insulin sensitivity and aerobic fitness were increased after exercise training in obese persons, and the expression of COX1 was also increased (39).

The *Homo sapiens* COX1 mRNA sequence has been deposited in the NCBI database under the accession number NC_012920.1 (SEQ ID NO: 1). Its protein has been deposited under the accession number YP_003024028.1 (SEQ ID NO: 2). MT-COI (mitochondrial cytochrome oxidase 1) is used as synonym.

(ii) Cytochrome c Oxidase, Subunit IV, Isoform 1; COX4I1

Cytochrome c oxidase (COX) is the terminal enzyme of the mitochondrial respiratory chain. It is a multi-subunit enzyme complex that couples the transfer of electrons from cytochrome c to molecular oxygen and contributes to a proton electrochemical gradient across the inner mitochondrial membrane. The complex consists of 13 mitochondrial- and nuclear-encoded subunits. The mitochondrial-encoded subunits perform the electron transfer and proton pumping activities. The functions of the nuclear-encoded subunits are unknown but they may play a role in the regulation and assembly of the complex. COX subunit IV is the largest nucleus-encoded subunit of cytochrome c oxidase (COX; EC 1.9.3.1), the terminal enzyme complex of the mitochondrial electron transport chain. COX is an example of an unusual class of multisubunit enzyme complex found in both mitochondria and chloroplasts of eukaryotic cells. The novel feature of these complexes is their mixed genetic origin: in each complex, at least one of the polypeptide subunits is encoded in the genome of the organelle, with the remaining subunits encoded in the nucleus. Thus, 2 distinct genetic systems, each with its unique features and evolutionary constraints, must interact to produce these essential holoenzymes (40). In humans oxidative phosphorylation genes, such as COX4I1 and COIX10 (see below) were not found to be associated with IR and T2DM (41).

The *Homo sapiens* COX4I1 mRNA sequence has been deposited in the NCBI database under the accession number NM_001861.3 (SEQ ID NO: 3). Its protein has been deposited under the accession number NP_001852 (SEQ ID NO: 4).

(iii) Runt-Related Transcription Factor 2; RUNX2

RUNX2 has a primary role in the differentiation of osteoblasts and hypertrophy of cartilage at the growth plate, cell migration, and vascular invasion of bone; is expressed in vascular endothelial cells, breast cancer cells, and prostate cancer cells; is linked to vascular calcification in atherosclerotic lesions; and is expressed in adult bone marrow, thymus, and peripheral lymphoid organs (42). Activation of the PI3K/Akt pathway by oxidative stress mediated high glucose-induced increase of adipogenic differentiation in primary rat osteoblasts, as evidenced by an increase in Runx2 among others, such as adipocyte fatty acid binding protein (43, 44). Delayed bone regeneration and low bone mass in a rat model of T2DM was found to be due to impaired osteoblast function, evidenced by a reduction in Runx2 (45). Advanced glycation end products-induced vascular calcification was found to be mediated by oxidative stress, associated with an increase in Runx2. But in circulating osteogenic precursor cells reduced molecular expression of the osteoblast regulator gene Runx2 was associated with increased expression of the oxidative stress markers p66 (Shc) and SOD2 (46). Metformin induces osteoblast differentiation via orphan nuclear receptor SHP-mediated transactivation of Runx2 (47). Streptozotocin-induced diabetes increased expression of the receptor for activation of NFκB and decreased Runx2 expression in bone of rats (48). Obesity reduced bone density associated with activation of PPARγ and suppression of Wnt/β-catenin in rapidly growing male rats; Runx2 was decreased (49).

The *Homo sapiens* mRNA has been deposited in the NCBI database under the accession number NM_001015051.3 (SEQ ID NO: 5). Its protein has been deposited under the accession number AAI08920.1 and alternative protein (CCQ43044.1) (SEQ ID NO: 6).

(iv) Transcription Factor A, Mitochondrial; TFAM

This gene encodes a key mitochondrial transcription factor containing two high mobility group motifs. The encoded protein also functions in mitochondrial DNA replication and repair.

Sequence polymorphisms in this gene are associated with Alzheimer's and Parkinson's diseases. There are pseudogenes for this gene on chromosomes 6, 7, and 11. Exercise training in mice promoted eNOS-dependent mitochondrial biogenesis in heart, evidenced by an increase Tfam, as an essential step in cardiac glucose transport (50). At the other hand, mitochondrial uncoupling associated with reduction in TFAM reduced exercise capacity despite several skeletal muscle metabolic adaptations (51). Overexpression of TFAM protected 3T3-L1 adipocytes from NYGGF4 (PID1) overexpression-induced insulin resistance and mitochondrial dysfunction. (52)

The *Homo sapiens* mRNA sequence has been deposited in the NCBI database under the accession number NM_001270782.1. (SEQ ID NO: 8). Its protein has been deposited under the accession number NP_001257711.1 (SEQ ID NO: 9).

(v) Micro-RNA 26a

MiR-26a has been found to be associated with pulmonary hypertension (53) and to regulate vascular smooth muscle cell function (54). Its sequence has been deposited under NC_000003.12 and is shown in SEQ ID NO 10.

(vi) MicroRNA-30b miRNA-30b was found to play a role in calcific aortic valve disease as a regulator of human aortic valvular calcification and apoptosis through direct targeting of Runx2, Smad1, and caspase-3. Targeting of miRNA-30b could serve as a novel therapeutic strategy to limit progressive calcification in aortic stenosis (55). Its sequence has been deposited under number NC_000008.11 and is shown in SEQ ID NO: 11.

(viiI) MicroRNA-361

Micro-RNA-361 overexpression reduced hypoxia-induced cell proliferation and VEGF release indicating miR-361 involvement in the acquisition of an angiogenic phenotype by HUVEC. miR-361 effects on VEGF were enhanced by the coadministration of SRIF. Our results suggest that (1) SRIF regulates miR-361 expression through a control on HIF-1, (2) miR-361 affects HUVEC angiogenic phenotype, and (3) SRIF and miR-361 act cooperatively in limiting hypoxia-induced VEGF release (56). Its sequence has been deposited under number NC_000023.11 and is shown in SEQ ID NO: 12.

C. Panels of Biomarkers

One aspect of the disclosure relates to a cluster of molecules which affect the oxidative stress and resistance to oxidation in association with cardiovascular events in white blood cells, particularly monocytes. For this cluster of molecules, a change in expression levels may indicate that a patient has a cardiovascular disorder, has experienced a cardiovascular event, or is at risk for experiencing a cardiovascular event. Expression of select molecules may be used as biomarkers for specific indications. For example, a panel of biomarkers may be a genetic signature of a disorder. The panel of biomarkers may be a genetic signature of coronary stenosis. In some embodiments, the biomarker panel comprises at least one of COX1, COX4I1, TFAM, and RUNX2. In some embodiments, the panel of biomarkers may be a genetic signature of risk for experiencing cardiovascular events.

In certain embodiments, the biomarker panel comprises COX1. A decrease in COX1 expression in a patient sample, as compared with a reference measurement, may indicate that the patient is at risk for experiencing a cardiovascular event. The decrease in COX1 may also indicate that the patient is at risk, even if the patient does not yet have other symptoms of a disorder. The decreased expression of COX1 may also indicate that the patient has experienced a cardiovascular event or has a cardiovascular disorder, such as coronary stenosis. Decreased expression of COX1 may also indicate that a patient will respond poorly or will not respond to treatments for cardiovascular disorders. In some embodiments, the decrease in COX1 expression in a patient sample, as compared with a reference measurement, indicates that the patient is at risk for experiencing a cardiovascular event.

In certain embodiments, the biomarker panel comprises COX1 and at least one of COX4I1, TFAM, and RUNX2. In some embodiments, the biomarker panel comprises COX1 and COX4I1. A decrease in COX1 expression and a decrease in COX4I1 expression in a patient sample, as compared with reference measurements, may indicate that a patient (1) has undergone a cardiovascular event; (2) is at risk for experiencing a cardiovascular event; and/or (3) will respond poorly or will not respond to treatments for cardiovascular disorders.

In some embodiments, the biomarker panel comprises COX1, COX4I1, and TFAM. In some embodiments, the decrease in expression of COX1, COX4I1, and TFAM in a patient sample as compared with reference measurements indicates that the patient (1) has undergone a cardiovascular event; (2) is at risk for experiencing a cardiovascular event; and/or (3) will respond poorly or will not respond to treatments for cardiovascular disorders.

In certain embodiments, the biomarker panel comprises COX1, COX4I1, TFAM, and RUNX2. A decrease in COX1, COX4I1, TFAM, and RUNX2 expression in the patient sample, as compared with reference measurements, may indicate that the patient (1) has undergone a cardiovascular event; (2) is at risk for experiencing a cardiovascular event; and/or (3) will respond poorly or will not respond to treatments for cardiovascular disorders.

In certain embodiments, the biomarker panel further comprises miRNA markers, such as miR-30b and miR-26a. In some embodiments, the biomarker panel comprises miR-30b. A decrease in miR-30b in the patient sample, as compared with reference measurements, may indicate that the patient has (1) has undergone a cardiovascular event; (2) is at risk for experiencing a cardiovascular event; and/or (3) will respond poorly or will not respond to treatments for cardiovascular disorders. In some embodiments, the biomarker panel comprises miR-26a. A decrease in miR-26a in the patient sample, as compared with reference measurements, may indicate that the patient has (1) has undergone a cardiovascular event; (2) is at risk for experiencing a cardiovascular event; and/or (3) will respond poorly or will not respond to treatments for cardiovascular disorders.

In certain embodiments, the biomarker panel comprises COX1, COX4I1, TFAM, RUNX2 and miR-30b. A decrease in COX1, COX1, COX4I1, TFAM, RUNX2, and miR-30b in the patient sample, as compared with reference measurements, may indicate that the patient has (1) has undergone a cardiovascular event; (2) is at risk for experiencing a cardiovascular event; and/or (3) will respond poorly or will not respond to treatments for cardiovascular disorders.

In certain embodiments, the biomarker panel comprises COX1, COX4I1, TFAM, RUNX2, miR-30b, and miR-26a. A decrease in COX1, COX1, COX4I1, TFAM, RUNX2, miR-30b and miR-26a in the patient sample, as compared with reference measurements, may indicate that the patient has (1) has undergone a cardiovascular event; (2) is at risk for experiencing a cardiovascular event; and/or (3) will respond poorly or will not respond to treatments for cardiovascular disorders.

In certain embodiments, the biomarker panel comprises at least two of COX1, COX4I1, TFAM, RUNX2, miR-30b, and miR-26a. For example, the biomarker panel may comprise COX1 and miR-30b; COX1, COX4I1, and miR-30b; COX1, COX4I1, TFAM, and miR-30b; or COX1, COX4I1, TFAM, RUNX2, and miR-30b. The biomarker panel may comprise COX1 and miR-26a; COX1, COX4I1, and miR-26a; COX1, COX4I1, TFAM, and miR-26a; or COX1, COX4I1, TFAM, RUNX2, and miR-26a. The biomarker panel may comprise COX1, miR-30b61, and miR-26a; COX1, COX4I1, miR-30b, and miR-26a; COX1, COX4I1, TFAM, miR-30b, and miR-26a; or COX1, COX4I1, TFAM, RUNX2, miR-30b, and miR-26a.

In these examples, decreased expression in the at least two biomarkers may indicate that the patient (1) has undergone a cardiovascular event; (2) is at risk for experiencing a cardiovascular event; and/or (3) will respond poorly or will not respond to treatments for cardiovascular disorders.

D. Patients at Risk

One aspect of the present disclosure relates to identifying a patient at risk for developing one or more cardiovascular events. Cardiovascular events refer to any incidents that may cause damage to the heart muscle and/or tissues of the cardiovascular system. Exemplary cardiovascular events include but are not limited to cardiovascular death, myocardial infarction, stroke or transient ischemic attack, recurrent ischemia requiring PCI, recurrent angina requiring PCI, coronary bypass surgery, and surgery or stenting of peripheral arteries, or development of heart failure. Patients at risk for developing cardiovascular disease and/or experiencing one or more cardiovascular events have risk factors that include but are not limited to advanced age, history of smoking, elevated LDL, decreased HDL, elevated triglycerides, elevated blood glucose, type 2 diabetes, metabolic syndrome, elevated blood pressure, obesity, elevated CRP, elevated interleukin-6 (IL-6), elevated levels of adipocytokines, and elevated levels of systemic markers of oxidative stress, such as oxidized LDL (ox-LDL).

One aspect of the present disclosure relates to a method for identifying a patient at risk for experiencing one or more cardiovascular events, comprising: (a) obtaining a biological sample from the patient; (b) measuring expression of COX1 in the biological sample; and (c) comparing the expression of COX1 with reference measurements; wherein decreased expression of COX1 in the biological sample as compared to the reference measurements indicates that the patient is at risk for experiencing one or more cardiovascular events.

In some embodiments, the method further comprises measuring expression of COX4I1 in the biological sample in step (b), and comparing the expression of COX1 and COX4I1 with reference measurements, wherein reduced expression of COX1 and COX4I1 in the biological sample as compared to the reference measurements indicates that the patient is at risk for experiencing cardiovascular events.

Accordingly, a further aspect of the present disclosure relates to a method for identifying a patient at risk for experiencing one or more cardiovascular events, comprising: (a) obtaining a biological sample from the patient; (b) measuring expression of COX1 and COX4I1 in the biological sample; and (c) comparing the expression of COX1 and COX4I1 with reference measurements; wherein decreased expression of COX1 and COX4I1 in the biological sample as compared to the reference measurements indicates that the patient is at risk for experiencing one or more cardiovascular events.

The method of present inventions as embodied in this application can further comprises measuring expression of TFAM in the biological sample in step (b), and comparing the expression of COX1, COX4I1, and TFAM with reference measurements, wherein reduced expression of COX1, COX4I1, and TFAM compared to the reference measurements indicates that the patient is at risk for experiencing cardiovascular events. In yet another particular embodiment the methods of present invention further comprise measuring expression of TFAM and RUNX2 in the biological sample in step (b), and comparing the expression of COX1, COX4I1, TFAM, and RUNX2 with reference measurements, wherein reduced expression of COX1, COX4I1, TFAM, and RUNX2 compared to the reference measurements indicates that the patient is at risk for experiencing cardiovascular events.

In certain embodiments, the method further comprises measuring expression of at least one of miR-30b and miR-26a in the biological sample is step (b), and comparing the expression of at least one of miR-30b and miR-26a reference measurements; wherein decreased expression of at least one of miR-30b and miR-26a in the biological sample as compared to the reference measurements indicates that the patient is at risk for experiencing one or more cardiovascular events. In some embodiments, the method comprises (a) obtaining a biological sample from the patient; (b) measuring expression of COX1, COX4I1, TFAM, RUNX2, and miR-30b in the biological sample; and (c) comparing the expression of COX1, COX4I1, TFAM, RUNX2, and miR-30b with reference measurements; wherein decreased expression of COX1, COX4I1, TFAM, RUNX2, and miR-30b in the biological sample as compared to the reference measurements indicates that the patient is at risk for experiencing one or more cardiovascular events.

In some embodiments, the method comprises (a) obtaining a biological sample from the patient; (b) measuring expression of COX1, COX4I1, TFAM, RUNX2, and miR-26a in the biological sample; and (c) comparing the expression of COX1, COX4I1, TFAM, RUNX2, and miR-26a with reference measurements; wherein decreased expression of COX1, COX4I1, TFAM, RUNX2, and miR-26a in the biological sample as compared to the reference measurements indicates that the patient is at risk for experiencing one or more cardiovascular events.

A further aspect of the present disclosure relates to a the method for identifying a patient at risk for experiencing one or more cardiovascular events comprises (a) obtaining a biological sample from the patient; (b) measuring expression of COX1, COX4I1, TFAM, RUNX2, miR-30b, and miR-26a in the biological sample; and (c) comparing the expression of COX1, COX4I1, TFAM, RUNX2, miR-30b, and miR-26a with reference measurements; wherein decreased expression of COX1, COX4I1, TFAM, RUNX2, miR-30b, and miR-26a in the biological sample as compared to the reference measurements indicates that the patient is at risk for experiencing one or more cardiovascular events.

In some embodiments, the method further comprises measuring expression of COX1 in the biological sample in step (b), and comparing the expression of miR-30b and COX1 with reference measurements, wherein reduced expression of miR-30b and COX1 in the biological sample as compared to the reference measurements indicates that the patient is at risk for experiencing cardiovascular events. In certain embodiments, the method further comprises measuring expression of COX4I1 in the biological sample in step (b), and comparing the expression of miR-30b and COX1 and COX4I1 with reference measurements, wherein reduced expression of miR-30b and COX1 and COX4I1 compared to the reference measurements indicates that the patient is at risk for experiencing cardiovascular events. In other embodiments, the method further comprises measuring expression of TFAM in the biological sample in step (b), and comparing the expression of miR-30b and COX1, COX4I1 and TFAM with reference measurements, wherein reduced expression of miR-30b and COX1, COX4I1 and TFAM compared to the reference measurements indicates that the patient is at risk for experiencing cardiovascular events. In other embodiments, the method further comprises measuring expression of COX1 in the biological sample in step (b), and comparing the expression of miR-26a and COX1 with reference measurements, wherein reduced expression of miR-26a and COX1 in the biological sample as compared to the reference measurements indicates that the patient is at risk for experiencing cardiovascular events. In certain embodiments, the method further comprises measuring expression of COX4I1 in the biological sample in step (b), and comparing the expression of miR-26a and COX1 and COX4I1 with reference measurements, wherein reduced expression of miR-26a and COX1 and COX4I1 compared to the reference measurements indicates that the patient is at risk for experiencing cardiovascular events. In other embodiments, the method further comprises measuring expression of TFAM in the biological sample in step (b), and comparing the expression of miR-26a and COX1, COX4I1 and TFAM with reference measurements, wherein reduced expression of miR-26a and COX1, COX4I1 and TFAM compared to the reference measurements indicates that the patient is at risk for experiencing cardiovascular events.

Another aspect of the present disclosure relates to a method for predicting a subject's risk for experiencing a cardiovascular event, wherein the subject has one or more risk factors for cardiovascular disease, has coronary stenosis, is at risk for developing coronary stenosis, has previously experienced one or more cardiovascular events, or has not previously experienced a cardiovascular event, or any combination thereof, the method comprising: obtaining a biological sample from the subject, wherein the biological sample is selected from the group consisting of a blood sample, one or more monocytes, one or more macrophages, one or more microvesicles, one or more exosomes, one or more monocyte-derived exosomes, and any combination thereof, preparing the biological sample for measurement of gene expression therein; measuring expression of COX1 in the thus prepared biological sample, wherein expression comprises gene expression; and comparing the expression of COX1 with reference measurements; wherein decreased expression of COX1 in the biological sample as compared to the reference measurements indicates that the subject is at risk for experiencing a cardiovascular event.

In certain embodiments, the method further comprises measuring expression of at least one of COX4I1, TFAM, RUNX2, miR-30b, and miR-26a in the biological sample, and comparing expression of at least one of COX4I1, TFAM, RUNX2, miR-30b, and miR-26a with a reference measurement, wherein decreased expression of at least one of COX4I1, TFAM, RUNX2, miR-30b, and miR-26a and in the biological sample as compared to the reference measurements indicates that the subject is at risk for experiencing a cardiovascular event.

For example, the method may comprise measuring expression of COX1 and COX4I1 in the biological sample, and comparing expression of COX1 and COX4I1 with a reference measurement, wherein decreased expression of COX1 and COX4I1 in the biological sample as compared to the reference measurements indicates that the subject is at risk for experiencing a cardiovascular event.

The method may comprise measuring expression of COX1, COX4I1, and TFAM in the biological sample and comparing expression of COX1, COX4I1, and TFAM with a reference measurement, wherein decreased expression of COX1, COX4I1, and TFAM in the biological sample as compared to the reference measurements indicates that the subject is at risk for experiencing a cardiovascular event.

The method may comprise measuring expression of COX1, COX4I1, TFAM, and RUNX2 in the biological sample in the biological sample and comparing expression of COX1, COX4I1, TFAM, and RUNX2 with a reference measurement, wherein decreased expression of COX1, COX4I1, TFAM, and RUNX2 in the biological sample as compared to the reference measurements indicates that the subject is at risk for experiencing a cardiovascular event The method may comprise measuring expression of COX1, COX4I1, COX1, COX4I1, TFAM, RUNX2, and miR-30b in the biological sample in the biological sample in the biological sample and comparing expression of COX1, COX4I1, COX1, COX4I1, TFAM, RUNX2, and miR-30b with a reference measurement, wherein decreased expression of COX1, COX4I1, COX1, COX4I1, TFAM, RUNX2, and miR-30b in the biological sample as compared to the reference measurements indicates that the subject is at risk for experiencing a cardiovascular event.

The method may comprise measuring expression of COX1, COX4I1, COX1, COX4I1, TFAM, RUNX2, miR-30b, and miR-26a in the biological sample in the biological sample in the biological sample and comparing expression of COX1, COX4I1, COX1, COX4I1, TFAM, RUNX2, miR-30b, and miR-26a with a reference measurement, wherein decreased expression of COX1, COX4I1, COX1, COX4I1, TFAM, RUNX2, miR-30b, and miR-26a in the biological sample as compared to the reference measurements indicates that the subject is at risk for experiencing a cardiovascular event.

In some embodiments, the reference measurements are measurements of expression levels in biological samples obtained from healthy control patients. The reference measurements may be obtained from age-matched control patients. In certain embodiments, the control patients whose samples are used as reference measurements have fewer or no risk factors for cardiovascular disease and/or for cardiovascular events, as compared to the patients being tested according to the methods described herein. In some embodiments, the control patients are not currently suffering from cardiovascular disease, and are not undergoing treatment for cardiovascular disease. Conversely, in some embodiments, patients at risk are patients who suffer from cardiovascular disease. The cardiovascular disease may be a chronic condition, or may be an acute condition, and patients may suffer from one or more of the manifestations and/or underlying conditions of cardiovascular disease. Patients may also be at risk for developing cardiovascular disease, whether or not these patients have been previously diagnosed with cardiovascular disease.

In some embodiments, patients have at least one risk factor for cardiovascular disease. Risk factors may one or more of advanced age, history of smoking, elevated LDL, decreased HDL, elevated triglycerides, elevated blood glucose and type 2 diabetes, metabolic syndrome, elevated blood pressure, obesity, elevated CRP, and/or elevated oxidized LDL. Additional risk factors are excessive alcohol consumption, sugar consumption, family history, psychosocial factors, and high levels of air pollution. In certain embodiments, patients have a stenosis, for example, one or more of peripheral artery stenosis, angina (coronary artery stenosis), carotid artery stenosis, renal artery stenosis, pulmonary valve stenosis, mitral stenosis, tricuspid valve stenosis, aortic valve stenosis, and stenosis/strictures of other parts of the cardiovascular system. In some embodiments, the stenosis requires interventions such as diagnostic coronary angiography, a medical (drug) intervention, a life style modification, PCI, coronary bypass and/or valve surgery. The stenosis may not yet be diagnosed in the patient at risk. In some embodiments, patients are at risk for developing coronary artery stenosis.

In some embodiments, patients who are at risk for cardiovascular events may have previously experienced one or more cardiovascular events. Cardiovascular events refer to any incidents that may cause damage to the heart muscle and/or tissues of the cardiovascular system. Examples of cardiovascular events include but are not limited to cardiovascular death, myocardial infarction, stroke or transient ischemic attack, recurrent ischemia requiring percutaneous coronary intervention (PCI), recurrent angina requiring PCI, coronary bypass surgery, and/or surgery or stenting of peripheral arteries, or development of heart failure, arrhythmias, heart valve disease, cardiomyopathy, thrombosis, carotid and/or coronary artery disease. In certain embodiments, patients at risk have not experienced a cardiovascular event. Whether patients have experienced cardiovascular events or not they may be at risk for experiencing future cardiovascular events and/or for developing pathologies that lead to cardiovascular events. In some embodiments, the one or more cardiovascular events occur within 3 years of identifying the patient at risk for developing cardiovascular events. For example, the one or more cardiovascular events may occur within 1 year, or within 3, 6, 9, 12, 15, 18, 21, 24, 27, 30, or 32 months of identifying the patient at risk.

E. Response to Treatment

Some patients do not respond to treatments for cardiovascular disorders, so identification of patients who are likely, or conversely, not likely, to respond to treatments would enable doctors to tailor a specific treatment regimen to a specific patient. The biomarkers described herein may be used to determine whether a treatment for a cardiovascular disorder is effective for a specific patient.

One aspect of the disclosure relates to a method for determining a patient's response to a treatment for a cardiovascular disorder, comprising obtaining a biological sample from the patient; measuring expression of COX1 in the biological sample; and comparing the expression of COX1 with reference measurements; wherein decreased expression of COX1 in the biological sample as compared to the reference measurements indicates that the patient is not responding to the treatment. Increased expression of COX1 after treatment, as compared to expression of COX1 before treatment may indicate that the patient is responding to the treatment. In some embodiments, the method comprises measuring expression of COX1 and at least one of COX4I1, TFAM, RUNX2, miR-30b, and miR-26a.

In some embodiments, the method comprises obtaining a biological sample from the patient; measuring expression of COX1 and COX4I1 in the biological sample; and comparing the expression of COX1 and COX4I1 with reference measurements; wherein decreased expression of COX1 and COX4I1 in the biological sample as compared to the reference measurements indicates that the patient is not responding to the treatment. Increased expression of COX1 after treatment, as compared to expression of COX1 before treatment may indicate that the patient is responding to the treatment.

In some embodiments, the method further comprises measuring expression of at least one of TFAM, RUNX2, miR-30b, and miR-26a in the biological sample.

Accordingly, a method for determining a patient's response to a treatment for a cardiovascular disorder may comprise obtaining a biological sample from the patient; measuring expression of COX1, COX4I1, and TFAM in the biological sample; and comparing the expression of COX1, COX4I1, and TFAM with reference measurements indicates the patient is not responding to the treatment. Increased expression of COX1, COX4I1, and TFAM after treatment, as compared to expression of COX1, COX4I1, and TFAM before treatment may indicate that the patient is responding to the treatment.

In certain embodiments, a method for determining a patient's response to a treatment for at least one symptom of metabolic syndrome may comprise obtaining a biological sample from the patient; measuring expression of COX1, COX4I1, TFAM, and RUNX2 in the biological sample; and comparing the expression of COX1, COX4I1, TFAM, and RUNX2 with reference measurements indicates the patient is not responding to the treatment. Increased expression of COX1, COX4I1, TFAM, and RUNX2 after treatment, as compared to expression of COX1, COX4I1, TFAM, and RUNX2 before treatment may indicate that the patient is responding to the treatment.

In certain embodiments, a method for determining a patient's response to a treatment for at least one symptom of metabolic syndrome may comprise obtaining a biological sample from the patient; measuring expression of COX1, COX4I1, TFAM, and miR-30b in the biological sample; and comparing the expression of COX1, COX4I1, TFAM, and miR-30b with reference measurements indicates the patient is not responding to the treatment. Increased expression of COX1, COX4I1, TFAM, and miR-30b after treatment, as compared to expression of COX1, COX4I1, TFAM, and miR-30b before treatment may indicate that the patient is responding to the treatment.

In certain embodiments, a method for determining a patient's response to a treatment for at least one symptom of metabolic syndrome may comprise obtaining a biological sample from the patient; measuring expression of COX1, COX4I1, TFAM, miR-30b, and miR-26a in the biological sample; and comparing the expression of COX1, COX4I1, TFAM, miR-30b, and miR-26a with reference measurements indicates the patient is not responding to the treatment. Increased expression of COX1, COX4I1, TFAM, miR-30b, and miR-26a after treatment, as compared to expression of COX1, COX4I1, TFAM, miR-30b, and miR-26a before treatment may indicate that the patient is responding to the treatment.

Treatments for cardiovascular disorders may include surgical interventions and/or medications. Cholesterol lowering drugs such as statins and proprotein convertase subtilisin/kexin 9 (PCSK9) monoclonal antibodies, PPAR-agonists, such as fenofibrate and rosiglitazone, anti-hypertensive drugs such as beta-blockers, Ca-antagonists, ACE-inhibitors, and antidiabetic agents such as DPP4-I; GLP-1 agonist; SGLT2-I; TZD; U-500 regular insulin; biguanide; bile acid sequestrant; biphasic insulin; diabetes medications; diabetes mellitus; dipeptidyl peptidase 4 inhibitor; dopamine receptor agonist; glucagon-like peptide-1 agonist; insulin; intermediate-acting insulin; investigational agent; long-acting insulin; meglitinide; metformin, pramlintide; prandial insulin; rapid-acting insulin; review; short-acting insulin; sodium-glucose cotransporter 2 inhibitor; sulfonylurea; thiazolidinedione; metformin, may be additionally or alternatively be used.

Yet another aspect of the present disclosure relates to a method for determining a subject's response to treatment for a cardiovascular disorder, wherein the subject has one or more risk factors for cardiovascular disease, has coronary stenosis, is at risk for developing coronary stenosis, has previously experienced one or more cardiovascular events, or has not previously experienced a cardiovascular event, or any combination thereof, the method comprising: obtaining a biological sample from the subject, wherein the biological sample is selected from the group consisting of a blood sample, one or more monocytes, one or more macrophages, one or more microvesicles, one or more exosomes, one or more monocyte-derived exosomes, and any combination thereof; preparing the biological sample for measurement of gene expression therein; measuring expression of COX1 in the thus prepared biological sample, wherein expression comprises gene expression; and comparing the expression of COX1 with reference measurements; wherein decreased expression of COX1 in the biological sample as compared to the reference measurements indicates the subject is not responding to the treatment for the cardiovascular disorder. In certain embodiments, the patient is undergoing treatment for the cardiovascular disorder. In some embodiments, increased expression of COX1 after treatment as compared with the expression of COX1 before treatment indicates that the subject is responding to the treatment for the cardiovascular disorder.

A further aspect of the present disclosure relates to a method for determining a subject's response to treatment for a cardiovascular disorder, wherein the subject has one or more risk factors for cardiovascular disease, has coronary stenosis, is at risk for developing coronary stenosis, has previously experienced one or more cardiovascular events, or has not previously experienced a cardiovascular event, or any combination thereof, the method comprising: obtaining a biological sample from the subject, wherein the biological sample is selected from the group consisting of a blood sample, one or more monocytes, one or more macrophages, one or more microvesicles, one or more exosomes, one or more monocyte-derived exosomes, and any combination thereof; preparing the biological sample for measurement of gene expression therein; measuring expression of COX1 and COX4I1 in the thus prepared biological sample, wherein expression comprises gene expression; and comparing the expression of COX1 and COX4I1 with reference measurements; wherein decreased expression of COX1 and COX4I1 in the biological sample as compared to the reference measurements indicates the subject is not responding to the treatment for the cardiovascular disorder. In certain embodiments, the patient is undergoing treatment for the cardiovascular disorder. In some embodiments, increased expression of COX1 and COX4I1 after treatment as compared with the expression of COX1 and COX4I1 before treatment indicates that the subject is responding to the treatment for the cardiovascular disorder.

In some embodiments, the method further comprises measuring expression of at least one of TFAM, RUNX2, miR-30b, and miR-26a in the biological sample, wherein decreased expression of at least one of TFAM, RUNX2, miR-30b, and miR-26a in the biological sample as compared to the reference measurements indicates that the subject is not responding to treatment for the cardiovascular disorder. In certain embodiments, the patient is undergoing treatment for the cardiovascular disorder. In some embodiments, increased expression of at least one of TFAM, RUNX2, miR-30b, and miR-26a after treatment as compared with the expression of TFAM, RUNX2, miR-30b, and miR-26a before treatment indicates that the subject is responding to the treatment for the cardiovascular disorder.

For example, the method may comprise measuring expression of COX1, COX4I1, and TFAM in the biological sample and comparing expression of COX1, COX4I1, and TFAM with a reference measurement, wherein decreased expression of COX1, COX4I1, and TFAM in the biological sample as compared to the reference measurements indicates that the subject is not responding to treatment for the cardiovascular disorder. In certain embodiments, the patient is undergoing treatment for the cardiovascular disorder. In some embodiments, increased expression of COX1, COX4I1, and TFAM after treatment as compared with the expression of COX1, COX4I1, and TFAM before treatment indicates that the subject is responding to the treatment for the cardiovascular disorder.

The method may comprise measuring expression of COX1, COX4I1, TFAM, and RUNX2 in the biological sample in the biological sample and comparing expression of COX1, COX4I1, TFAM, and RUNX2 with a reference measurement, wherein decreased expression of COX1, COX4I1, TFAM, and RUNX2 in the biological sample as compared to the reference measurements indicates that the subject is not responding to treatment for the cardiovascular disorder. In certain embodiments, the patient is undergoing treatment for the cardiovascular disorder. In some embodiments, increased expression of COX1, COX4I1, TFAM, and RUNX2 after treatment as compared with the expression of COX1, COX4I1, TFAM, and RUNX2 before treatment indicates that the subject is responding to the treatment for the cardiovascular disorder.

The method may comprise measuring expression of COX1, COX4I1, TFAM, RUNX2, and miR-30b in the biological sample in the biological sample in the biological sample and comparing expression of COX1, COX4I1, TFAM, RUNX2, and miR-30b with a reference measurement, wherein decreased expression of COX1, COX4I1, TFAM, RUNX2, and miR-30b in the biological sample as compared to the reference measurements indicates that the subject is not responding to treatment for the cardiovascular disorder. In certain embodiments, the patient is undergoing treatment for the cardiovascular disorder. In some embodiments, increased expression of COX1, COX4I1, TFAM, RUNX2, and miR-30b after treatment as compared with the expression of COX1, COX4I1, TFAM, RUNX2, and miR-30b before treatment indicates that the subject is responding to the treatment for the cardiovascular disorder.

The method may comprise measuring expression of COX1, COX4I1, TFAM, RUNX2, miR-30b, and miR-26a in the biological sample in the biological sample in the biological sample and comparing expression of COX1, COX4I1, TFAM, RUNX2, miR-30b, and miR-26a with a reference measurement, wherein decreased expression of COX1, COX4I1, TFAM, RUNX2, miR-30b, and miR-26a in the biological sample as compared to the reference measurements indicates that the subject is not responding to treatment for the cardiovascular disorder. In certain embodiments, the patient is undergoing treatment for the cardiovascular disorder. In some embodiments, increased expression of COX1, COX4I1, TFAM, RUNX2, miR-30b, and miR-26a after treatment as compared with the expression of COX1, COX4I1, TFAM, RUNX2, miR-30b, and miR-26a before treatment indicates that the subject is responding to the treatment for the cardiovascular disorder.

A particular embodiment of present invention is a method for identifying a patient at risk for development of heart failure, comprising:
  a) obtaining a biological sample from the patient;
  b) measuring expression of COX1 in the biological sample; and
  c) comparing the expression of COX1 with reference measurements;
    wherein decreased expression of COX1 in the biological sample as compared to the reference measurements indicates that the patient is at risk for experiencing one or more cardiovascular events.

This method further can comprise measuring expression of COX4I1 in the biological sample in step (b), and comparing the expression of COX1 and COX4I1 with reference measurements, wherein reduced expression of COX1 and COX4I1 in the biological sample as compared to the reference measurements indicates that the patient is at risk for experiencing heart failure or can further comprising measuring expression of TFAM and RUNX2 in the biological sample in step (b), and comparing the expression of COX1, COX4I1, TFAM and RUNX2 with reference measurements, wherein reduced expression of COX1, COX4I1, TFAM and RUNX2 compared to the reference measurements indicates that the patient is at risk for experiencing heart failure.

In some embodiments of the methods described herein, expression comprises RNA expression.

A further aspect of the present disclosure relates to a method of analyzing a biological sample of a subject, wherein the subject has been diagnosed as having one or more risk factors for cardiovascular disease, has coronary stenosis, is at risk for developing coronary stenosis, has previously experienced one or more cardiovascular events, or has not previously experienced a cardiovascular event, or any combination thereof, the method comprising: reacting the biological sample with a first compound to form a first complex, the first complex comprising a COX1 expression product and the first compound, and measuring expression of COX1 in the subject.

In some embodiments, the method further comprises reacting the biological sample with a second compound to form a second complex, the second complex comprising a COX4I1 expression product and the second compound, and measuring expression of COX4I1 in the subject.

In some embodiments, the method further comprises reacting the biological sample with a third compound to form a third complex, the third complex comprising a TFAM expression product and the third compound, and measuring expression of TFAM in the subject.

In certain embodiments, the method further comprises reacting the biological sample with a fourth compound to form a fourth complex, the fourth complex comprising a RUNX2 expression product and the fourth compound, and measuring expression of RUNX2 in the subject.

In some embodiments, the method further comprises reacting the biological sample with a fifth compound to form a fifth complex, the fifth complex comprising a miR-30b expression product and the fifth compound, and measuring expression of miR-30b in the subject.

In some embodiments, the method further comprises reacting the biological sample with a sixth compound to form a sixth complex, the sixth complex comprising a miR-26a expression product and the sixth compound, and measuring expression of miR-26a in the subject.

A further aspect of the present disclosure relates to a biomarker panel comprising: a solid phase; a first compound bound to the solid phase, which first compound forms a first complex with a COX1 expression product.

In certain embodiments, the biomarker panel further comprises a second compound bound to the solid phase, which second compound forms a second complex with a COX4I1 expression product.

In some embodiments, the biomarker panel further comprises a third compound bound to the solid phase, which third compound forms a third complex with a TFAM expression product.

In certain embodiments, the biomarker panel further comprises a fourth compound bound to the solid phase, which fourth compound forms a fourth complex with a RUNX2 expression product; and a fifth compound bound to the solid phase, which fifth compound forms a fifth complex with a miR-30b expression product, and a sixth compound bound to the solid phase, which sixth compound forms a sixth complex with a miR-26a expression product.

Accordingly, in some embodiments, the biomarker panel further comprises a biological sample of a subject diagnosed as having one or more risk factors for cardiovascular disease, has coronary stenosis, is at risk for developing coronary stenosis, has previously experienced one or more cardiovascular events, or has not previously experienced a cardiovascular event, or any combination thereof.

In some embodiments, the biomarker panel further comprises discrete means for detecting each said complex.

F. Preparation and Use of Patient Samples and Biomarkers

In some embodiments of the disclosed methods, biological samples from patients are blood samples. In some embodiments, the blood samples comprise monocytes. Thus, the biological sample may be a monocyte preparation. Expression of biomarkers may comprise expression of the genes or gene products such as RNA. For example, measuring expression of biomarkers such as COX1; COX1 and COX4I1; or COX1, COX4I1, and at least one of TFAM, RUNX2, miR-30b, and miR-26a may comprise measuring expression of RNA, for example mRNA, of these genes.

Biological samples may be blood samples, for example, whole blood, blood plasma, blood plasma from which clotting factors have been removed, or one or more of the blood cells (also called hematocytes). Hematocytes may be red blood cells (erythrocytes), white blood cells (leukocytes), or platelets (thrombocytes). The leukocytes may be monocytes. In some embodiments, the monocytes have differentiated into tissue-resident macrophages or foam cells. Thus, in some embodiments, the biological sample comprises macrophages. The macrophages may be CD18+ macrophages. In certain embodiments, the biological sample comprises foam cells.

In some embodiments, the biological sample is a tissue sample, for example, heart tissue or vascular tissue. The tissue sample may be aortic tissue such as aortic valve tissue. In some embodiments, the vascular tissue is atherosclerotic. In some embodiments, the tissue sample comprises smooth muscle cells.

In certain embodiments, the reference measurements are obtained from reference samples, i.e., biological samples obtained from healthy control patients. The reference measurements may be obtained from age-matched control patients. In certain embodiments, the control patients whose samples are used as reference measurements have fewer or no risk factors for cardiovascular disease and/or for cardiovascular events, as compared to the patients being tested according to the methods described herein. In some embodiments, the control patients are not currently suffering from cardiovascular disease, and are not undergoing treatment for cardiovascular disease. The samples may also be biological samples obtained from the same patient at an earlier time point, for example, before treatment has begun and/or after angiographically diagnosed cardiovascular diseases. Accordingly, if taken at different time points, the biomarkers disclosed herein may be used to monitor the progression of a disorder in the same patient, or assess the efficacy of a treatment regimen.

(i) Isolation of Monocyte-Derived Microvesicles from Plasma Samples

Plasma samples from patients are easy to collect and contain (micro)RNAs (57-60), which have diagnostic potential in MetS and cardiovascular disease (61, 62). The main physiological carrier of plasma (micro)RNAs are microvesicles (MVs) which are small vesicles shed from almost all cell types under both normal and pathological conditions (63, 64). The term 'microvesicles' comprises both exosomes and shedding microvesicles (also called ectosomes or microparticles) (36). Interestingly, MVs bear surface receptors/ligands of the original cells and have the potential to selectively interact with specific target cells. They are involved in cell-to-cell communication including the communication between adipocytes and macrophages and between circulating monocytes and vascular endothelial cells (36, 60). Due to the presence of specific surface receptors/ligands, peripheral blood MVs can be divided in origin-based subpopulations which can be used to determine (micro)RNA expression profiles in MVs derived from one specific cell type (36). In detail, peripheral blood MVs derived from mononuclear phagocyte cell lineage can be detected with anti-CD14, anti-CD16, anti-CD206, anti-CCR2, anti-CCR3 and anti-CCR5 antibodies (59). By labeling the antibodies with a fluorescent group or magnetic particles, these cell-specific MVs can be isolated using FACS or magnetic cell separation technology. Thus unexpected advantages of monocyte-derived exosomes are that they bear the same surface markers as monocytes (e.g. CD14), that they can be purified from plasma, be it fresh or after freezing-thawing cycle(s), using the same methods as used for the purification of (CD14+) monocytes from fresh blood, and that expressions of some RNAs are similar to these in monocytes from which they are derived, whereas expressions of others are different or not detectable. The latter data suggest that these RNAs with similar expressions as in the parent cells are more important for communication with other cell types than RNAs which are not contained in exosomes of parent cells.

(ii) Preparation of Reagents Using Biomarkers

The biomarkers described herein may be used to prepare oligonucleotide probes and antibodies that hybridize to or specifically bind the biomarkers mentioned herein, and homologues and variants thereof.

(iii) Probes and Primers

A "probe" or "primer" is a single-stranded DNA or RNA molecule of defined sequence that can base pair to a second DNA or RNA molecule that contains a complementary sequence (the target). The stability of the resulting hybrid molecule depends upon the extent of the base pairing that occurs, and is affected by parameters such as the degree of complementarities between the probe and target molecule, and the degree of stringency of the hybridization conditions. The degree of hybridization stringency is affected by parameters such as the temperature, salt concentration, and concentration of organic molecules, such as formamide, and is determined by methods that are known to those skilled in the art. Probes or primers specific for the nucleic acid biomarkers described herein, or portions thereof, may vary in length by any integer from at least 8 nucleotides to over 500 nucleotides, including any value in between, depending on the purpose for which, and conditions under which, the probe or primer is used. For example, a probe or primer may be 8, 10, 15, 20, or 25 nucleotides in length, or may be at least 30, 40, 50, or 60 nucleotides in length, or may be over 100, 200, 500, or 1000 nucleotides in length. Probes or primers specific for the nucleic acid biomarkers described herein may have greater than 20-30% sequence identity, or at least 55-75% sequence identity, or at least 75-85% sequence identity, or at least 85-99% sequence identity, or 100% sequence identity to the nucleic acid biomarkers described herein. Probes or primers may be derived from genomic DNA or cDNA, for example, by amplification, or from cloned DNA segments, and may contain either genomic DNA or cDNA sequences representing all or a portion of a single gene from a single individual. A probe may have a unique sequence (e.g., 100% identity to a nucleic acid biomarker) and/or have a known sequence. Probes or primers may be chemically synthesized. A probe or primer may hybridize to a nucleic acid biomarker under high stringency conditions as described herein.

(iv) Diagnosis, Prognosis and Companion Diagnostics

In a preferred embodiment, the invention involves methods to assess quantitative and qualitative aspects of the biomarker gene expression(s), e.g. (m)RNAs of which the decreased expression as provided by the present invention is indicative for the combination of oxidative stress and inflammation related to cardiovascular diseases in said subject. Techniques well known in the art, e.g., quantitative or semi-quantitative RT PCR for instance real time RT PCR, for instance mRNA analysis by the fluorescence-based real-time reverse transcription polymerase chain reaction (qRT-PCR or RT-qPCR) or reverse transcription loop-mediated amplification (RT-LAMP), for instance one-step RT-LAMP, or real-time NASBA for detection, quantification and differentiation of the RNA and DNA targets (65), or Northern blot, can be used.

In a particular embodiment, the analysis techniques include the application of detectably-labeled probes or primers. The probes or primers can be detectably-labeled, either radioactively or non-radioactively, by methods that are known to those skilled in the art, and their use in the methods according to the invention, involves nucleic acid hybridization, such as nucleic acid sequencing, nucleic acid amplification by the polymerase chain reaction (e.g., RT-PCR), single stranded conformational polymorphism (SSCP) analysis, restriction fragment polymorphism (RFLP) analysis, Southern hybridization, northern hybridization, in situ hybridization, electrophoretic mobility shift assay (EMSA), fluorescent in situ hybridization (FISH), and other methods that are known to those skilled in the art.

By "detectably labeled" is meant any means for marking and identifying the presence of a molecule, e.g., an oligonucleotide probe or primer, a gene or fragment thereof, or a cDNA molecule. Methods for detectably-labeling a molecule are well known in the art and include, without limitation, radioactive labeling (e.g., with an isotope such as 32P or 35S) and nonradioactive labeling such as, enzymatic labeling (for example, using horseradish peroxidase or alkaline phosphatase), chemiluminescent labeling, fluorescent labeling (for example, using fluorescein), bioluminescent labeling, or antibody detection of a ligand attached to the probe. Also included in this definition is a molecule that is detectably labeled by an indirect means, for example, a molecule that is bound with a first moiety (such as biotin) that is, in turn, bound to a second moiety that may be observed or assayed (such as fluorescein-labeled streptavidin). Labels also include digoxigenin, luciferases, and aequorin.

(i) Treatment of Disorders

Detection of the biomarkers described herein may enable a medical practitioner to determine the appropriate course of action for a subject (e.g., further testing, drug or dietary therapy, surgery, no action, etc.) based on the diagnosis. Detection of the biomarkers described herein may also help determine the presence or absence of a cardiovascular disorder associated with activated monocytes, early diagnosis of such a disorder, prognosis of such a disorder, or efficacy of a therapy for such a disorder. In alternative aspects, the biomarkers and reagents prepared using the biomarkers may be used to identify therapeutics for such a disorder. The methods according to the invention allow a medical practitioner to monitor a therapy for a disorder associated with activated monocytes in a subject, enabling the medical practitioner to modify the treatment based upon the results of the test.

In said aspect of the disclosure, it has for example been found that a disorder associated with activated monocytes can be treated by administering to a subject in need thereof an effective amount of a therapeutic or a combination of therapeutics that increase(s) or decrease(s) the expression of RNAs (or their protein derivatives) in the monocytes or macrophages or any white blood cell. Said therapeutic may include an agent that increases the expression of any one of COX1, COX4I1, TFAM, and/or RUNX2 RNA, (or protein derivatives) and/or expression of any one of miR-30b and miR-26a.

Non-limiting examples of treatments are cholesterol lowering drugs such as statins and proprotein convertase subtilisin/kexin 9 (PCSK9) monoclonal antibodies, PPAR-agonists, such as fenofibrate and rosiglitazone, antihypertensive drugs such as beta-blockers, Ca-antagonists, ACE-inhibitors, and antidiabetic agents such as DPP4-I; GLP-1 agonist; SGLT2-I; TZD; U-500 regular insulin; biguanide; bile acid sequestrant; biphasic insulin; diabetes medications; diabetes mellitus; dipeptidyl peptidase 4 inhibitor; dopamine receptor agonist; glucagon-like peptide-1 agonist; insulin; intermediate-acting insulin; investigational agent; long-acting insulin; meglitinide; metformin, pramlintide; prandial insulin; rapid-acting insulin; review; short-acting insulin; sodium-glucose cotransporter 2 inhibitor; sulfonylurea; thiazolidinedione; metformin, may be additionally or alternatively be used.

The effective amount of a compound, which is required to achieve a therapeutic effect will, of course, vary with the type of therapeutic component, such as small molecules, peptides, etc.; the route of administration; the age and condition of the recipient; and the particular disorder or disease being treated. In all aspects hereof, the daily maintenance dose can be given for a period clinically desirable in the patient, for example from 1 day up to several years (e.g. for the mammal's entire remaining life); for example from about (2 or 3 or 5 days, 1 or 2 weeks, or 1 month) upwards and/or for example up to about (5 years, 1 year, 6 months, 1 month, 1 week, or 3 or 5 days). Administration of the daily maintenance dose for about 3 to about 5 days or for about 1 week to about 1 year is typical. Nevertheless, unit doses should preferably be administered from twice daily to once every two weeks until a therapeutic effect is observed.

In addition, the disclosure provides the use of an agent according to any one of the different embodiments hereof in the preparation of a pharmaceutical composition.

The compositions of the disclosure, for use in the methods of the disclosure, can be prepared in any known or otherwise effective dosage or product form suitable for use in providing topical or systemic delivery of the therapeutic compounds, which would include both pharmaceutical dosage forms as well as nutritional product forms suitable for use in the methods described herein.

The above-mentioned components may be administrated to induce an increase or a decrease of RNAs or their protein derivatives in myeloid cells in particular in blood monocytes. Such administration can be in any form by any effective route, including, for example, oral, parenteral, enteral, intraperitoneal, topical, transdermal (e.g., using any standard patch), ophthalmic, nasally, local, non-oral, such as aerosol, spray, inhalation, subcutaneous, intravenous, intramuscular, buccal, sublingual, rectal, vaginal, intra-arterial, and intrathecal, etc. Oral administration is preferred. Such dosage forms can be prepared by conventional methods well known in the art, and would include both pharmaceutical dosage forms as well as nutritional products.

A further aspect of the present disclosure relates to a method for treating a patient (or subject) who has a cardiovascular disorder or is at risk for experiencing a cardiovascular event, the method comprising: identifying the subject who has a cardiovascular disorder or is at risk for experiencing a cardiovascular event, wherein the subject has been determined to have a cardiovascular disorder or be at risk for experiencing a cardiovascular event by a method comprising: measuring expression of COX1 in a sample from the subject; and comparing the expression of COX1 in the subject sample to the expression of COX1 in a reference measurement such as control sample taken from a control subject; wherein finding equivalent or increased expression of COX1 in the subject sample as compared to the control sample determines that the subject is likely to respond to treatment for the cardiovascular disorder; and treating the subject who has a cardiovascular disorder or is at risk for experiencing a cardiovascular event, wherein the treatment is selected from lifestyle changes, surgery, and a medicament.

In some embodiments, the method further comprises measuring expression of COX4I1 in the sample from the subject; and comparing the expression of COX4I1 in the subject sample to the expression of COX4I1 in a control sample taken from a control subject; wherein finding equivalent or increased expression of COX4I1 in the subject sample as compared to the control sample determines that the subject is likely to respond to treatment for the cardiovascular disorder; and treating the subject has a cardiovascular disorder or is at risk for experiencing a cardiovascular event, wherein the treatment is selected from lifestyle changes, surgery, and a medicament.

Still another aspect of the present disclosure relates to a method for treating a patient (or subject) who has a cardiovascular disorder or is at risk for experiencing a cardiovascular event, the method comprising: identifying the subject who has a cardiovascular disorder or is at risk for experiencing a cardiovascular event, wherein the subject has been determined to have a cardiovascular disorder or be at risk for experiencing a cardiovascular event by a method comprising: measuring expression of COX1 and COX4I1 in a sample from the subject; and comparing the expression of COX1 and COX4I1 in the subject sample to the expression of COX1 and COX4I1 in a control sample taken from a control subject; wherein finding equivalent or increased expression of COX1 and COX4I1 in the subject sample as compared to the control sample determines that the subject is likely to respond to treatment for the cardiovascular disorder; and treating the subject who has a cardiovascular disorder or is at risk for experiencing a cardiovascular event, wherein the treatment is selected from lifestyle changes, surgery, and a medicament.

In some embodiments, the method further comprises measuring expression of TFAM in the sample from the subject; and comparing the expression of TFAM in the subject sample to the expression of TFAM in a control sample taken from a control subject; wherein finding equivalent or increased expression of TFAM in the subject sample as compared to the control sample determines that the subject is likely to respond to treatment for the cardiovascular disorder; and treating the subject who has a cardiovascular disorder or is at risk for experiencing a cardiovascular event, wherein the treatment is selected from lifestyle changes, surgery, and a medicament.

Still another aspect of the present disclosure relates to a method for treating a patient (or subject) who has a cardiovascular disorder or is at risk for experiencing a cardiovascular event, the method comprising: identifying the subject who has a cardiovascular disorder or is at risk for experiencing a cardiovascular event, wherein the subject has been determined to have a cardiovascular disorder or be at risk for experiencing a cardiovascular event by a method comprising: measuring expression of COX1, COX4I1, and TFAM in a sample from the subject; and comparing the expression of COX1, COX4I1 and TFAM in the subject sample to the expression of COX1, COX4I1, and TFAM in a control sample taken from a control subject; wherein finding equivalent or increased expression of COX1, COX4I1, and TFAM in the subject sample as compared to the control sample determines that the subject is likely to respond to treatment for the cardiovascular disorder; and treating the subject who has a cardiovascular disorder or is at risk for experiencing a cardiovascular event, wherein the treatment is selected from lifestyle changes, surgery, and a medicament.

In some embodiments, the method further comprises measuring expression of RUNX2 in the sample from the subject; and comparing the expression of RUNX2 in the subject sample to the expression of RUNX2 in a control sample taken from a control subject; wherein finding equivalent or increased expression of RUNX2 in the subject sample as compared to the control sample determines that the subject is likely to respond to treatment for the cardiovascular disorder; and treating the subject who has a cardiovascular disorder or is at risk for experiencing a cardiovascular event, wherein the treatment is selected from lifestyle changes, surgery, and a medicament.

A further aspect of present disclosure relates to a method for treating a patient (or subject) who has a cardiovascular disorder or is at risk for experiencing a cardiovascular event, the method comprising: identifying the subject who has a cardiovascular disorder or is at risk for experiencing a cardiovascular event, wherein the subject has been determined to have a cardiovascular disorder or be at risk for experiencing a cardiovascular event by a method comprising: measuring expression of COX1, COX4I1, TFAM, and RUNX2 in a sample from the subject; and comparing the expression of COX1, COX4I1, TFAM, and RUNX2 in the subject sample to the expression of COX1, COX4I1, TFAM, and RUNX2 in a control sample taken from a control subject; wherein finding equivalent or increased expression of COX1, COX4I1, TFAM, and RUNX2 in the subject sample as compared to the control sample determines that the subject is likely to respond to treatment for the cardiovascular disorder; and treating the subject who has a cardiovascular disorder or is at risk for experiencing a cardiovascular event, wherein the treatment is selected from lifestyle changes, surgery, and a medicament.

In some embodiments, the method further comprises measuring expression of miR-30b in the sample from the subject; and comparing the expression of miR-30b in the subject sample to the expression of miR-30b in a control sample taken from a control subject; wherein finding equivalent or increased expression of miR-30b in the subject sample as compared to the control sample determines that the subject is likely to respond to treatment for the cardiovascular disorder; and treating the subject who has a cardiovascular disorder or is at risk for experiencing a cardiovascular event, wherein the treatment is selected from lifestyle changes, surgery, and a medicament.

A further aspect of present disclosure relates to a method for treating a patient (or subject) who has a cardiovascular disorder or is at risk for experiencing a cardiovascular event, the method comprising: identifying the subject who has a cardiovascular disorder or is at risk for experiencing a cardiovascular event, wherein the subject has been determined to have a cardiovascular disorder or be at risk for experiencing a cardiovascular event by a method comprising: measuring expression of COX1, COX4I1, TFAM, RUNX2, and miR-30b in a sample from the subject; and comparing the expression of COX1, COX4I1, TFAM, RUNX2, and miR-30b in the subject sample to the expression of COX1, COX4I1, TFAM, RUNX2, and miR-30b in a control sample taken from a control subject; wherein finding equivalent or increased expression of COX1, COX4I1, TFAM, RUNX2, and miR-30b in the subject sample as compared to the control sample determines that the subject is likely to respond to treatment for the cardiovascular disorder; and treating the subject who has a cardiovascular disorder or is at risk for experiencing a cardiovascular event, wherein the treatment is selected from lifestyle changes, surgery, and a medicament.

In some embodiments, the method further comprises measuring expression of miR-26a in the sample from the subject; and comparing the expression of miR-26a in the subject sample to the expression of miR-26a in a control sample taken from a control subject; wherein finding equivalent or increased expression of miR-26a in the subject sample as compared to the control sample determines that the subject is likely to respond to treatment for the cardiovascular disorder; and treating the subject who has a cardiovascular disorder or is at risk for experiencing a cardiovascular event, wherein the treatment is selected from lifestyle changes, surgery, and a medicament.

Another aspect of present disclosure relates to a method for treating a patient (or subject) who has a cardiovascular disorder or is at risk for experiencing a cardiovascular event, the method comprising: identifying the subject who has a cardiovascular disorder or is at risk for experiencing a cardiovascular event, wherein the subject has been determined to have a cardiovascular disorder or be at risk for experiencing a cardiovascular event by a method comprising: measuring expression of COX1, COX4I1, TFAM, RUNX2, miR-30b, miR-26a in a sample from the subject; and comparing the expression of COX1, COX4I1, TFAM, RUNX2, miR-30b, miR-26a in the subject sample to the expression of COX1, COX4I1, TFAM, RUNX2, miR-30b, miR-26a in a control sample taken from a control subject; wherein finding equivalent or increased expression of COX1, COX4I1, TFAM, RUNX2, miR-30b, miR-26a in the subject sample as compared to the control sample determines that the subject is likely to respond to treatment for the cardiovascular disorder; and treating the subject who has a cardiovascular disorder or is at risk for experiencing a cardiovascular event, wherein the treatment is selected from lifestyle changes, surgery, and a medicament.

EXAMPLES

Having provided a general disclosure, the following examples help to illustrate the general disclosure. These specific examples are included merely to illustrate certain aspects and embodiments of the disclosure, and they are not intended to be limiting in any respect. Certain general principles described in the examples, however, may be generally applicable to other aspects or embodiments of the disclosure.

Example 1: RNA Biomarkers Associated with the Occurrence of Cardiovascular Diseases First, we tested the reproducibility of RNA analysis in monocytes of healthy individuals. Blood samples were collected from 13 healthy individuals at week 0, week 1 and week 2. Blood monocytes were isolated freshly, and RNA was extracted and RNA expressions were measured by RT-PCR. Mean areas under the curves (AUC) were 0.54 for COX1 and for COX4I1, 0.54 for RUNX2 and 0.52 for TFAM (AUC=0.50) means that there is no evidence that the data obtained with the test distinguish between groups) and for COX4I1.

Seventy-one of 87 patients were found to have stenosed coronary arteries: 20% with 1 diseased artery, 42% with 2, and 38% with 3 diseased arteries. We refer to them as cases. Sixteen of them had no significant coronary stenosis; we refer to them as controls. Cases were more often male and (ex-) smoker. They were more often treated with antihypertensive drugs, in particular beta-blockers, and had higher diastolic blood pressure. They had lower HDL-cholesterol levels and higher IL-6 and hs-CRP. BMI, levels of leptin, adiponectin, glucose and insulin, triglycerides, LDL-cholesterol and ox-LDL, and HOMA-IR (as measure of insulin resistance) were similar in cases and controls (Table 1). They were treated more often with statin, that could explain why LDL-cholesterol and ox-LDL levels were not different (Table 1).

RNA expressions of COX4I1, RUNX2, and TFAM were lower in cases than in controls. COX1 tended to be lower (Table 1). ROC analysis confirmed that COX1 (Area under the curve, AUC: 0.64, 95% CI: 053-0.74); OR: 6.08, 1.3-28), COX4I1 (AUC: 0.72, 95% CI: 0.62-0.81; OR: 4.7, 1.4-16) and TFAM (AUC: 0.77, 95% 0.67-0.81; OR: 6.5, 2.0-21) were related to CAD (Table 2). Table 2 shows the additive value in discriminating between high-risk patients without and with coronary stenosis. In particular, combinations of COX1 with TFAM, and COX4i1 with RUNX2, and TFAM with RUNX2 had additive value. Low expression of COX1 in monocytes was associated with coronary artery stenosis (OR, 6.30; 95% CI, 1.31-29), previous history of myocardial ischemia (OR: 4.05; 95% CI, 1.17-14) and previous history of unstable angina (OR: 10; 95% CI, 1.84-59), after adjustment for age, gender, (ex) smoking, diabetes, MetS, blood pressure, HOMA-IR, LDL- and HDL-cholesterol, triglycerides, BMI, adiponectin, leptin and hs-CRP and IL-6. Low expression of COX4I1 was only associated with coronary artery stenosis (OR, 6.20; 95% CI, 1.31-29). Low expression of TFAM was also associated with coronary artery stenosis (OR, 5.87; 95% CI, 1.79-19).

Expressions of miR-26a, miR-30b and miR-361 were lower in patients with coronary stenosis (Table 1). ROC analysis revealed that only miR-26a and miR-30b were associated with coronary stenosis (Table 2). Of interest, the combination of miR-30b with TFAM had the highest sensitivity and specificity for prediction of coronary stenosis.

Stepwise multivariate regression analysis showed that COX4I1 and TG predicted COX1 ($R^2=0.30$; P<0.0001). TFAM, COX1, and RUNX2 predicted COX4I1 ($R^2=0.46$; P<0.0001). TFAM, hs-CRP and COX4I1 predicted RUNX2 ($R^2=0.39$; P<0.0001). COX4I1, RUNX2, and miR-30b predicted TFAM ($R^2=0.40$; P<0.0001). The multivariate regression analysis model contained age, gender, smoking, T2DM, MetS, BMI, HOMA-IR, BP, TG, HDL cholesterol, LDL cholesterol, hs-CRP, leptin and adiponectin. T2DM and BP predicted miR-30b ($R^2=0.29$; P<0.0001). MiR-30b and adiponectin predicted miR-26a.

In aggregate, COX1, COX4I1, TFAM, RUNX2, and miR-26a and miR-30b were in a cluster that was associated with coronary stenosis together with other risk factors T2DM, hypertension (BP), high TG, and hs-CRP, and low adiponectin (indicating metabolic unhealthy obesity).

Example 2: Expression Analysis in Microvesicles

Microvesicles were isolated from plasma of 19 patients. RNA was isolated and RT-PCR was performed COX1 and COX4I1 expression was compared in extracts of monocytes and plasma of the same patients. COX1 expression was 0.95±0.29 in monocytes and 0.96±0.63 in microvesicles.

P-value in paired t-test was 0.985. AUC was 0.54, indicating very significant overlap of areas (AUC in case of 100% overlap is 0.50). COX4I1 expression was 1.12±0.30 in monocytes and 1.16±0.64 in microvesicles. P-value in paired t-test was 0.780. AUC was 0.52. These data show that microvesicles can be used as a proxy of monocytes. Visualisation of microvesicles using NanoSight (Malvern) showed that antibody-mediated enriched microvesicles predominantly were exosomes.

Because monocyte-derived microvesicles (e.g., exosomes) can be used to obtain similar or identical RNA expression data as compared with monocytes, miRNAs were isolated from (1) microvesicles isolated from plasma samples and (2) purified from monocytes. The expression of miR-26A, miR-30b and miR-361 in microvesicles and monocytes was compared. P-values determined by paired t-test were 0.92, <0.001, and 0.10. AUCs were 0.51, 0.85 (p<0.001 for difference) and 0.60. Accordingly, monocyte-derived microvesicles obtained from patient plasma samples can also be used as the source material (biological sample) for miRNAs in the biomarker panels as disclosed herein.

We then isolated CD14+ microvesicles from plasma of 96 high risk patients undergoing coronary angiography for established or suspected stable CAD of whom 69 had CAD with significant stenosis (≥30%). Thirty-seven CAD patients had at least one new event within the next 4.3 years. FIG. 1 shows representative distribution profiles of microvesicles isolated form plasma obtained with Malvern Nanoparticle Tracking Analysis (NTA) system. Cryo-TEM confirmed size distribution. Median sizes of microvesicles were not different in patients with and without CAD; size corresponded to that of exosomes. Also number of exosomes isolated from 1 ml plasma was not different between groups. We compared two independent biological samples from 8 subjects. Variation coefficients of microvesicle peak size were 8.2±4.9%; these of concentration were 6.4±5.4%. RNA expression of MT-COI was lower in CAD patients (1.08±0.72 vs. 1.92±1.24; p=0.0023) (FIG. 2, A-B). There was no difference in the expression of COX4I between CAD patients and subjects without CAD. Expression levels of the experimentally determined housekeeping genes for RNA extracted from microvesicles were not different between groups. Expressions of B2M were 1.51±0.77 in patients without and 1.38±0.82 in patients with CAD. Corresponding expressions of PPIA were 0.97±0.45 and 1.08±0.62. Total RNA amounts extracted from microvesicles were not different between CAD patients and subjects without significant stenosis. Expressions of RPL13A were 1.27±0.77 and 1.11±0.52. Expressions of RPS18 were 1.16±0.48 and 1.15±0.89. Expressions of YWHAZ were 1.06±0.38 and 1.04±0.38. Mean expressions of 5 housekeeping genes were 1.14±0.14 and 1.15±0.28. Variation coefficients of expression of MT-COI were 13±7%; these of COX4I1 were 27±16%. We also measured COX10 expressions in microvesicles but replicate variability and variability was too high. OR of CAD for patients with low MT-COI, determined by logistic regression analysis was 2.64 (95% CI: 1.06-6.60). Low MT-COI was no more related to CAD after adjustment for age, gender, smoking (OR: 2.58; 95% CI: 0.71-9.46), and after further adjustment for obesity, T2D and hypertension (2.01; 0.51-8.07).

Example 3: Prediction of Future Cardiovascular Events on Basis of RNA and microRNA Markers in Monocytes We followed 63 of those 71 CAD patients with coronary stenosis for at least 1 year; mean follow up was 1420 days. Thirty-seven CHD patients had 46 new cardiovascular events: cardiovascular death (n=1), recurrent ischemia/angina (n=35) requiring PCI being PTCA eventually combined with stenting, coronary bypass surgery (n=7), and surgery/stenting of peripheral arteries (n=2). Table 3 shows that characteristics of patients without and with future events were similar. COX1 expressions in monocytes of patients with future events collected at baseline were lower. ROC analysis revealed significant relation between COX1 and future cardiovascular events. OR of cardiovascular events in patients with low COX1 was 9.3 (2.8-31). COX4I1, RUNX2 and TFAM expressions in patients without and with new events were similar, but lower than in patients without stenosis (Table 1). MiR-26a and miR-30b were also not lower in patients with future events (Table 3).

Figure 3:
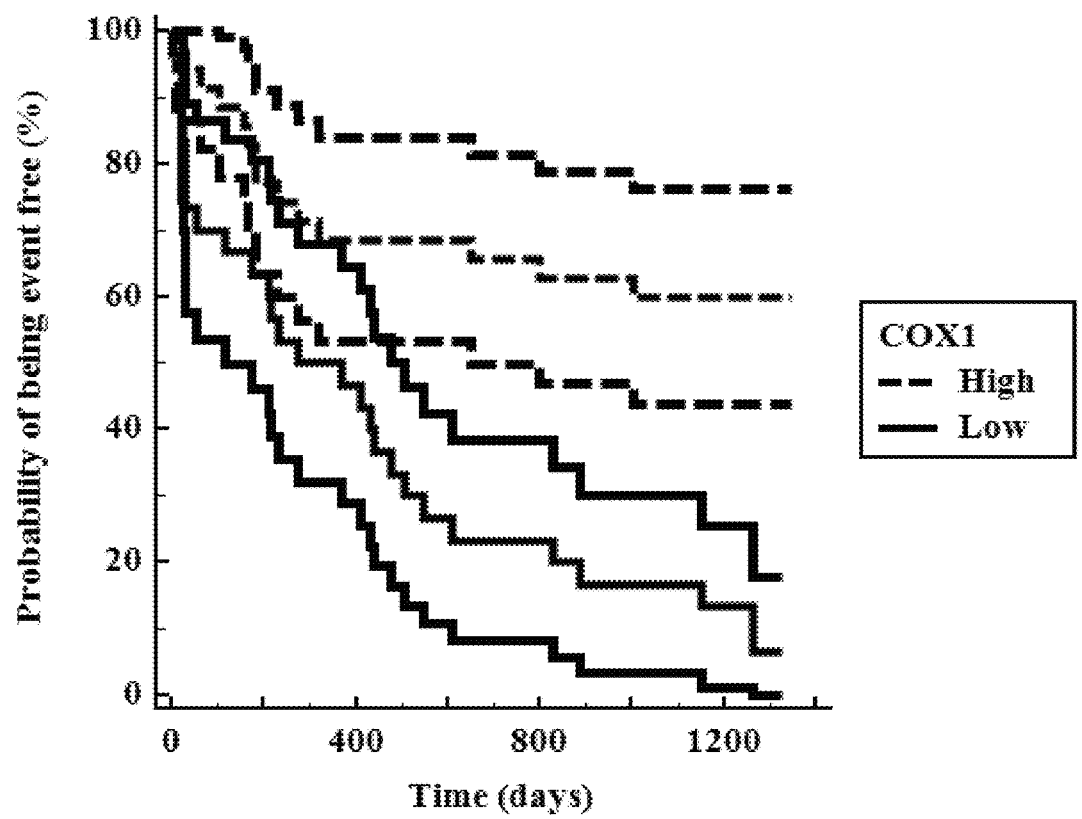
FIG. 3: Event free probability according to COX1 group. Data are represented as Kaplan-Meier graphs (mean with 95 CI intervals). When more than one event occurred in the same patients, the date of the first event was considered. Hazard ratio according to COX1 group was 0.26 (0.12-0.54 for patients with high COX1 and 3.9 (1.8-8.7) for patients with low COX1. Cut-off value of COX1, determined by ROC analysis, was 0.962. An event is cardiovascular death, a myocardial infarction or any other acute coronary syndrome as unstable angina or stroke, recurrent ischemia requiring a PCI procedure (PTCA, stenting), coronary bypass surgery, and/or surgery/stenting of peripheral arteries. Along the y-axis the probability of NOT having such an event according to time (x-axis) is illustrated. When more than one event occurred in the same patients, the date of the first event was considered. Hazard ratio according to COX1 group was 0.26 (0.12-0.54 for patients with high COX1 and 3.9 (1.8-8.7) for patients with low COX1. Cut-off value of COX1, determined by ROC analysis, was 0.962.

Although ROC analysis and Fisher's exact testing allow identifying biomarkers which discriminate between patients who do not or do develop new cardiovascular events, they do not allow determining the rate at which those new events do occur. In contrast, Kaplan-Meier and Cox proportional hazards regression build a predictive model for time-to-event data and produces a survival function that predicts the probability that the event of interest has occurred at a given time for given values of the predictor variables. FIG. 3 shows probability of being event free in relation to COX1 level. Hazard ratio was 0.33 (0.17-0.67) for patients with high COX1 and 3.1 (1.6-5.9) for patients with low COX1. Low COX1 predicted future cardiovascular events in patients with coronary stenosis during a 3-year follow-up (n=63), independent of age, gender, (ex) smoking, metabolic syndrome, diabetes, blood pressure, HOMA-IR, blood lipids, BMI, adiponectin, leptin, hs-CRP and number of diseased vessels. Its adjusted Odds Ratio was 3.94 (95% CI: 1.82-8.53).

During further follow-up (mean 2049 days, of 31 patients with recurrent ischemia/angina, 1 other patients died from cardiovascular complications, 1 patient had a recurrent AMI, 2 had an ischemic stroke and 1 in-stent stenosis. Adjusted Odds Ratio was 4.40 (1.81-11).

Multiple regression analysis including all established and emerging risk factors, and gene expressions, revealed COX1 was predicted by COX4I, TG and smoking ($R^2=0.44$; P<0.0001). COX4I1 was predicted by COX1, TFAM, age, glucose, and smoking ($R^2=0.63$; P<0.0001). TFAM was predicted by RUNX2 ($R^2=0.26$; P=0.002). The correlations between COX1, COX4I1, TFAM and RUNX2, and the fact that TFAM and RUNX2, as COX4I1 were already decreased at baseline, support inclusion of these four mRNAs in the prediction model of future cardiovascular events.

COX1 is part of the L-strand transcript of the mitochondrial genome. The transcription of the polycistronic mt-RNA precursors is controlled by TFAM, TFBM (TFB2M) and mitochondrial polymerase. These facts imply that COX1 is under control of TFAM. Since the genes of the reparatory chain polypeptides are split between the mitochondrial (e.g. COX1) and the nuclear genome (e.g. COX4I1), there must be ways to coordinate expression of these genes. Frame work analysis revealed that TFAM (TFBM, TFB2M), which are mitochondrial transcription factors, may link to the expression of other nuclear encoded mitochondrial proteins such as COX4I1 through interaction with RUNX2 and nuclear respiratory factor (NRFs). This data supports the clustering of COX1, COX4I1, TFAM and RUNX2.

Example 4: Prediction of Future Cardiovascular Events on Basis of RNA and microRNA Markers in Microvesicles Thirty-seven CAD patients had a new event: cardiovascular death (n=1), recurrent ischemia/angina requiring unplanned PCI or coronary bypass surgery (n=31), other cardiac surgery (valve; 2) and surgery/stenting of peripheral arteries (n=3). Supplement table 3 shows that clinical characteristics of CAD patients without and with a new event were very similar. However, MT-COI, but not COX4I1, expressions were lower in CAD patients with a new event (FIG. 2, C-D). Expressions of COX10 (were also not different (2.37±2.15 vs. 2.03±2.32). Expressions of B2M were 1.58±0.84 in CAD patients without new events, and 1.21±0.77 in CAD patients with new events. Corresponding expressions of PPIA were 1.09±0.83 and 1.08±0.89. Expressions of RPL13A were 0.99±0.38 and 1.20±0.60. Expressions of RPS18 were 1.22±0.66 and 1.06±0.47. Expressions of YWHAZ were 1.13±0.43 and 0.97±0.32. Mean expressions of 5 housekeeping genes were 1.12±0.11 and 1.11±0.11.

Figure 4:
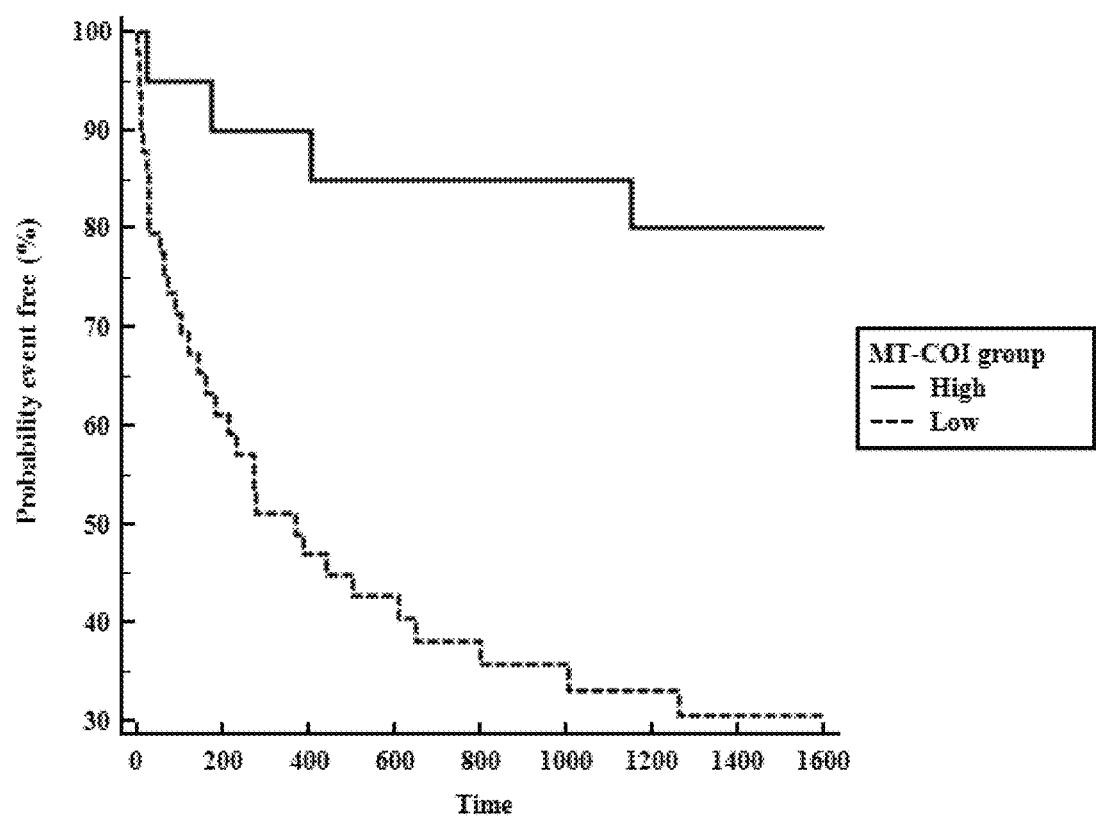
FIG. 4: Event free probability according to MT-COI group. Data are represented as Kaplan-Meier graphs (mean with 95 CI intervals). When more than one event occurred in the same patients, the date of the first event was considered. Hazard ratio was 0.22 (0.11-0.43) for patients with high MT-COI and 4.58 (2.34-8.97) for patients with low MT-COI.
Figure 5B:
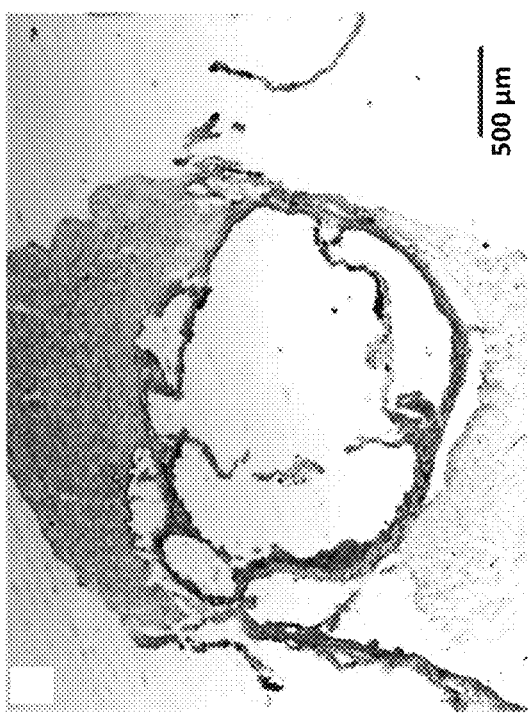
FIG. 5: Atherosclerotic plaques in aortic arch of control and caloric-restricted mice: representative sections of atherosclerotic plaques in which macrophages are stained with anti-Mac-3 antibody (control DKO in FIG. 5A; caloric-restricted DKO in FIG. 5B) and ox-LDL is stained with mAb4E6 (control DKO in FIG. 5C; caloric-restricted DKO in FIG. 5D) are shown.
Figure 5D:
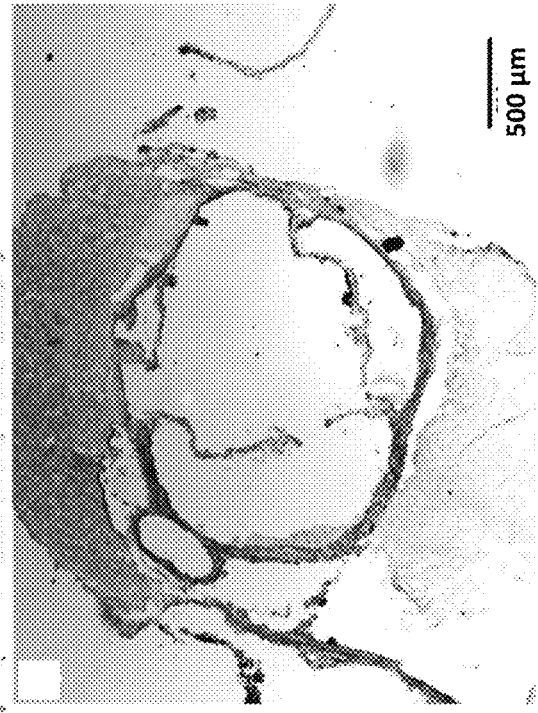
Figure 5A:
Figure 5C:

During further follow-up (mean 2049 days, of 31 patients with recurrent ischemia/angina, 1 other patients died from cardiovascular complications, 1 patient had a recurrent AMI, 2 had an ischemic stroke and 1 in-stent stenosis. Adjusted Odds Ratio was 4.40 (1.81-11). Kaplan-Meier analysis revealed that patients with low MT-COI had a higher risk of a future event (log rank test, P=0.0002) (FIG. 4). Cox hazard regression analysis revealed that low MT-COI was associated with increased risk of future event (OR: 4.89; 95% CI: 1.17-21) adjusting for adjusting for age, gender, smoking, LDL-cholesterol, HDL-cholesterol and triglycerides, BMI, BP, T2D, hs-CRP and IL-6 and number of stenosed arteries. There was only a weak correlation between MT-COI in exosomes and monocytes (R=0.24; P<0.05). Low MT-COI in monocytes (OR: 2.48; 95% CI: 1.06-5.86) was also related to new events in addition to low MT-COI in microvesicles and ex-smoking.

Example 5: Relation of MT-COI in Monocytes and Microvesicles with Regulatory Genes in Monocytes We also measured expressions of putative transcriptional regulators of COX such as nuclear receptor subfamily 2 group C member 2 (NR2C2), nuclear receptor subfamily 3 group C member 1 (NR3C1), nuclear respiratory factor (NRF)-1 and -2, peroxisome proliferator-activated receptor gamma, co-activator 1 alpha (PGC-1α), transcription factor 7 like 2 (TCF7L2), transcription factor A, mitochondrial (TFAM) and runt related transcription factor 2 (RUNX2). These potential regulators were identified using FrameWorker Analysis and ENCODE ChIP-seq analysis performed by Genomatix (Munich, Germany). The expressions of NRF1 (1.18±0.28 vs. 1.60±0.77; P<0.01), NR3C1 (1.01±1.44±0.88; P=0.01), RUNX2 (0.91±0.22 vs. 1.22±0.58; P<0.01) and TFAM (0.95±0.20 vs. 1.19±0.58) were lower in monocytes of CAD patients with a new event. Lower expression of NRF1 (R=0.37; P<0.01), NR3C1 (R=0.35; P<0.01), RUNX2 (R=0.46; P<0.001) and TFAM (R=0.62; P<0.001) correlated with lower MT-COI in monocytes. NRF1 correlated with RUNX2 (R=0.76; P<0.001), NR3C1 (R=0.90; P<0.001) and TFAM (R=0.48; P<0.001). NR3C1 also correlated with RUNX2 (R=0.78; P<0.001) and TFAM (0.51; P<0.001). RUNX2 and TFAM correlated with each other (R=0.51; P<0.001). Lower expression of NRF1 (R=0.34; P<0.01), NR3C1 (R=0.40; P<0.001), RUNX2 (R=0.34; P<0.01) and TFAM (R=0.26; P<0.05) correlated also with lower MT-COI in exosomes.

Example 6: Mouse Atherosclerosis and Gene Expressions in Aorta

Compared with C57BL6 control mice, LDL-R$^{-/-}$ mice had similar weight, and adiponectin, glucose, insulin, and triglyceride levels, and similar glucose tolerance and HOMA-IR. Their cholesterol levels were higher. The weight of ob/ob mice was higher than that of C57BL6 and LDL-R$^{-/-}$ mice; they also had higher glucose and higher HOMA-IR than C57BL6 and LDL-R$^{-/-}$ mice. Their glucose tolerance was higher than that of control mice. The weight of DKO mice was higher than that of C57BL6 and LDL-R$^{-/-}$ mice, and similar to that of ob/ob mice. They had lower adiponectin even compared to ob/ob mice. Glucose was higher and glucose tolerance lower compared to C57BL6 control and LDL-R$^{-/-}$ mice, but similar to these in ob/ob mice. DKO mice had the highest insulin, HOMA-IR, cholesterol and triglyceride levels (Table 4).

Age-matched C57BL6 and ob/ob mice had no detectable lesions. Plaque volumes in the aortic arch of DKO were 3.8-fold larger in LDL-R$^{-/-}$ mice. Whereas percentage of macrophages, lipids and SMC were similar, plaques in DKO mice contained more ox-LDL (Table 4). FIG. 5 shows representative sections.

Aortic Cox1 expressions were lower in the thoracic aorta of DKO mice than in that of the three other groups. LDL-R$^{-/-}$ mice had the highest Cox1 expressions. Cox4i1 was lower in ob/ob and tended to be lower in DKO mice than in control mice. Ob/ob mice had lower Cox4i1 than LDL-R$^{-/-}$ mice. Tfam was lower in ob/ob and in DKO mice than in control mice. Ob/ob mice had lower Tfam than LDL-R$^{-/-}$ mice (Table 4).

Compared to DKO placebo mice, diet restriction caused weight loss and decreased triglycerides. Fenofibrate treatment reduced HOMA-IR; weight and triglycerides were higher, and blood adiponectin lower in fenofibrate treated than in diet-restricted mice. Rosiglitazone treatment reduced weight, glucose, insulin, HOMA-IR, and increased glucose tolerance and adiponectin compared to placebo DKO mice. It also increased cholesterol. Compared with diet restricted mice rosiglitazone treated mice had higher weight, lower glucose, and higher glucose tolerance; their cholesterol was also higher. Compared to fenofibrate treated mice, rosiglitazone treated mice had lower glucose and higher glucose tolerance and adiponectin (Table 5).

Diet restriction reduced plaque volumes and percentage of ox-LDL. Fenofibrate treatment did not decrease plaque volume, and increased somewhat percentage of SMC compared to placebo DKO. Fenofibrate treated mice had higher plaque volume than diet restricted mice. Rosiglitazone tended to decrease plaque volume and significantly changed plaque composition. Percentage of macrophages was lower in rosiglitazone treated mice than in all other groups; SMC-to-macrophage ratio was higher in rosiglitazone treated mice than in placebo and diet restricted mice (Table 5).

Diet restriction and rosiglitazone treatment increased Cox1 in aorta. Cox1 in rosiglitazone treated mice was higher than in placebo and fenofibrate treated mice. Cox4i1 in diet restricted mice tended to be higher; expression was no more different from that in wild-type C57BL6 mice. Rosiglitazone treatment increased, more than weight restriction and fenofibrate treatment Cox4i1. Only rosiglitazone increased Tfam (Table 5). Cox1 and Cox4i1 were highly correlated ($R_s$=0.65; P<0.001), and both correlated with adiponectin ($R_s$=0.59, and 0.52, respectively; P<0.001 for both). They also correlated with Tfam ($R_s$=0.86 and 0.75, respectively, P<0.001 for both); Tfam also correlated with adiponectin (R=0.58; P<0.001). Cox1 was inversely related to plaque ox-LDL ($R_s$=−0.40; P<0.01) and plaque macrophages ($R_s$=−0.38; P<0.05). Cox4i1 and Tfam were also inversely related to plaque macrophages ($R_s$=−0.50; P<0.001 and $R_s$=−0.43; P<0.01).

Interestingly, increased number of macrophages and higher levels of lipids, of which ox-LDL is the most important, are measures of plaque instability. These mechanistic data in mice further support the relation between COX1, COX4I1 and TFAM expressions and cardiovascular events depending on plaque instability.

Figure 6:
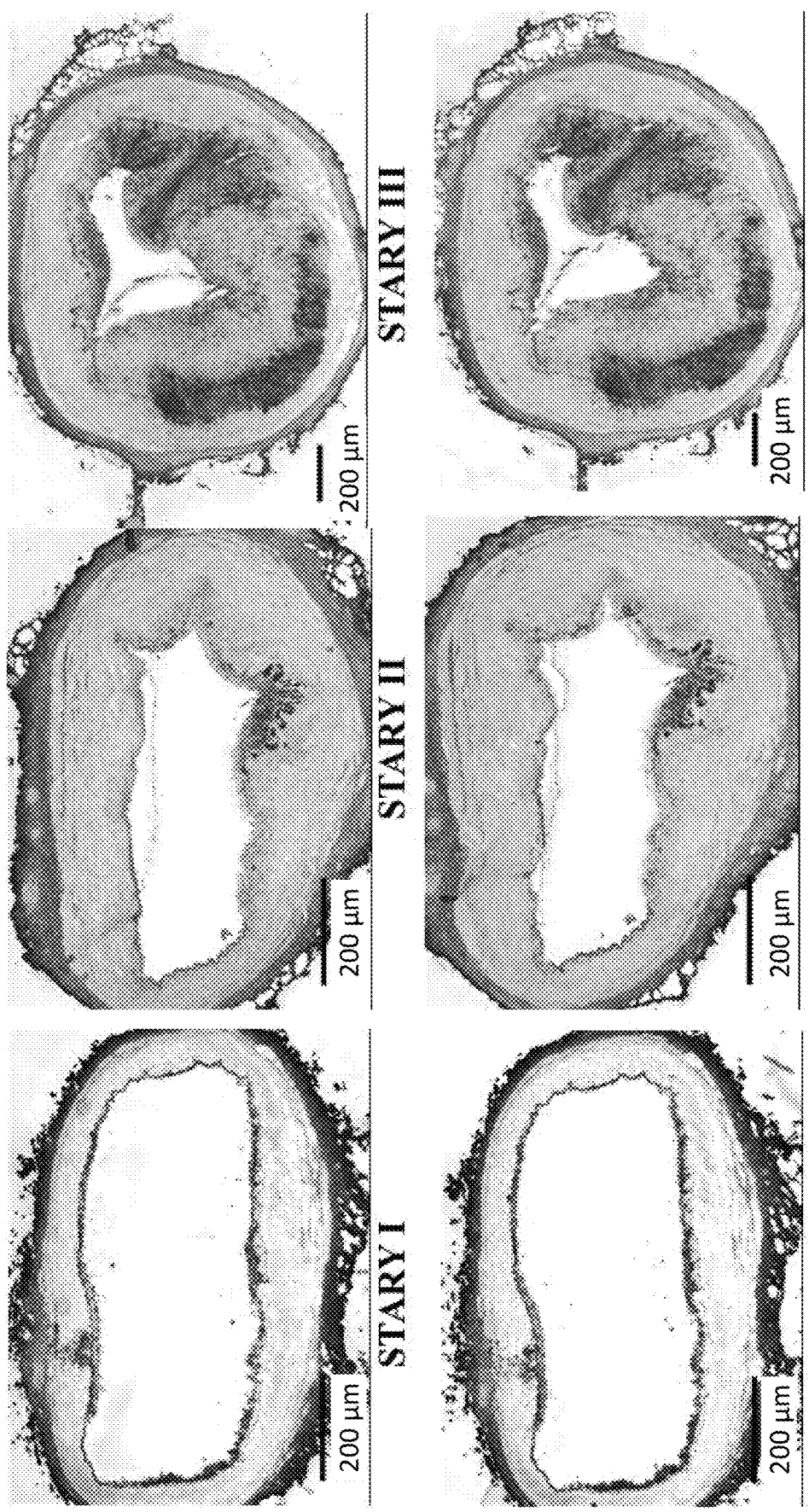
FIG. 6: Atherosclerotic plaques in coronary arteries of high-fat diet-fed miniature pigs: representative sections of Stary I, Stary II and Stary III atherosclerotic plaques in coronary arteries of pigs. Macrophages are stained with anti-CD18 antibody; ox-LDL is stained with mAb4E6.
Figure 7:
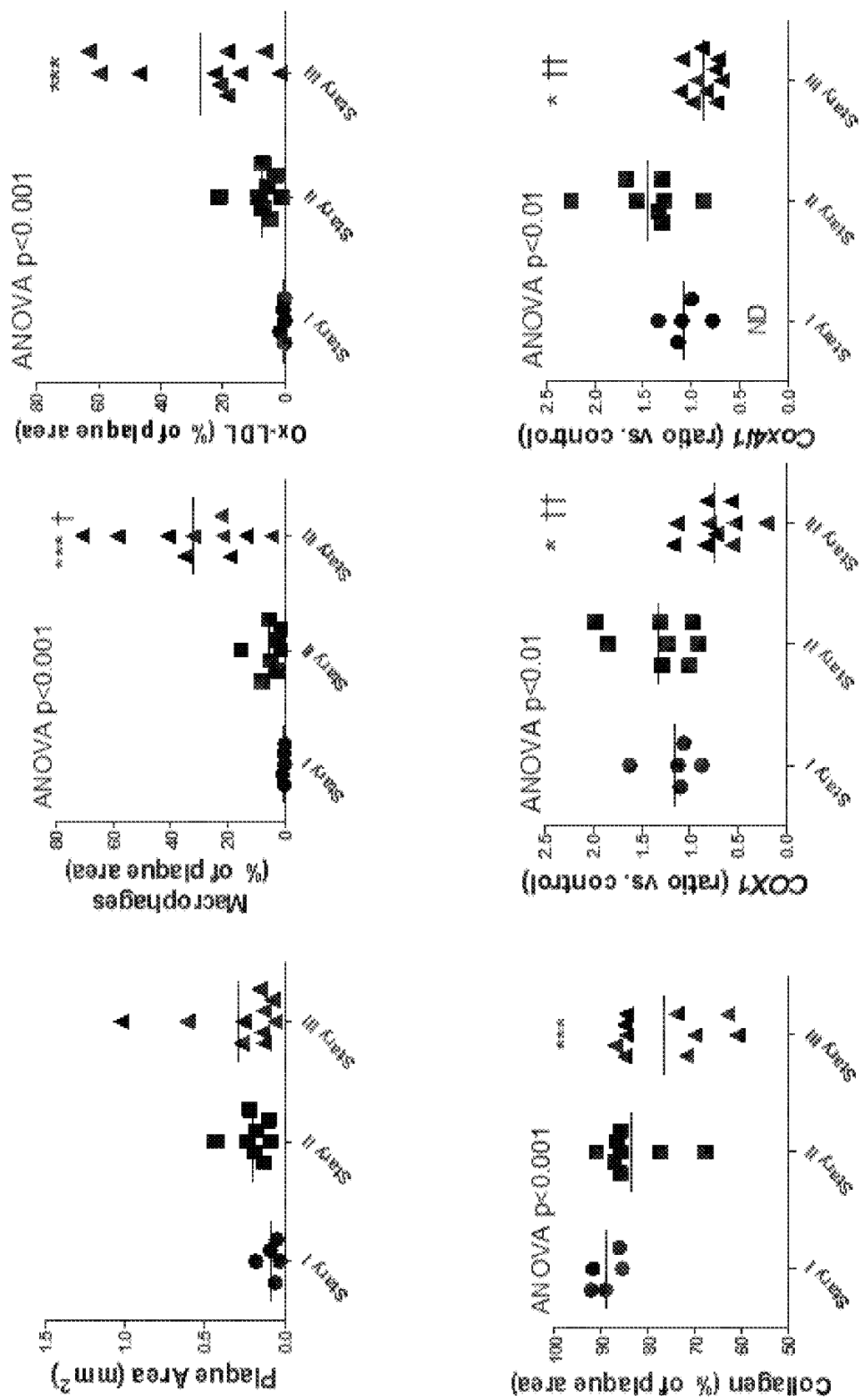
FIG. 7: Atherosclerosis in coronary arteries of miniature pigs and gene expressions in their macrophages: Scatter plots show coronary plaque area, percentages of macrophages, ox-LDL, and collagen, and COX1 and COX4I1 gene expressions in coronary artery macrophages in Stary I (n=5), Stary II (n=13) and Stary III (n=12) miniature pigs. *P<0.05, ***P<0.001 compared to Stary I; †P<0.05, ††p<0.01 compared to Stary II. Gene expression data are ratios compared to expressions in coronary artery tissue extracts of 16 control pigs without atherosclerosis.

Example 7: Atherosclerosis in Miniature Pigs and Gene Expressions in Isolated Macrophages We studied coronary atherosclerosis in high-fat diet-fed miniature pigs, and measured gene expressions in coronary plaque macrophages isolated by laser capture. Diet pigs were categorized in 3 groups according the characteristics of their coronary atherosclerotic plaques using the Stary classification. Table 6 shows that age, weight, plasma leptin, adiponectin, glucose, triglycerides, LDL-cholesterol, HDL-cholesterol, hs-CRP and ox-LDL were similar in 3 groups of diet-fed pigs. However, pigs with Stary III lesions had higher insulin levels and higher HOMA-IR. FIG. 6 shows representative sections of stage I, stage II and stage III. FIG. 7 shows that coronary plaque sizes were not different in pigs with stage I, or stage II or stage III atherosclerosis. However, stage III plaques contained more macrophages, ox-LDL, and less collagen, indicative for more unstable plaques. Interestingly, expression of COX1 and COX4I1 was lower in stage III coronary plaques. TFAM was also lower (0.96±0.17 in Stage I, 1.13±0.36 in stage II, and 0.63±0.29 in stage III (ANOVA P<0.01). COX1 (Rs=−0.46; P<0.05) and TFAM (Rs=−0.53; P<0.01), but not COX4I1, were inversely related to plaque ox-LDL. Both COX1 (Rs=0.72; P<0.001) and COX4I1 (Rs=0.52; P<0.01) correlated with TFAM. COX1 (Rs=−0.70; P<0.001) and TFAM (Rs=−0.56; P<0.01), but not COX4I1, were inversely related to HOMA-IR.

Materials and Methods

Materials

All chemicals were obtained from Sigma-Aldrich unless stated otherwise.

Patients

The patient cohort comprised 95 patients undergoing coronary angiography: 79 were found to have stenosed arteries (cases); 16 others did not (controls). This study complies with the Declaration of Helsinki and the Medical Ethics Committee of the KU Leuven approved the study protocol. All human participants gave written informed consent.

Monocyte Isolation

Blood samples were collected, and peripheral blood mononuclear cells (PBMCs) were prepared from the anticoagulated blood using gradient separation on Histopaque-1077 after removal of the plasma fraction. Cells were washed three times in $Ca^{2+}$- and $Mg^{2+}$-free Dulbecco's (D)-PBS. PBMCs were incubated for 15 minutes at 4° C. with CD14 microbeads at 20 µl/1×$10^7$ cells. The cells were washed once, re-suspended in 500 µl $Ca^{2+}$- and $Mg^{2+}$-free DPBS containing 0.5% BSA/1×$10^8$ cells. The suspension was then applied to an LS column in a MidiMACS Separator (Miltenyi) (66, 67). We selected $CD14^+$ monocytes because CD14 intensity expression on circulating monocytes was found to be associated with increased inflammation in patients with T2DM (68).

Blood Analysis

Blood samples were centrifuged to prepare plasma samples for analysis. Total and HDL-cholesterol and triglyceride levels were determined with enzymatic methods (Boehringer Mannheim). LDL-cholesterol levels were calculated with the Friedewald formula. Plasma glucose was measured with the glucose oxidase method (on Vitros 750XRC, Johnson & Johnson), and insulin with an immunoassay (Biosource Technologies). Ox-LDL (69) and IL-6 were measured with enzyme-linked immuno sorbent assay (Mercodia and R&D Systems). Hs-CRP (Beckman Coulter) was measured on an Image 800 Immunochemistry System. Blood pressure was taken three times with the participant in a seated position after 5 minutes quiet rest. The average of the last two measurements was used for systolic and diastolic blood pressure.

(Micro)RNA Isolation, Microarray and Quantitative Real-Time PCR Analysis

Total RNA from monocytes, macrophages and vascular tissues was extracted with TRIzol reagent (Invitrogen) and purified on (mi)RNeasy Mini Kit columns (Qiagen). RNA concentration and quality were assessed with the NanoDrop 2000 (Thermo Scientific), and RNA integrity was determined with the RNA 6000 Nano assay kit using the Agilent 2100 Bioanalyzer.

For a series of 19 samples RNA was isolated from micovesicles using the miRNeasy serum/plasma kit (Qiagen) following the manufacturer instructions. cDNA synthesis was performed using the iScript Advanced cDNA Synthesis Kit (Bio-Rad) with 15 µl of total RNA. The cDNA quality of each sample was assessed by means of two human universally expressed genes. The RNA concentration was determined using the NanoDrop 2000 UV-Vis spectrophotometer (Thermo Scientific) (performed by Biogazelle, Gent, Belgium).

qPCR analysis is a commonly used validation tool for confirming gene expression results obtained from microarray analysis. First-strand cDNA was generated from total RNA with the SuperScript VILO cDNA synthesis kit (Invitrogen). qPCR analysis was performed on a 7500 Fast Real-Time PCR system using Fast SYBRGreen master mix, according to the supplier protocols (Applied Biosystems). Oligonucleotides (Invitrogen) used as forward and reverse primers were designed using the "Primer Express" software (Applied Biosystems) and are summarized in Table 7. RNA expression levels were calculated with the delta-delta-quantification cycle method ($\Delta\Delta C_q$) described by Livak and Schmittgen (70). For each RNA and microRNA sample, the expression levels of the RNAs as described herein were compared and normalized to reference housekeeping RNAs or microRNAs. The $C_q$ values for the gene of interest and the most stable housekeeping genes were determined for each sample to calculate $\Delta C_{q,sample}$ ($C_{q,\ gene\ of\ interest}$−mean $C_{q,housekeeping\ genes}$), thus normalizing the data and correcting for differences in amount among RNA samples. In detail, HPRT1 (hypoxanthine phosphoribosyltransferase), SDHA (succinate dehydrogenase complex, subunit A), TBP (TATA box binding protein) and YWHAZ (tyrosine 3-monooxygenase/tryptophan 5-monooxygenase activation protein, zeta) were used when measuring RNA in human monocyte samples. They were selected as most stable housekeeping genes using GeNorm (71). Reference RNAs in microvesicle samples were B2M (beta-2-microglobulin), GAPDH (glyceraldehyde-3-phosphate dehydrogenase), PPIA (peptidylprolyl isomerase A), RPL13A (RPS18 (ribosomal protein L13a), ribosomal protein S18) and YWHAZ (tyrosine 3-monooxygenase/tryptophan 5-monooxygenase activation protein, zeta). Reference microRNAs were miR-15b, miR-106b and miR-574-3p. (Micro)RNA analysis was also performed using TaqMan microRNA assays from Life Technologies by Biogazelle (Gent, Belgium), a service provider, to validate our data.

Frame Worker analysis to get insight in transcriptional regulation was performed by Genomatix (München, Germany).

Animal Experiments

Mice

Animal experiments conformed to the Guide for the Care and Use of Laboratory Animals published by the US National Institutes of Health (NIH Publication No. 85-23, revised 1996). They were approved by the Institutional Animal Care and Research Advisory Committee of the KU Leuven (Permit Number: P087/2007). Breeding and genotyping of LDL-receptor deficient, leptin-deficient ob/ob, and DKO (LDL-R$^{-/-}$×ob/ob) mice, on the C57BL/6J background, were performed as previously described (72, 73).

In the first, we compared age-matched (24 weeks) C57BL/6J control mice (n=10), with LDL-receptor deficient (LDL-R$^{-/-}$, n=10), leptin-deficient ob/ob (n=10), and DKO mice (n=13). In the second study, DKO mice were compared with diet-restricted mice (n=8; food intake of was restricted to 2.5 g/d for 12 weeks between 12 and 24 weeks) of age, and with DKO mice treated with fenofibrate (n=12, rosiglitazone (n=12) for 12 weeks starting at the age of 12 weeks. We compared them with non-treated DKO at 24 weeks. Fenofibrate and rosiglitazone (Avandia) were purchased from Sigma-Aldrich and GlaxoSmithKline. Fenofibrate (50 mg kg$^{1}$ day$^{-1}$) and rosiglitazone (10 mg kg$^{-1}$ day$^{-1}$) were added to standard diet (SD) containing 4% fat (Ssniff), placebo-treated mice received the grinded chow only. Food and water were available ad libitum. Food intake of the DKO mice was ≈5.7 g/day and was not affected by the treatments. Food intake of lean mice was about 50% of that of DKO mice. After an overnight fast, blood was collected by puncturing the vena cava. Plasma was obtained by centrifugation. Total cholesterol and triglycerides were measured using standard enzymatic colorimetric assays (Boehringer Mannheim). Glucose was measured with a glucometer (Menarini Diagnostics) and plasma insulin with a mouse insulin enzyme-linked immunosorbant assay (ELISA) (Mercodia). To convert from mg/dL to mM, we divided glucose by 18 (=molecular weight), triglycerides by 89 and total cholesterol by 39. Insulin resistance was calculated by a homeostasis model assessment of insulin resistance (HOMA-IR)=fasting plasma insulin (mU/L)×fasting blood glucose (mM)/22.5. To determine glucose tolerance, glucose was measured in samples obtained by tail bleeding before and 15, 30, 60, 120 and 240 minutes after intraperitoneal administration of glucose (20% glucose solution; 2 g/kg). Plasma adiponectin L6 were measured with specific mouse ELISA (R&D Systems). At baseline (12 weeks) characteristics of mice treated with placebo, fenofibrate and rosiglitazone were identical. All mice were sacrificed by Nembutal overdose at the age of 24 weeks (72, 73).

The extent of atherosclerosis was determined by analysis of ten 7-μm cross-sections of the aortic valves of DKO mice. Lipids were stained with oil-red O, oxidized LDL with mAb4E6, smooth muscle cells with a α-actin-specific antibody (Dako), and macrophages with an antibody against mouse Mac-3 antigen (Pharmingen). Blinded analysis of positive immunostained sections was performed with the Quantimet600 image analyzer (Leica). A color intensity threshold mask for immunostaining was defined to detect the red color by sampling, and the same threshold was applied to all specimens. The percentage of the total area with positive color for each section was recorded (72, 74).

Miniature Pigs

Miniature pigs were bred and maintained as described previously (82, 83). Pigs (n=23) were fed an atherogenic diet, containing 4% cholesterol, 14% beef tallow, and 2% hog bile, administered at an amount of 1 kg/d starting at a mean age of 18 weeks: 9 for 6 weeks; 5 for 12 weeks, and 3 for 24 weeks and 6 for 36 weeks. The extent of atherosclerosis was determined by analysis of 18 cross-sections, spanning a 3-mm segment, of the proximal left anterior descending artery (LAD). Sections were analyzed using the Leica Quantimet 600 (Leica). Macrophages were stained with an anti-CD18 antibody, oxLDL with 4E6, smooth muscle cells (SMCs) with an anti-α-SM actin monoclonal antibody, and collagen with Sirius red. (82, 83) Macrophages (&1000 cells) were microdissected from between 20 and 100 sections spanning a 3-mm proximal segment of the LAD with a PixCell II LCM system using Capture HS LCM caps (Arcturus Engineering) as described in the detailed online protocol (available online at http://atvb.ahajournals.org). Macrophages were identified on the basis of histological appearance and polyploidy. The adjacent sections were used for plaque phenotyping (84) according to the Stary classification. Type I lesions represent the very initial changes and are recognized as an increase in the number of intimal macrophages and the appearance of macrophages filled with lipid droplets (foam cells). Type II lesions include fatty streak lesions, the first grossly visible lesions, and are characterized by layers of macrophage foam cells and lipid droplets within intimal smooth muscle cells and minimal coarse-grained particles and heterogeneous droplets of extracellular lipid. Type III (intermediate) lesions are the morphological and chemical bridge between type II and advanced lesions. They are characterized by pools of extracellular lipid in addition to all the components of type II lesions (84, 85).

Statistical Analysis

Two groups of patients were compared with an unpaired Mann-Whitney test. More than two groups of mice or pigs were compared with Kruskal-Wallis nonparametric ANOVA followed by Dunn's comparison (GraphPad Prism 5). Categorical data were compared by Fisher's exact test. Receiver Operating Characteristic (ROC) curve, Kaplan-Meier and Cox proportional hazards regression analysis was performed with MedCalc statistical software for biomedical research. Stepwise multiple regression analysis was performed with the Statistical Package for the Social Sciences (SPSS for Windows; release 22). A P-value of less than 0.05 was considered statistically significant. A P-value of less than 0.05 was considered statistically significant.

Tables

TABLE 1

Characteristics of controls and cardiovascular disease patients

| | Controls (n = 16) | Cases (n = 71) |
|---|---|---|
| A. Characteristics | | |
| Diseased vessels (1, 2, 3; %) | — | 20/42/38 |
| History of ischemia (%) | — | 44 |
| History of stable angina (%) | — | 68 |

TABLE 1-continued

Characteristics of controls and cardiovascular disease patients

|  | Controls (n = 16) | Cases (n = 71) |
|---|---|---|
| History of unstable angina (%) | — | 29 |
| Age (years) | 54 ± 8.7 | 56 ± 7.3 |
| Gender (% male) | 50 | 76*** |
| Smoker (%) | 6.3 | 35** |
| Ex-smoker (%) | 19 | 39** |
| T2DM (%) | 12 | 15 |
| MetS (%) | 25 | 38 |
| Statin use (%) | 31 | 64*** |
| Antihypertensive drug use (%) | 44 | 62* |
| ACEI or ARB (%) | 19 | 32 |
| CACB (%) | 19 | 16 |
| Betablocker (%) | 31 | 62*** |
| Oral antidiabetic drug use (%) | 6.3 | 14 |
| Metformin (n, %) | 6.3 | 8.5 |
| Insulin therapy (%) | 6.3 | 4.3 |
| BMI (kg/m$^2$) | 28 ± 4.3 | 26 ± 2.7 |
| Leptin (ng/ml) | 16 ± 6.3 | 9.9 ± 5.6 |
| ADN (μg/ml) | 11 ± 6.3 | 9.3 ± 5.6 |
| Glucose (mg/dl) | 123 ± 56 | 116 ± 45 |
| Insulin (mU/l) | 29 ± 53 | 27 ± 37 |
| HOMA-IR | 5.5 ± 12 | 4.3 ± 7.0 |
| TG (mg/dl) | 128 ± 67 | 130 ± 67 |
| LDL-C (mg/dl) | 101 ± 37 | 94 ± 37 |
| HDL-C (mg/dl) | 64 ± 19 | 47 ± 13** |
| SBP (mmHg) | 142 ± 18 | 142 ± 19 |
| DBP (mmHg) | 75 ± 6.8 | 80 ± 12* |
| IL-6 (pg/ml) | 2.6 ± 1.2 | 3.8 ± 3.2* |
| Hs-CRP (mg/l) | 1.5 ± 1.4 | 2.6 ± 2.4* |
| Ox-LDL (IU/l) | 54 ± 22 | 49 ± 20 |
| B. Gene expressions | | |
| COX1 | 1.16 ± 0.24 | 1.03 ± 0.26 (P = 0.07) |
| COX4I1 | 1.16 ± 0.17 | 1.03 ± 0.13** |
| RUNX2 | 1.09 ± 0.16 | 0.93 ± 0.13** |
| TFAM | 1.16 ± 0.21 | 0.96 ± 0.18** |
| microRNA | | |
| miR-26a | 1.18 ± 0.11 | 1.02 ± 0.14*** |
| miR-30b | 1.16 ± 0.13 | 0.97 ± 0.14*** |
| miR-361 | 1.14 ± 0.13 | 0.97 ± 0.14*** |

Data shown are means ± SD.
*P < 0.05,
**P < 0.01 and
***P < 0.001 patients compared with controls.
Abbreviations: ACEI, ACE inhibitor; ADN, adiponectin; ARB, Angiotensin Receptor blocker; BMI, body mass index; CACB, Calcium Channel blocker; C, cholesterol; DBP, diastolic blood pressure; HOMA-IR, homeostasis model assessment of insulin resistance; hs-CRP, high sensitivity C-reactive protein; IL, interleukin; MetS, metabolic syndrome; ox-LDL, oxidized LDL; SBP, systolic blood pressure; T2DM, type 2 diabetes mellitus; TG, triglycerides.

TABLE 2

Relation with coronary stenosis

| Gene | AUC | OR | Sensitivity (%) | Specificity (%) |
|---|---|---|---|---|
| RNA | | | | |
| COX1 | 0.64 (0.53-0.74) | 6.08 (1.3-28) | 46 (34-59) | 88 (62-98) |
| COX4I1 | 0.72 (0.62-0.81) | 4.7 (1.4-16) | 61 (49-72) | 75 (48-93) |
| TFAM | 0.77 (0.67-0.81) | 6.5 (2.0-21) | 76 (64-84) | 69 (41-89) |
| RUNX2 | 0.68 (0.57-0.77) | 8.1 (1.8-39) | 54 (42-66) | 88 (62-98) |
| COX1 & COX4I1 | ND | 7.4 (1.5-36) | 55 (40-69) | 86 (57-98) |
| COX1 & TFAM | ND | 28 (301-249) | 74 (56-87) | 91 (59-100) |
| COX1 & RUNX2 | ND | 11 (1.3-94) | 50 (33-67) | 92 (62-100) |
| COX4I1&TFAM (0 vs. 2) | ND | 14 (2.7-75) | 76 (62-87) | 82 (48-98) |
| COX4I1&RUNX2 (0 vs. 2) | ND | 22 (2.6-180) | 61 (45-75) | 93 (68-100) |
| TFAM&RUNX2 (0 vs. 2) | ND | 20 (2.3-175) | 71 (56-83) | 89 (52-100) |
| microRNA | | | | |
| mir-26a | 0.82 (0.72-0.90) | 17 (3.3-85) | 77 (66-86) | 83 (52-98) |
| mirR-30b | 0.86 (0.77-0.93) | 24 (4.7-124) | 83 (72-91) | 83 (52-98) |
| RNA & microRNA | | | | |
| miR-26a & COX1 | ND | 23 (2.6-203) | 72 (55-85) | 90 (56-100) |
| miR-26a & COX4I1 | ND | 25 (2.8-229) | 78 (64-89) | 88 (47-100) |
| miR-26a & TFAM | ND | 23 (2.6-202) | 72 (55-85) | 90 (56-100) |
| miR-30b & COX1 | ND | 18 (3.2-100) | 78 (62-90) | 83 (52-98) |
| miR-30b & COX4I1 | ND | 24 (4.1-141) | 86 (71-95) | 80 (44-97) |
| miR-30b & TFAM | ND | 117 (10-1275) | 94 (82-99) | 89 (52-100) |

Values are AUC determined by ROC analysis, and OR, sensitivity and specificity determined with two-sided Fisher's exact test; 95% confidence intervals in parentheses. Cut-off value, determined by ROC analysis, is 1.054 for COX4I1, 0.918 for RUNX2, 1.080 for TFAM, 1.12 for miR-26a and 1.06 for mir-30b.
Abbreviations: AUC, area under the curve; OR, odds ratio.

TABLE 3

Characteristics and gene expressions of patients with coronary artery stenosis without and with new cardiovascular events

|  | No new event (n = 26) | New event (n = 37) |
|---|---|---|
| A. Characteristics | | |
| Follow-up (d) | 1262 ± 43 | 1521 ± 33 |
| Diseased vessels (1, 2, 3, %) | 19, 46, 35 | 28, 37, 35 |
| History of ischemia (%) | 44 | 43 |
| History of stable angina (%) | 64 | 70 |
| History of unstable angina (%) | 28 | 30 |
| Age (years) | 57 ± 7.5 | 57 ± 7.6 |
| Gender (n, % male) | 65 | 81* |
| Smoker (n, %) | 38 | 41 |
| Ex-smoker (n, %) | 35 | 46* |
| T2DM (n, %) | 19 | 16 |
| MetS (n, %) | 46 | 32 |
| Statin use (n, %) | 56 | 68 |
| Antihypertensive drug use (n, %) | 72 | 59 |
| ACEI or ARB (n, %) | 24 | 35 |
| CACB (n, %) | 20 | 19 |
| Betablocker (n, %) | 72 | 49 |
| Oral antidiabetic drug use (n, %) | 20 | 14 |
| Metformin (n, %) | 12 | 8.1 |
| Insulin therapy (n, %) | 8.3 | 2.7 |
| BMI (kg/m$^2$) | 26 ± 2.4 | 26 ± 3.0 |
| Leptin (ng/ml) | 9.9 ± 12 | 9.4 ± 8.7 |
| ADN (μg/ml) | 8.7 ± 5.3 | 10 ± 6.1 |
| Glucose (mg/dl) | 114 ± 52 | 118 ± 44 |
| Insulin (mU/l) | 21 ± 26 | 25 ± 36 |
| HOMA-IR | 6.2 ± 4.0 | 4.0 ± 4.0 |
| TG (mg/dl) | 142 ± 78 | 123 ± 66 |
| LDL-C (mg/dl) | 90 ± 33 | 95 ± 39 |
| HDL-C (mg/dl) | 45 ± 11 | 48 ± 14 |
| SBP (mmHg) | 142 ± 17 | 144 ± 19 |
| DBP (mmHg) | 79 ± 12 | 82 ± 12 |
| IL-6 (pg/ml) | 3.8 ± 2.6 | 3.3 ± 2.0 |
| Hs-CRP (mg/l) | 4.7 ± 6.1 | 3.0 ± 3.1 |
| Ox-LDL (IU/l) | 47 ± 18 | 49 ± 21 |
| B. Gene expressions | | |
| COX1 | 1.11 ± 0.23 | 0.95 ± 0.27** |
| COX4I1 | 1.03 ± 0.157 | 1.03 ± 0.13 |
| RUNX2 | 0.94 ± 0.22 | 0.92 ± 0.21 |
| TFAM | 0.96 ± 0.16 | 0.96 ± 019 |
| microRNA | | |
| miR-26a | 1.02 ± 0.14 | 0.99 ± 0.17 |
| miR-30b | 1.00 ± 0.13 | 0.93 ± 0.19 |
| miR-361 | 1.01 ± 0.13 | 0.96 ± 0.16 |

Data shown are means ± SD.
*P < 0.05, and
**P < 0.01 patients with compared with patients with cardiovascular events.
Abbreviations: ACEI, ACE inhibitor; ADN, adiponectin; ARB, Angiotensin Receptor blocker; BMI, body mass index; CACB, Calcium Channel blocker; C, cholesterol; DBP, diastolic blood pressure; HOMA-IR, homeostasis model assessment of insulin resistance; hs-CRP, high sensitivity C-reactive protein; IL, interleukin; MetS, metabolic syndrome; ox-LDL, oxidized LDL; SBP, systolic blood pressure; T2DM, type 2 diabetes mellitus; TG, triglycerides.

TABLE 4

Blood variables, atherosclerosis and gene expression in aorta

|  | C57BL/6J (n = 10) | LDL-R$^{(-/-)}$ (n = 10) | Ob/Ob (n = 10) | DKO (n = 12) | ANOVA |
|---|---|---|---|---|---|
| A. Weight and blood variables | | | | | |
| Weight (g) | 28 ± 3.4 | 25 ± 5.0 | 68 ± 3.5***/$$$ | 63 ± 3.3*/$$ | P < 0.001 |
| ADN (μg/ml) | 5.1 ± 1.8 | 4.1 ± 1.0 | 4.7 ± 0.9 | 2.8 ± 1.7**/£ | P < 0.01 |
| Glucose (mg/dl) | 76 ± 12 | 81 ± 10 | 117 ± 24**/$$ | 127 ± 30***/$$ | P < 0.001 |
| AUC of IPGTT (×10$^3$) | 35 ± 15 | 44 ± 12* | 56 ± 12* | 84 ± 25*/$$ | P < 0.001 |
| Insulin (mU/L) | 72 ± 15 | 51 ± 17 | 94 ± 60 | 176 ± 77**/$$$/£ | P < 0.001 |
| HOMA-IR | 14 ± 3.5 | 9.6 ± 3.1 | 27 ± 16*/$$ | 63 ± 41***/$$$/££ | P < 0.001 |
| Total C (mg/dl) | 54 ± 13 | 156 ± 43* | 63 ± 22 | 467 ± 89***/£££ | P < 0.001 |
| TG (mg/dl) | 43 ± 16 | 41 ± 19 | 28 ± 4.9 | 196 ± 45***/$$$/£££ | P < 0.001 |
| B. Atherosclerosis | | | | | |
| Plaque volume* | ND | 23 ± 16 | ND | 87 ± 22$$$ | — |
| MQ (%) | ND | 21 ± 10 | ND | 28 ± 11 | — |
| Lipids (%) | ND | 24 ± 3.3 | ND | 29 ± 6.2 | — |
| Ox-LDL (%) | ND | 5.0 ± 2.9 | ND | 12 ± 5.0$$$ | — |
| SMC (%) | ND | 4.5 ± 5.1 | ND | 8.2 ± 6.2 | — |
| SMC/MQ | ND | 0.30 ± 0.36 | ND | 0.38 ± 0.30 | — |

TABLE 4-continued

Blood variables, atherosclerosis and gene expression in aorta

| | C57BL/6J (n = 10) | LDL-R$^{(-/-)}$ (n = 10) | Ob/Ob (n = 10) | DKO (n = 12) | ANOVA |
|---|---|---|---|---|---|
| C. Gene expressions in aorta | | | | | |
| Cox1 | 1.05 ± 0.36 | 2.63 ± 1.23 | 1.07 ± 0.27$^{\$\$}$ | 0.52 ± 0.18*/$^{\$\$\$/£}$ | P < 0.001 |
| Cox4i1 | 1.05 ± 0.35 | 1.12 ± 0.53 | 0.47 ± 0.14***/$^{\$\$}$ | 0.64 ± 0.16 | P < 0.001 |
| Tfam | 1.02 ± 0.21 | 1.04 ± 0.45 | 0.44 ± 0.13***/$^{\$\$}$ | 0.63 ± 0.16 | P < 0.001 |

Data shown are means ± SD.
*P < 0.05,
**P < 0.01 and
***P < 0.001 compared with C57BL/6J;
$^{\$}$P < 0.05,
$^{\$\$}$P < 0.01 and
$^{\$\$\$}$P < 0.001 compared with LDLR$^{(-/-)}$;
$^{£}$P < 0.05,
$^{££}$P < 0.01 and
$^{£££}$P < 0.001 compared with ob/ob.
Abbreviations: ADN: adiponectin; AUC: area under curve; C: cholesterol; HOMA-IR, homeostasis model assessment of insulin resistance; IPGTT: intraperitoneal glucose tolerance test; MQ: SMC: smooth muscle cells; TG: triglyceride.
*Total plaque volumes were expressed in ×10$^{-3}$ μm$^3$.
ND: detectable. Because C57BL6 and ob/ob mice did not have atherosclerotic plaques;
ANOVA was not performed

TABLE 5

Blood variables, atherosclerosis and gene expression in aorta of DKO mice

| | DKO Placebo (n = 12) | DKO Diet restricted (n = 8) | DKO Fenofibrate (n = 12) | DKO Rosiglitazone (n = 12) | ANOVA |
|---|---|---|---|---|---|
| A. Weight and blood variables | | | | | |
| Weight (g) | 63 ± 3.3 | 35 ± 5.2*** | 59 ± 4.0$^{\$\$}$ | 55 ± 3.6*/$^{\$}$ | P < 0.001 |
| ADN (μg/ml) | 2.8 ± 1.7 | 5.8 ± 1.4 | 1.1 ± 0.6$^{\$\$}$ | 16 ± 2.3***/$^{£££}$ | P < 0.001 |
| Glucose (mg/dl) | 127 ± 30 | 136 ± 50 | 127 ± 30 | 88 ± 18*/$^{\$/£}$ | P < 0.001 |
| AUC of IPGTT (×10$^3$) | 84 ± 25 | 83 ± 27 | 75 ± 15 | 50 ± 3.5**/$^{\$\$/£}$ | P < 0.001 |
| Insulin (mU/L) | 176 ± 77 | 97 ± 52 | 104 ± 19 | 69 ± 42** | P < 0.01 |
| HOMA-IR | 56 ± 33 | 34 ± 25 | 31 ± 7.4* | 16 ± 11** | P < 0.01 |
| Total C (mg/dl) | 467 ± 89 | 389 ± 68 | 533 ± 129 | 700 ± 139*/$^{\$\$}$ | P < 0.001 |
| TG (mg/dl) | 196 ± 45 | 106 ± 46** | 212 ± 97$^{\$}$ | 192 ± 96 | P < 0.01 |
| B. Atherosclerosis | | | | | |
| Plaque volume* | 87 ± 22 | 34 ± 8.3** | 115 ± 35$^{\$\$\$}$ | 50 ± 41$^{££}$ | P < 0.001 |
| MQ (%) | 28 ± 11 | 22 ± 5.4 | 22 ± 4.1 | 12 ± 3.6***/$^{\$/££}$ | P < 0.001 |
| Lipids (%) | 29 ± 6.2 | 29 ± 6.1 | 28 ± 4.3 | 25 ± 3.6 | NS |
| Ox-LDL (%) | 12 ± 5.0 | 3.8 ± 0.8*** | 8.1 ± 3.4$^{\$}$ | 7.0 ± 4.1 | P < 0.05 |
| SMC (%) | 8.2 ± 6.2 | 9.0 ± 2.1 | 13 ± 4.2* | 13 ± 4.0* | P < 0.05 |
| SMC/MQ | 0.38 ± 0.30 | 0.40 ± 0.16 | 0.57 ± 0.16 | 0.97 ± 0.28***/$^{\$\$\$}$ | P < 0.001 |
| C. Gene expressions aorta | | | | | |
| Cox1 | 0.52 ± 0.18 | 0.98 ± 0.46*/ | 0.47 ± 0.11$^{\$\$}$ | 1.16 ± 0.40***/$^{\$/£££}$ | P < 0.001 |
| Cox4i1 | 0.64 ± 0.17 | 1.03 ± 0.64 | 0.67 ± 0.14 | 2.20 ± 0.64**/$^{\$\$/££}$ | P < 0.001 |
| Tfam | 0.63 ± 0.16 | 0.74 ± 0.15 | 0.65 ± 0.09 | 1.57 ± 0.50***/$^{\$/££}$ | P < 0.001 |

Data shown are means ± SD.
*P < 0.05,
**P < 0.01 and
***P < 0.001 compared with C57BL/6J;
$^{\$}$P < 0.05,
$^{\$\$}$P < 0.01 and
$^{\$\$\$}$P < 0.001 compared with DKO after weight loss;
$^{£}$P < 0.05,
$^{££}$P < 0.01, and
$^{£££}$P < 0.001 treated with Fenofibrate.
Abbreviations: ADN: adiponectin; AUC: area under curve; C: cholesterol; HOMA-IR, homeostasis model assessment of insulin resistance; IPGTT: intraperitoneal glucose tolerance test; MQ: SMC: smooth muscle cells; TG: triglyceride.
*Total plaque volumes were expressed in ×10$^{-3}$ μm$^3$.

TABLE 6

Characteristics of control and diet pigs, according to stage of coronary atherosclerosis

| A. Characteristics | Stary I (n = 5) | Stary II (n = 8) | Stary III (n = 10) | ANOVA |
|---|---|---|---|---|
| Age at start (weeks) | 20 ± 8 | 18 ± 7 | 20 ± 10 | NS |
| Age at end (weeks) | 38 ± 18 | 38 ± 6 | 35 ± 6 | NS |
| Gender (% male) | 50 | 25 | 50 | NS |
| Weight at start (kg) | 23 ± 6 | 22 ± 6 | 24 ± 8 | NS |
| Weight at end (kg) | 63 ± 42 | 60 ± 30 | 54 ± 24 | NS |
| Leptin (ng/ml) | 12 ± 5.1 | 12 ± 13 | 8.2 ± 5.6 | NS |
| ADN (μg/ml) | 10 ± 4.4 | 10 ± 4.5 | 10 ± 5.2 | NS |
| Glucose (mg/dl) | 112 ± 51 | 127 ± 47 | 129 ± 55 | NS |
| Insulin (μg/l) | 0.10 ± 0.07 | 0.10 ± 0.04 | 0.22 ± 0.09*/† | <0.05 |
| HOMA-IR | 0.31 ± 0.25 | 0.34 ± 0.16 | 0.77 ± 0.43† | <0.05 |
| TG (mg/dl) | 116 ± 106 | 95 ± 71 | 83 ± 59 | NS |
| LDL-C (mg/dl) | 307 ± 216 | 421 ± 213 | 425 ± 165 | NS |
| HDL-C (mg/dl) | 166 ± 120 | 114 ± 82 | 102 ± 70 | NS |
| Hs-CRP (mg/1) | 2.3 ± 2.2 | 1.1 ± 0.7 | 1.4 ± 0.9 | NS |
| Ox-LDL (mg/dl) | 1.1 ± 0.39 | 1.5 ± 0.7 | 1.2 ± 0.4 | NS |

Data shown are means ± SD.
*$P < 0.05$,
**$P < 0.01$ and
***$P < 0.001$ compared with control pigs;
††$P < 0.01$ compared with stage II.
Abbreviations: ADN: adiponectin; AUC: area under curve; C: cholesterol; HOMA-IR, homeostasis model assessment of insulin resistance.

TABLE 7

Primers used for qPCR analysis of human and mouse (micro) RNA extracts

| | | SEQ ID NO |
|---|---|---|
| Forward primer | | |
| Gene symbol | | |
| COX1 | 5'-CCACGGAAGCAATATGAAATGAT-3' | SEQ ID NO: 13 |
| COX4I1 | 5'-GGTCACGCCGATCCATATAAG-3' | SEQ ID NO: 15 |
| HPRT1 | 5'-CCCTTTCCAAATCCTCAGCAT-3' | SEQ ID NO: 17 |
| RUNX2 | 5'-CCCGAGGTCCATCTACTGTAACTT-3' | SEQ ID NO: 19 |
| SDHA | 5'-CTACCACCACTGCATCAAATTCAT-3' | SEQ ID NO: 21 |
| TBP | 5'-GGAGCTGTGATGTGAAGTTTCCTATA-3' | SEQ ID NO: 23 |
| TFAM | 5'-GCTAGTGGCGGGCATGAT-3' | SEQ ID NO: 25 |
| YWHAZ | 5'-TTGATCCCCAATGCTTCACA-3' | SEQ ID NO: 27 |
| Mouse RNA | | |
| Cox1 | 5'-CCCTAGATGACACATGAGCAAAAG-3' | SEQ ID NO: 29 |
| Cox4i1 | 5'-CAGCGGTGGCAGAATGTTG-3' | SEQ ID NO: 31 |
| Tfam | 5'-CCCTCGTCTATCAGTCTTGTCTGTAT-3' | SEQ ID NO: 33 |
| β-actin | 5'-ACGGCCAGGTCATCACTATTG-3' | SEQ ID NO: 35 |
| PIG RNA | | |
| COX1 | 5'-AGACCGCAACCTGAACACAAC-3 | SEQ ID NO: 37 |
| COX4I1 | 5'-TGGCCAAGCAGACCAAGAG-3' | SEQ ID NO: 39 |
| TFAM | 5'-GCTGAGCTGTGGAGGGAACT-3 | SEQ ID NO: 41 |
| B-actin | 5'-GGACCTGACCGACTACCTCATG-3' | SEQ ID NO: 43 |
| Reverse primer | | |
| Gene symbol | | |
| COX1 | 5'-CCTACGTGAAAAGAAAGATGAATC-3' | SEQ ID NO: 14 |
| COX4I1 | 5'-TCTGTGTGTGTACGAGCTCATGA-3' | SEQ ID NO: 16 |
| HPRT1 | 5'-CCTGGCGTCGTGATTAGTGA-3' | SEQ ID NO: 18 |
| RUNX2 | 5'-AGTAGCAAGGTTCAACGATCTGAGA-3' | SEQ ID NO: 20 |
| SDHA | 5'-GGAACAAGAGGGCATCTGCTA-3' | SEQ ID NO: 22 |

TABLE 7 -continued

Primers used for qPCR analysis of human and mouse (micro) RNA extracts

|  |  | SEQ ID NO |
|---|---|---|
| TBP | 5'-CCAGAAACAAAAATAAGGAGAACAATTC-3' | SEQ ID NO: 24 |
| TFAM | 5'-GTGACCCGACCCCAATCTC-3' | SEQ ID NO: 26 |
| YWHAZ | 5'-CGGCAACCTCAGCCAAGT-3' | SEQ ID NO: 28 |
| Mouse RNA |  |  |
| Cox1 | 5'-AGCGTCGTGGTATTCCTGAAA-3' | SEQ ID NO: 30 |
| Cox4i1 | 5'-ACACCGAAGTAGAAATGGCTCTCT-3' | SEQ ID NO: 32 |
| Tfam | 5'-ATTTGGGTAGCTGTTCTGTGGAA-3' | SEQ ID NO: 34 |
| β-actin | 5'-CACAGGATTCCATACCCAAGAAG-3' | SEQ ID NO: 36 |
| PIG RNA |  |  |
| COX1 | 5'-GGGTGTCCGAAAAATCAGAACA-3' | SEQ ID NO: 38 |
| COX4I1 | 5'-TCCCACTTGGCCGAGAAG-3' | SEQ ID NO: 40 |
| TFAM | 5'-TTGAATTCTGTTTACCTCTTCTTTGTACAC-3' | SEQ ID NO: 42 |
| B-actin | 5'-CGACGTAGCAGAGCTTCTCCTT-3' | SEQ ID NO: 44 |

Abbreviations:
COX1, cytochrome c oxidase, subunit I;
COX4I1, cytochrome c oxidase subunit IV isoform 1;
HPRT1, hypoxanthine phosphoribosyltransferase 1;
RUNX2, runt-related transcription factor 2;
SDHA, succinate dehydrogenase complex, subunit A, flavoprotein (Fp);
TBP, TATA box binding protein;
TFAM, transcription factor A, mitochondrial;
YWHAZ, ccctagtyrosine 3-monooxygenase/tryptophan 5-monooxygenase activation protein, zeta polypeptide.
HPRT1, SDHA, TBP, and YWHAZ were used as housekeeping genes.
For microRNA anlysis TaqMan microRNA assays from Life Technologies were used at Biogazelle: ID 00405 for miR-26a, ID 000602 for miR-30b, and ID 000554 for 361.

The invention claimed is:

1. A method for assessing risk of a human patient with coronary stenosis for experiencing one or more cardiovascular events selected from the group consisting of cardiovascular death, myocardial infarction, stroke or transient ischemic attack, and recurrent ischemia requiring percutaneous coronary intervention (PCI), coronary bypass surgery, or surgery or stenting of peripheral arteries, and administering a treatment regimen based on whether the human patient has an increased risk of experiencing the one or more cardiovascular events, the method comprising the steps of:
   (a) obtaining monocytes or monocyte derived microvesicles from a blood or blood-derived sample from the human patient;
   (b) measuring expression of cytochrome c oxidase, subunit I (COX1) in the monocytes or monocyte derived microvesicles;
   (c) determining the human patient has a decreased expression of COX1, compared to reference measurements from monocytes or monocyte derived microvesicles of one or more control patients not having cardiovascular disease and who were not undergoing treatment of cardiovascular disease, in the monocytes or monocyte derived microvesicles; and
   (d) administering a treatment regimen for the one or more cardiovascular events,
      wherein the treatment regimen is selected from surgery and a medicament.

2. The method according to claim 1, further comprising measuring expression of cytochrome c oxidase subunit IV isoform 1 (COX4I1) in the monocytes or monocyte derived microvesicles in step (b), and determining the human patient has decreased expression of COX1 and COX4I1, compared to corresponding reference measurements from monocytes or monocyte derived microvesicles of the one or more control patients, in the monocytes or monocyte derived microvesicles.

3. The method according to claim 2, further comprising measuring expression of transcription factor A, mitochondrial (TFAM) and runt-related transcription factor 2 (RUNX2) in the monocytes or monocyte derived microvesicles in step (b), and determining the human patient has decreased expression of COX1, COX4I1, TFAM and RUNX2, compared to corresponding reference measurements from monocytes or monocyte derived microvesicles of the one or more control patients, in the monocytes or monocyte derived microvesicles.

4. The method according to claim 1, wherein the one or more cardiovascular events occur within 3 years of determining the human patient has decreased expression of COX 1.

5. The method according to claim 1, wherein the one or more cardiovascular events occur within 1 year of determining the human patient has decreased expression of COX 1.

6. The method according to claim 1, wherein measuring expression of COX1 comprises measuring protein expression of COX1.

7. The method according to claim 1, wherein measuring expression of COX1 comprises measuring mRNA expression of COX1.

8. The method according to claim 1, wherein obtaining the monocytes or monocyte derived microvesicles comprises recognizing and isolating the monocytes or monocyte derived microvesicles using an anti-CD14 antibody that specifically binds the CD14 receptor.

9. The method according to claim 1, wherein the blood-derived sample is plasma or serum.

10. The method according to claim 1, wherein the reference measurements of COX1 are derived from COX1 expression within monocytes or monocyte derived microvesicles from the humans who do not have coronary stenosis.

11. The method according to claim 1, wherein the one or more control patients from which the reference measurements are obtained comprises the human patient, and wherein the reference measurements were obtained from the human patient at a time point when the human patient did not have coronary stenosis.

* * * * *

SEQUENCE LISTING

<160> NUMBER OF SEQ ID NOS: 44

<210> SEQ ID NO 1
<211> LENGTH: 1542
<212> TYPE: DNA
<213> ORGANISM: Homo sapiens

<400> SEQUENCE: 1

```
atgttcgccg accgttgact attctctaca aaccacaaag acattggaac actataccta      60
ttattcggcg catgagctgg agtcctaggc acagctctaa gcctccttat tcgagccgag     120
ctgggccagc caggcaacct tctaggtaac gaccacatct acaacgttat cgtcacagcc     180
catgcatttg taataatctt cttcatagta atacccatca taatcggagg ctttggcaac     240
tgactagttc ccctaataat cggtgccccc gatatggcgt tccccgcat aaacaacata     300 agcttctgac tcttacctcc ctctctccta ctcctgctcg catctgctat agtggaggcc     360
ggagcaggaa caggttgaac agtctaccct cccttagcag ggaactactc ccaccctgga     420
gcctccgtag acctaaccat cttctcctta cacctagcag gtgtctcctc tatcttaggg     480
gccatcaatt tcatcacaac aattatcaat ataaaacccc ctgccataac ccaataccaa     540
acgcccctct tcgtctgatc cgtcctaatc acagcagtcc tacttctcct atctctccca     600
gtcctagctg ctggcatcac tatactacta acagaccgca acctcaacac caccttcttc     660
gaccccgccg gaggaggaga ccccattcta taccaacacc tattctgatt tttcggtcac     720
cctgaagttt atattcttat cctaccaggc ttcggaataa tctcccatat tgtaacttac     780
tactccggaa aaaagaacc atttggatac ataggtatgg tctgagctat gatatcaatt     840
ggcttcctag ggtttatcgt gtgagcacac catatattta cagtaggaat agacgtagac     900
```

-continued

| | |
|---|---|
| acacgagcat atttcacctc cgctaccata atcatcgcta tccccaccgg cgtcaaagta | 960 |
| tttagctgac tcgccacact ccacggaagc aatatgaaat gatctgctgc agtgctctga | 1020 |
| gccctaggat tcatctttct tttcaccgta ggtggcctga ctggcattgt attagcaaac | 1080 |
| tcatcactag acatcgtact acacgacacg tactacgttg tagcccactt ccactatgtc | 1140 |
| ctatcaatag gagctgtatt tgccatcata ggaggcttca ttcactgatt tcccctattc | 1200 |
| tcaggctaca ccctagacca aacctacgcc aaaatccatt tcactatcat attcatcggc | 1260 |
| gtaaatctaa ctttcttccc acaacacttt ctcggcctat ccggaatgcc cgacgttac | 1320 |
| tcggactacc ccgatgcata caccacatga aacatcctat catctgtagg ctcattcatt | 1380 |
| tctctaacag cagtaatatt aataattttc atgatttgag aagccttcgc ttcgaagcga | 1440 |
| aaagtcctaa tagtagaaga accctccata aacctggagt gactatatgg atgccccca | 1500 |
| ccctaccaca cattcgaaga acccgtatac ataaaatcta ga | 1542 |

<210> SEQ ID NO 2
<211> LENGTH: 513
<212> TYPE: PRT
<213> ORGANISM: Homo sapiens

<400> SEQUENCE: 2

Met Phe Ala Asp Arg Trp Leu Phe Ser Thr Asn His Lys Asp Ile Gly
1               5                  10                  15

Thr Leu Tyr Leu Leu Phe Gly Ala Trp Ala Gly Val Leu Gly Thr Ala
            20                  25                  30

Leu Ser Leu Leu Ile Arg Ala Glu Leu Gly Gln Pro Gly Asn Leu Leu
        35                  40                  45

Gly Asn Asp His Ile Tyr Asn Val Ile Val Thr Ala His Ala Phe Val
    50                  55                  60

Met Ile Phe Phe Met Val Met Pro Ile Met Ile Gly Gly Phe Gly Asn
65                  70                  75                  80

Trp Leu Val Pro Leu Met Ile Gly Ala Pro Asp Met Ala Phe Pro Arg
                85                  90                  95

Met Asn Asn Met Ser Phe Trp Leu Leu Pro Pro Ser Leu Leu Leu Leu
            100                 105                 110

Leu Ala Ser Ala Met Val Glu Ala Gly Ala Gly Thr Gly Trp Thr Val
        115                 120                 125

Tyr Pro Pro Leu Ala Gly Asn Tyr Ser His Pro Gly Ala Ser Val Asp
    130                 135                 140

Leu Thr Ile Phe Ser Leu His Leu Ala Gly Val Ser Ser Ile Leu Gly
145                 150                 155                 160

Ala Ile Asn Phe Ile Thr Thr Ile Ile Asn Met Lys Pro Pro Ala Met
                165                 170                 175

Thr Gln Tyr Gln Thr Pro Leu Phe Val Trp Ser Val Leu Ile Thr Ala
            180                 185                 190

Val Leu Leu Leu Leu Ser Leu Pro Val Leu Ala Ala Gly Ile Thr Met
        195                 200                 205

Leu Leu Thr Asp Arg Asn Leu Asn Thr Thr Phe Phe Asp Pro Ala Gly
    210                 215                 220

Gly Gly Asp Pro Ile Leu Tyr Gln His Leu Phe Trp Phe Phe Gly His
225                 230                 235                 240

Pro Glu Val Tyr Ile Leu Ile Leu Pro Gly Phe Gly Met Ile Ser His
                245                 250                 255

Ile Val Thr Tyr Tyr Ser Gly Lys Lys Glu Pro Phe Gly Tyr Met Gly

```
                260             265             270
Met Val Trp Ala Met Met Ser Ile Gly Phe Leu Gly Phe Ile Val Trp
            275             280             285

Ala His His Met Phe Thr Val Gly Met Asp Val Asp Thr Arg Ala Tyr
        290              295             300

Phe Thr Ser Ala Thr Met Ile Ile Ala Ile Pro Thr Gly Val Lys Val
305             310              315             320

Phe Ser Trp Leu Ala Thr Leu His Gly Ser Asn Met Lys Trp Ser Ala
            325              330             335

Ala Val Leu Trp Ala Leu Gly Phe Ile Phe Leu Phe Thr Val Gly Gly
            340              345             350

Leu Thr Gly Ile Val Leu Ala Asn Ser Ser Leu Asp Ile Val Leu His
        355              360              365

Asp Thr Tyr Tyr Val Val Ala His Phe His Tyr Val Leu Ser Met Gly
        370              375              380

Ala Val Phe Ala Ile Met Gly Gly Phe Ile His Trp Phe Pro Leu Phe
385             390              395              400

Ser Gly Tyr Thr Leu Asp Gln Thr Tyr Ala Lys Ile His Phe Thr Ile
            405             410              415

Met Phe Ile Gly Val Asn Leu Thr Phe Phe Pro Gln His Phe Leu Gly
            420              425             430

Leu Ser Gly Met Pro Arg Arg Tyr Ser Asp Tyr Pro Asp Ala Tyr Thr
            435              440             445

Thr Trp Asn Ile Leu Ser Ser Val Gly Ser Phe Ile Ser Leu Thr Ala
        450              455             460

Val Met Leu Met Ile Phe Met Ile Trp Glu Ala Phe Ala Ser Lys Arg
465             470              475              480

Lys Val Leu Met Val Glu Glu Pro Ser Met Asn Leu Glu Trp Leu Tyr
            485              490             495

Gly Cys Pro Pro Pro Tyr His Thr Phe Glu Glu Pro Val Tyr Met Lys
            500              505             510

Ser

<210> SEQ ID NO 3
<211> LENGTH: 839
<212> TYPE: DNA
<213> ORGANISM: Homo sapiens

<400> SEQUENCE: 3
aagcagcccg gcccggcatt ttacgacgtt cgcagcgcta ccctttccg ctccacggtg      60 acctccgtgc ggccgggtgc gggcggagtc ttcctcgatc ccgtggtgct ccgcggcgcg     120
gccttgctct cttccggtcg cgggacaccg ggtgtagagg gcggtcgcgg cgggcagtgg     180
cggcagaatg ttggctacca gggtatttag cctagttggc aagcgagcaa tttccacctc     240
tgtgtgtgta cgagctcatg aaagtgttgt gaagagcgaa gacttttcgc tcccagctta     300
tatggatcgg cgtgaccacc ccttgccgga ggtggcccat gtcaagcacc tgtctgccag     360
ccagaaggca ttgaaggaga aggagaaggc ctcctggagc agcctctcca tggatgagaa     420
agtcgagttg tatcgcatta agttcaagga gagctttgct gagatgaaca ggggctcgaa     480
cgagtggaag acggttgtgg gcggtgccat gttcttcatc ggtttcaccg cgctcgttat     540
catgtggcag aagcactatg tgtacggccc cctcccgcaa agctttgaca aagagtgggt     600
ggccaagcag accaagagga tgctggacat gaaggtgaac cccatccagg gcttagcctc     660
```

| | |
|---|---|
| caagtgggac tacgaaaaga acgagtggaa gaagtgagag atgctggcct gcgcctgcac | 720 |
| ctgcgcctgg ctctgtcacc gccatgcaac tccatgccta tttactgtgaa acctgttatg | 780 |
| ccaaacagtt gtaccactgc taataaatga ccagtttacc tgaaaaaaaa aaaaaaaaa | 839 |

<210> SEQ ID NO 4
<211> LENGTH: 169
<212> TYPE: PRT
<213> ORGANISM: Homo sapiens

<400> SEQUENCE: 4

```
Met Leu Ala Thr Arg Val Phe Ser Leu Val Gly Lys Arg Ala Ile Ser
1               5                   10                  15

Thr Ser Val Cys Val Arg Ala His Glu Ser Val Val Lys Ser Glu Asp
            20                  25                  30

Phe Ser Leu Pro Ala Tyr Met Asp Arg Arg Asp His Pro Leu Pro Glu
        35                  40                  45

Val Ala His Val Lys His Leu Ser Ala Ser Gln Lys Ala Leu Lys Glu
    50                  55                  60

Lys Glu Lys Ala Ser Trp Ser Ser Leu Ser Met Asp Glu Lys Val Glu
65                  70                  75                  80

Leu Tyr Arg Ile Lys Phe Lys Glu Ser Phe Ala Glu Met Asn Arg Gly
                85                  90                  95

Ser Asn Glu Trp Lys Thr Val Val Gly Gly Ala Met Phe Phe Ile Gly
            100                 105                 110

Phe Thr Ala Leu Val Ile Met Trp Gln Lys His Tyr Val Tyr Gly Pro
        115                 120                 125

Leu Pro Gln Ser Phe Asp Lys Glu Trp Val Ala Lys Gln Thr Lys Arg
    130                 135                 140

Met Leu Asp Met Lys Val Asn Pro Ile Gln Gly Leu Ala Ser Lys Trp
145                 150                 155                 160

Asp Tyr Glu Lys Asn Glu Trp Lys Lys
                165
```

<210> SEQ ID NO 5
<211> LENGTH: 5487
<212> TYPE: DNA
<213> ORGANISM: Homo sapiens

<400> SEQUENCE: 5

| | |
|---|---|
| gtgtgaatgc ttcattcgcc tcacaaacaa ccacagaacc acaagtgcgg tgcaaacttt | 60 |
| ctccaggagg acagcaagaa gtctctggtt tttaaatggt taatctccgc aggtcactac | 120 |
| cagccaccga gaccaacaga gtcatttaag gctgcaagca gtatttacaa cagagggtac | 180 |
| aagttctatc tgaaaaaaaa aggagggact atggcatcaa acagcctctt cagcacagtg | 240 |
| acaccatgtc agcaaaactt cttttgggat ccgagcacca gccggcgctt cagccccccc | 300 |
| tccagcagcc tgcagcccgg caaaatgagc gacgtgagcc cggtggtggc tgcgcaacag | 360 |
| cagcagcaac agcagcagca gcaacagcag cagcagcagc agcaacagca gcagcagcag | 420 |
| caggaggcgg cggcggcggc tgcggcggcg gcggcggctg cggcggcggc agctgcagtg | 480 |
| ccccggttgc ggccgcccca cgacaaccgc accatggtgg agatcatcgc cgaccacccg | 540 |
| gccgaactcg tccgcaccga cagccccaac ttcctgtgct cggtgctgcc ctcgcactgg | 600 |
| cgctgcaaca gaccctgcc cgtggccttc aaggtggtag ccctcggaga ggtaccagat | 660 |
| gggactgtgg ttactgtcat ggcgggtaac gatgaaaatt attctgctga gctccggaat | 720 |

```
gcctctgctg ttatgaaaaa ccaagtagca aggttcaacg atctgagatt tgtgggccgg      780
agtggacgag gcaagagttt caccttgacc ataaccgtct tcacaaatcc tccccaagta      840
gctacctatc acagagcaat taaagttaca gtagatggac ctcgggaacc cagaaggcac      900
agacagaagc ttgatgactc taaacctagt ttgttctctg accgcctcag tgatttaggg      960
cgcattcctc atcccagtat gagagtaggt gtcccgcctc agaacccacg gccctccctg     1020
aactctgcac caagtccttt taatccacaa ggacagagtc agattacaga ccccaggcag     1080
gcacagtctt ccccgccgtg gtcctatgac cagtcttacc cctcctacct gagccagatg     1140
acgtccccgt ccatccactc taccaccccg ctgtcttcca cacggggcac tgggcttcct     1200
gccatcaccg atgtgcctag gcgcatttca ggtgcttcag aactgggccc tttttcagac     1260
cccaggcagt tcccaagcat ttcatccctc actgagagcc gcttctccaa cccacgaatg     1320
cactatccag ccacctttac ttacaccccg ccagtcacct caggcatgtc cctcggtatg     1380
tccgccacca ctcactacca cacctacctg ccaccaccct accccggctc ttcccaaagc     1440
cagagtggac ccttccagac cagcagcact ccatatctct actatggcac ttcgtcagga     1500
tcctatcagt ttcccatggt gccgggggga gaccggtctc cttccagaat gcttccgcca     1560
tgcaccacca cctcgaatgg cagcacgcta ttaaatccaa atttgcctaa ccagaatgat     1620
ggtgttgacg ctgatggaag ccacagcagt tccccaactg ttttgaattc tagtggcaga     1680
atggatgaat ctgtttggcg accatattga aattcctcag cagtggccca gtggtatctg     1740
ggggccacat cccacacgta tcaatatata catatataga gagagtgcat atatatgtat     1800
atcgattagc tatctacaaa gtgcctattt tttagaagat ttttcattca ctcactcagt     1860
catgatcttg cagccataag agggtagata ttgagaagca gaaggctcaa gagagacaat     1920
tgcaatcgag cttcagattg tttactattt aagatgtact tttacaaagg aacaaagaag     1980
ggaaaaggta ttttttgtttt tgttgtttgg tctgttatca tcaataaccct gttcatatgc     2040 caattcagag aggtggactc caggttcagg agggagaaga gcaaagccgc ttcctctctg     2100
tgctttgaaa cttcacaccc tcacggtggc agctgtgtat ggaccagtgc cctccgcaga     2160
cagctcacaa aaccagttga ggtgcactaa agggacatga ggtagaatgg atgcttccat     2220
cacagtacca tcattcagaa taactcttcc aatttctgct ttcagacatg ctgcaggtcc     2280
tcatctgaac tgttgggttc gttttttttt ttttttttcc tgctccaaga aagtgacttc     2340
aaaaataact gatcaggata gattatttta ttttactttt taacactcct tctcccctttt     2400 tcccactgaa ccaaaagaa atcccatccc taaaacctgc cttctccttt tatgcaaaac      2460
tgaaaatggc aatacattat tatagccata atggtataga tagtgattgc gtttggctat     2520
gtgttgtttt cttttttttt aaattatgaa tatgtgtaaa atctgaggta acttgctaac     2580
gtgaatggtc atataacttt aaagatatat ttataattat ttaatgacat ttggacccttt    2640 gaaacatttc ttagtgtatt gatatgttga cttcggtctc taaaagtgct ctttattaaa     2700
taacaaattt cttcagtggt ctagagccat atctgaaata ttgctaagca atttcagttc     2760
atccaggcac aatgtgattt taaaaaatac ttccatctcc aaatatttta gatatagatt     2820 gttttttgtga tgtatgaagg aaatgttatg tttagttctt tcagatctttt gaatgcctct     2880 aacacagctt tgccttctaa agcggtaatt agggatttaa aaaacaaccct ttagcccttt    2940 atcagcatga aatgctggag tgatgtggtt ttctaatttc tttggggtaa ttatgactct     3000
tgtcatatta aaaagacaag cacaagtaaa tcattgaact acagaaaaat gttctgtggt     3060
ttcatagtta agcaaaactc taaatcgcca ggcttcatag caaagacata gtcagctaaa     3120
```

```
agccgcacat gtggatagag ggttcaatta tgagacacct agtacaggag agcaaaattg    3180
caccagagat tcttaaccaa ccagccttac caaacaacac aacaggggaa ccccaatctg    3240
ccttacccaa ggccccactg gcagctttcc acagaatttg catttagagg agcagaatga    3300
catcactgtc ctttgggagt aggtcctctg aaaaggcagc aggttccagc aggtagctga    3360
gctgagagga catatggccc acggggacct acagacagcc tttgacattt gtatttctta    3420
caatggaggg ccaaggaggg caaggggctg tggagtttgg tgtctactag tgtgtatgaa    3480
tttgagctag agtccttctg tggcatgcac tttgaccact cctggcagtc acatggcaga    3540
tttccaagtg caaatcctta atccaaacaa ggatcatcta atgacaccac caggccaatc    3600
cctgctctcc tccccgaaaa gtcagggtcc cttcattgga atcctccacc cacccaagca    3660
gaatttagca gagatttgcc ttcaaaccct aacggccccc ttgttctctg gtccttctca    3720
aacccacctt tgtaggccac ccagcattgc aggacagcgt gtgggcagc tggacctgtg     3780 cttcctgcct gggagtctcc cttggaattc atcctgactc cttctaataa aaatggatgg    3840
gaaagcaaaa cactttgcct tctaaaggcc gtataccaag tatgcttaga taaataagcc    3900
acttttctat tacttaagta agaaggaagt agtaattgat actatttatt gtttgtgtgt    3960
ggtagcttga agcacaccac tgtccattta tttgtaagtg taaaatatgt gtgtttgttt    4020
cagcagcact taaaaaagcc agtgtctggt tacacatttc aattttaatt aattgacata    4080
aaaatgctac cgccagtgcc agctgcatcc tatttaatta aaaaggtact atatttgtac    4140 attattttt aatgttaaaa gggcttttt aagtttacag tacacatacc gagtgacttt     4200
agggatgctt ttgtgttgaa atgttactat agtggctgca ggcagcaacc cagaaacact    4260
ttagaagctt ttttttccttg ggaaaaattc aagcacttct tccctccacc ctcactccaa   4320
ccaccccaat gggggtaatt cacatttctt agaacaaatt ctgcccttt ttggtctagg     4380 gattaaaatt ttgttttct ttctttcttt tttttttt ttcactgaac ccttaatttg       4440
cactgggtca tgtgtttgat ttgtgatttc aagaccaaag caaagtctta ctactactgt    4500
ggaaccatgt actagttcct gggaattaaa atagcgtggt tctctttgta gcacaaacat    4560
tgctggaatt tgcagtcttt tcaatgcagc cacatttta tccatttcag ttgtctcaca     4620
aattttaacc catatcagag ttccagaaca ggtaccacag cttgttttt agattagtgg     4680 aataacattc agcccagaac tgagaaactc aacagattaa ctatcgtttg ctctttagac    4740
ggtctcactg cctctcactt gccagagccc tttcaaaatg agcagagaag tccacaccat    4800
tagggaccat ctgtgataaa ttcagaaggg aggagatgtg tgtacagctt taaggattcc    4860
ctcaattccg aggaaaggga ctggcccaga atccaggtta atacatggaa acacgaagca    4920
ttagcaaaag taataattat acctatggta tttgaaagaa caataataaa agacacttct    4980
tccaaacctt gaatttgttg ttttttagaaa acgaatgcat ttaaaaatat tttctatgtg   5040 agaattttt agatgtgtgt ttacttcatg tttacaaata actgtttgct ttttaatgca    5100
gtactttgaa atatatcagc caaaaccata acttacaata atttcttagg tattctgaat    5160
aaaattccat ttctttttgga tatgcttac cattcttagg tttctgtgga acaaaaatat    5220
ttgtagcatt ttgtgtaaat acaagctttc attttattt tttccaattg ctattgccca    5280
agaattgctt tccatgcaca tattgtaaaa attccgcttt gtgccacagg tcatgattgt    5340
ggatgagttt actcttaact tcaaagggac tatttgtatt gtatgttgca actgtaaatt    5400
gaattatttg gcatttttct catgattgta atattaattt gaagtttgaa tttaattttc    5460
```
aataaaatgg ctttttttggt tttgtta                                                  5487

<210> SEQ ID NO 6
<211> LENGTH: 172
<212> TYPE: PRT
<213> ORGANISM: Homo sapiens

<400> SEQUENCE: 6

Met Arg Ile Pro Val Asp Pro Ser Thr Ser Arg Arg Phe Ser Pro Pro
1               5                   10                  15

Ser Ser Ser Leu Gln Pro Gly Lys Met Ser Asp Val Ser Pro Val Val
            20                  25                  30

Ala Ala Gln Gln Gln Gln Gln Gln Gln Gln Gln Gln Gln Gln Gln Gln
        35                  40                  45

Gln Gln Gln Gln Gln Gln Gln Gln Glu Ala Ala Ala Ala Ala Ala Ala
    50                  55                  60

Ala Ala Ala Ala Ala Val Pro Arg Leu Arg Pro Pro His Asp Asn Arg
65                  70                  75                  80

Thr Met Val Glu Ile Ile Ala Asp His Pro Ala Glu Leu Val Arg Thr
                85                  90                  95

Asp Ser Pro Asn Phe Leu Cys Ser Val Leu Pro Ser His Trp Arg Cys
            100                 105                 110

Asn Lys Thr Leu Pro Val Ala Phe Lys Val Val Ala Leu Gly Glu Val
        115                 120                 125

Pro Asp Gly Thr Val Val Thr Val Met Ala Gly Asn Asp Glu Asn Tyr
    130                 135                 140

Ser Ala Glu Leu Arg Asn Ala Ser Ala Val Met Lys Asn Gln Val Ala
145                 150                 155                 160

Arg Phe Asn Asp Leu Arg Phe Val Gly Arg Ser Gly
                165                 170

<210> SEQ ID NO 7
<211> LENGTH: 94
<212> TYPE: PRT
<213> ORGANISM: Homo sapiens

<400> SEQUENCE: 7

Met Ala Asp Phe Gln Val Gln Ile Leu Asn Pro Asn Lys Asp His Leu
1               5                   10                  15

Met Thr Pro Pro Gly Gln Ser Leu Leu Ser Ser Pro Lys Ser Gln Gly
            20                  25                  30

Pro Phe Ile Gly Ile Leu His Pro Pro Lys Gln Asn Leu Ala Glu Ile
        35                  40                  45

Cys Leu Gln Thr Leu Thr Ala Pro Leu Phe Ser Gly Pro Ser Gln Thr
    50                  55                  60

His Leu Cys Arg Pro Pro Ser Ile Ala Gly Gln Arg Val Gly Gln Leu
65                  70                  75                  80

Asp Leu Cys Phe Leu Pro Gly Ser Leu Pro Trp Asn Ser Ser
                85                  90

<210> SEQ ID NO 8
<211> LENGTH: 5223
<212> TYPE: DNA
<213> ORGANISM: Homo sapiens

<400> SEQUENCE: 8
ggggtgaggc cgccgccgcg gtccctccat caccctcctg gcccggcaga ggaacccact         60

```
gctccgggcg gccggggaca gaggtggctc aacagcgccg cctcgaagcc agagccctcc    120
gcaggctaga ggattgcggt ttcccttcat ctccgcggct cttattcctc ccccgcaagg    180
ccgcccaccg gggtacgctc tcccgcgcct gcgccaattc cgccccgccc cgcccccatc    240
taccgaccgg atgttagcag atttcccata gtgcctcgct agtggcgggc atgataacac    300
acgccggagg gtcgcacgcg ggttccagtt gtgattgctg gagttgtgta ttgccaggag    360
gctctccgag attggggtcg ggtcactgcc tcatccaccg gagcgatggc gtttctccga    420
agcatgtggg gcgtgctgag tgccctggga aggtctggag cagagctgtg caccggctgt    480
ggaagtcgac tgcgctcccc cttcagtttt gtgtatttac cgaggtggtt ttcatctgtc    540
ttggcaagtt gtccaaagaa acctgtaagt tcttaccttc gattttctaa agaacaacta    600
cccatattta aagctcagaa cccagatgca aaaactacag aactaattag aagaattgcc    660
cagcgttgga gggaacttcc tgattcaaag aaaaaaatat atcaagatgc ttatagggcg    720
gagtggcagg tatataaaga agagataagc agatttaaag aacagctaac tccaagtcag    780
attatgtctt tggaaaaaga aatcatggac aaacatttaa aaaggaaagc tatgacaaaa    840
aaaaaagaaa agctgaagac tgtaaaggaa aactggaaaa atctgtctga ctctgaaaag    900
gaattatata ttcagcatgc taaagaggac gaaactcgtt atcataatga aatgaagtct    960
tgggaagaac aaatgattga agttggacga aaggatcttc tacgtcgcac aataaagaaa   1020
caacgaaaat atggtgctga ggagtgttaa agtagaaga ttgagatgtg ttcacaatgg   1080
ataggcacag gaaaccagtt aggtctcaat acctgaagct atcgtaaaat taagaaagga   1140
taaagttggt aaaccttta tatttagtat cttttattc agctcatgga cttctgccag   1200
cataatactt gctttggaaa acccagataa aggttcatgc aaactttatt ttgtgtttag   1260
gaactactga ggatcagagt aatccaagca atgtgaatc attttacctt tgacaaaggt   1320
aaatcagact atgaagtttt ttttatacag gatgatgact atggaaagag tactcttgtt   1380
tccttatatt atgagggcag gagtttcgtt ttcaaaattg ttacaaattg tagaagccac   1440
ggtgttctgt gatataagtg tgtgttttc ataaagcagg cagaactcat ctaggtaaat   1500
tacagttcct aggtataatt cacattgtat tcagagttga tggttgtaca tataagtgat   1560
tgctggtttt agttgcaact ttgtataaaa gggactgaga aatttataaa ctttttttctt   1620 actgtctttt ttctaaagta aaaacaaaga aattatgtgc cagatttatg catattattt   1680
tatgttgcat agaataaaat ttttaatctt taattttaca tttcctaaat atattttaag   1740
acgaaacatt tgttctatag cttttccctt tttttaagta aggaattta ttttttttctg   1800 aattattttc tctcgtgagt atattgatcc agaaagaaaa cttgtattat gtgtgttta   1860 aaatgagaaa tctaaaaaac gaaaagtctc caaagtctct ggaatttgaa acactttgca   1920
taacgtataa aagcctgttt aagagacagc caactatggc ctgtggatca aatccagcct   1980
gctgcctgct ttttatggcc tgtgagctag gaattgtgtt tataatttta aatgttttt   2040 tttaaagact tttatgatac ttgaaaatta acatgaatat ttagtgttca taaataaagt   2100
ttgttgaaac acaaccaaga tcattctttt acttgtctat ggctgcttt ctgtggcaga   2160 gtagctgcca cagaaactat agcccacaaa gcctgatat tactgtctgt ctgtttatgg   2220
aaaaaattta tcaacccatg gtctatagta tagtgtgata tgactactgt tccaatgtat   2280
tgaagtgttg ggatagtttt ttcaaatgtt ttcagatgtt cttgttttag aatcattgtc   2340 accttttaaga ggaaaaaggt catcactaga taatctaaac aaattgttgc ttctcagtgt   2400
tagcaaggaa aataatctag tttcaaatta cattgcagta taatgaaaaa gatccatata   2460
```

```
ctgtggaatg atattctttt aaaattattt gctatggctt ggtaaaaatg tacttttcc    2520 agtagcacat atcacaagaa cctcactgta gttgaaagcc atctttcttt agtatttgtt    2580 tatccttta ggagagtcaa gcaaaggttt tcaccacctg tttgagcaga ataattctca    2640
tcagttcaca gatataggat aactcaattt atatgcactt tatgcgttat gcaaatatt    2700 tagaaattgt agattctaga tctccagaaa gactttgaag actttgatgt cacaaaaga    2760 tgacttgtta tatgctgagc ttgacaaagg taggaatggg agagaaaat agtagcttat    2820 gaggaaatat gaggctttaa atatataaag ttggatattt taaataact ttccctgtg    2880 ggagcttctc actctgggtg cagacaggac agtgttggcc attggtgaaa tagataggat    2940
gggtttgagg ccagagcagt ctggagtag ggggaaagag aaggaggtgt gctagtgtct    3000
atcacaggct ttctcaatta ggtttgcagg agaaaaagcc ctaagtccct gtgtcatcta    3060
gaatggtact aattatgtac agtccctagg agaatggaga aaatcataac tcaaatcatc    3120
gactcaattc tgttctcttc agatgagctc agagagcaca taggagtgtt tgtaatgagg    3180
ggtatgtaat gattgagata gaggaatgag ttacataaac atctcgggac aaatgcagca    3240
tagaaaacat ctttgtagtt accctgcggg gaaatttcct ctgagttctt ttaacattaa    3300
ctacccgtat tattttatac ttaacattca tatcatacct tcccaaatat attgggaagt    3360
tcagtgttaa gtacgtttct caagtactta acaacttaat atagggagga aaggtgtaaa    3420
cagtgaaaaa agagcaaaac tattttatgg taattttatg gtagtatcag cttgtatttg    3480
gttctctgtt tctaaaataa tgtaatttt aatattttaa aataggat aacctggttt    3540 ccaagccttt ttttccccg acatccagaa tacacactgg atccaagcct tcttaaaca    3600 tcagtacatg tggaagactg gcatgccata taccaaatgc cattcagctg taacagtata    3660
cacagatttt ctcttataaa gaataagaac atcataacca atgaccactc atataaagtc    3720
ttatttgtgt gtgtgtgtgt gtgtgtgtgc acgtgtgtgt gttagagtct cattatattg    3780
ctcaggctgg agggcatggt gtgatcttgg ctcactgcag ccttgacctc ctgggctcaa    3840
gtgatccttc cgagtcgttg ggactacagt aggtgaacac caccatgcct ggctaatttt    3900 tgtattttt ttttaatcaa gatgggatct tgctatgttg cccaggctgg tctcaaactc    3960
ctggcatcaa gcgttcctcc ttccttggcc tccttaagtg ctgggattat aggtgtgagc    4020
caccatgctt gaccataaag ccttactatt tcttttggag acacagtctt gctctgtcca    4080
agctggaatg cagtgatgtg atcatggctc actgcagcct tgaactccca ggcttaagag    4140
atcctcccat ctcagcctcc tgagtagctg ggattatagg tgcagaccat caagccttgc    4200
tattattttt tagactttc ttaatttcat ccaacaaagt agttgctgta ggagctgagt    4260
gttagaagga aagatgctga agaaatgaaa tcaagcaggg tgtatactgt catgaatagg    4320
catacagtag tttttatact tttgttcttt ggagtaccaa tgttaggttt tacaaaagta    4380
atttgatgag gggaaggagg gttgtgtatt tattttactt tctgatgttt gcttaaataa    4440
tactgtgtac gtattcagct tgctgtaatt ctgtaattac gctattgcgt ttggctaact    4500 ccttttgga aatgtctttt ttttgtaca aggcatgtgt tagttttac taattgctct    4560 gaatgtgtat atttagattt ctgaattgaa aaaaatagc gtacaataag tagatttaaa    4620
gtaattagaa cactttattg attttctga tgtttctgt atctaaaatt tatcaccacc    4680
aggttgtgct aaaacagcag gaagttttta tattgtgagt gacagtaccc attatttctc    4740 ttaatttac taacatttac tataagaata ttctctcgct cttttctcca ctcacagcca    4800
```

```
ttctccctcc ttctcttcat aacatcaagc tgtcacagac aaatctgaaa atgttacaag    4860
cacagactat gttgtatgtt ttgaaatttt agaacagtaa tgttcttttt aaaattgaac    4920
ttctgcagag taagaaaatg aatacattta ttactttaaa tttgtaaaat tttccaaagt    4980
aaaaccatac aaagctagtg tcagtctctc tcattgttca caaataaagg acttttgtta    5040
attgattaaa tcacttacta tattcgatat gaaatatata aacatacaa ccattatcta     5100 atacatttca gaatgtttca ctggttacag gagccagtaa ataaagttga ctctaaacag    5160 gaatttttaaa taaactaaac atttttttcat caccaagcat catttaaaaa aaaaaaaaa   5220 aaa                                                                  5223
```

<210> SEQ ID NO 9
<211> LENGTH: 214
<212> TYPE: PRT
<213> ORGANISM: Homo sapiens

<400> SEQUENCE: 9

```
Met Ala Phe Leu Arg Ser Met Trp Gly Val Leu Ser Ala Leu Gly Arg
1               5                   10                  15

Ser Gly Ala Glu Leu Cys Thr Gly Cys Gly Ser Arg Leu Arg Ser Pro
            20                  25                  30

Phe Ser Phe Val Tyr Leu Pro Arg Trp Phe Ser Ser Val Leu Ala Ser
        35                  40                  45

Cys Pro Lys Lys Pro Val Ser Ser Tyr Leu Arg Phe Ser Lys Glu Gln
    50                  55                  60

Leu Pro Ile Phe Lys Ala Gln Asn Pro Asp Ala Lys Thr Thr Glu Leu
65                  70                  75                  80

Ile Arg Arg Ile Ala Gln Arg Trp Arg Glu Leu Pro Asp Ser Lys Lys
                85                  90                  95

Lys Ile Tyr Gln Asp Ala Tyr Arg Ala Glu Trp Gln Val Tyr Lys Glu
            100                 105                 110

Glu Ile Ser Arg Phe Lys Glu Gln Leu Thr Pro Ser Gln Ile Met Ser
        115                 120                 125

Leu Glu Lys Glu Ile Met Asp Lys His Leu Lys Arg Lys Ala Met Thr
    130                 135                 140

Lys Lys Lys Glu Lys Leu Lys Thr Val Lys Glu Asn Trp Lys Asn Leu
145                 150                 155                 160

Ser Asp Ser Glu Lys Glu Leu Tyr Ile Gln His Ala Lys Glu Asp Glu
                165                 170                 175

Thr Arg Tyr His Asn Glu Met Lys Ser Trp Glu Glu Gln Met Ile Glu
            180                 185                 190

Val Gly Arg Lys Asp Leu Leu Arg Arg Thr Ile Lys Lys Gln Arg Lys
        195                 200                 205

Tyr Gly Ala Glu Glu Cys
    210
```

<210> SEQ ID NO 10
<211> LENGTH: 77
<212> TYPE: DNA
<213> ORGANISM: Artificial sequence
<220> FEATURE:
<223> OTHER INFORMATION: microRNA-26a

<400> SEQUENCE: 10

```
gtggcctcgt tcaagtaatc caggataggc tgtgcaggtc ccaatgggcc tattcttggt    60
tacttgcacg gggacgc                                                    77
```

-continued

<210> SEQ ID NO 11
<211> LENGTH: 88
<212> TYPE: DNA
<213> ORGANISM: Artificial sequence
<220> FEATURE:
<223> OTHER INFORMATION: Micro RNA-30b

<400> SEQUENCE: 11
accaagtttc agttcatgta aacatcctac actcagctgt aatacatgga ttggctggga    60
ggtggatgtt tacttcagct gacttgga                                       88

<210> SEQ ID NO 12
<211> LENGTH: 72
<212> TYPE: DNA
<213> ORGANISM: Artificial sequence
<220> FEATURE:
<223> OTHER INFORMATION: micro-RNA-361

<400> SEQUENCE: 12
ggagcttatc agaatctcca ggggtacttt ataatttcaa aaagtccccc aggtgtgatt    60
ctgatttgct tc                                                        72

<210> SEQ ID NO 13
<211> LENGTH: 23
<212> TYPE: DNA
<213> ORGANISM: Homo sapiens

<400> SEQUENCE: 13
ccacggaagc aatatgaaat gat                                            23

<210> SEQ ID NO 14
<211> LENGTH: 24
<212> TYPE: DNA
<213> ORGANISM: Homo sapiens

<400> SEQUENCE: 14
cctacgtgaa aagaaagatg aatc                                           24

<210> SEQ ID NO 15
<211> LENGTH: 21
<212> TYPE: DNA
<213> ORGANISM: Homo sapiens

<400> SEQUENCE: 15
ggtcacgccg atccatataa g                                              21

<210> SEQ ID NO 16
<211> LENGTH: 23
<212> TYPE: DNA
<213> ORGANISM: Homo sapiens

<400> SEQUENCE: 16
tctgtgtgtg tacgagctca tga                                            23

<210> SEQ ID NO 17
<211> LENGTH: 21
<212> TYPE: DNA
<213> ORGANISM: Homo sapiens

<400> SEQUENCE: 17 cccttttccaa atcctcagca t                                             21

```
<210> SEQ ID NO 18
<211> LENGTH: 20
<212> TYPE: DNA
<213> ORGANISM: Homo sapiens

<400> SEQUENCE: 18
cctggcgtcg tgattagtga                                          20

<210> SEQ ID NO 19
<211> LENGTH: 24
<212> TYPE: DNA
<213> ORGANISM: Homo sapiens

<400> SEQUENCE: 19
cccgaggtcc atctactgta actt                                     24

<210> SEQ ID NO 20
<211> LENGTH: 25
<212> TYPE: DNA
<213> ORGANISM: Homo sapiens

<400> SEQUENCE: 20
agtagcaagg ttcaacgatc tgaga                                    25

<210> SEQ ID NO 21
<211> LENGTH: 24
<212> TYPE: DNA
<213> ORGANISM: Homo sapiens

<400> SEQUENCE: 21
ctaccaccac tgcatcaaat tcat                                     24

<210> SEQ ID NO 22
<211> LENGTH: 21
<212> TYPE: DNA
<213> ORGANISM: Homo sapiens

<400> SEQUENCE: 22
ggaacaagag ggcatctgct a                                        21

<210> SEQ ID NO 23
<211> LENGTH: 26
<212> TYPE: DNA
<213> ORGANISM: Homo sapiens

<400> SEQUENCE: 23
ggagctgtga tgtgaagttt cctata                                   26

<210> SEQ ID NO 24
<211> LENGTH: 28
<212> TYPE: DNA
<213> ORGANISM: Homo sapiens

<400> SEQUENCE: 24
ccagaaacaa aaataaggag aacaattc                                 28

<210> SEQ ID NO 25
<211> LENGTH: 18
<212> TYPE: DNA
<213> ORGANISM: Homo sapiens

<400> SEQUENCE: 25
gctagtggcg ggcatgat                                            18
```

<210> SEQ ID NO 26
<211> LENGTH: 19
<212> TYPE: DNA
<213> ORGANISM: Homo sapiens

<400> SEQUENCE: 26
gtgacccgac cccaatctc                                                19

<210> SEQ ID NO 27
<211> LENGTH: 20
<212> TYPE: DNA
<213> ORGANISM: Homo sapiens

<400> SEQUENCE: 27
ttgatcccca atgcttcaca                                               20

<210> SEQ ID NO 28
<211> LENGTH: 18
<212> TYPE: DNA
<213> ORGANISM: Homo sapiens

<400> SEQUENCE: 28
cggcaacctc agccaagt                                                 18

<210> SEQ ID NO 29
<211> LENGTH: 24
<212> TYPE: DNA
<213> ORGANISM: Mus Musculus

<400> SEQUENCE: 29
ccctagatga cacatgagca aaag                                          24

<210> SEQ ID NO 30
<211> LENGTH: 21
<212> TYPE: DNA
<213> ORGANISM: Mus Musculus

<400> SEQUENCE: 30
agcgtcgtgg tattcctgaa a                                             21

<210> SEQ ID NO 31
<211> LENGTH: 19
<212> TYPE: DNA
<213> ORGANISM: Mus Musculus

<400> SEQUENCE: 31
cagcggtggc agaatgttg                                                19

<210> SEQ ID NO 32
<211> LENGTH: 24
<212> TYPE: DNA
<213> ORGANISM: Mus Musculus

<400> SEQUENCE: 32
acaccgaagt agaaatggct ctct                                          24

<210> SEQ ID NO 33
<211> LENGTH: 26
<212> TYPE: DNA
<213> ORGANISM: Mus Musculus

<400> SEQUENCE: 33

-continued ccctcgtcta tcagtcttgt ctgtat                                    26

<210> SEQ ID NO 34
<211> LENGTH: 23
<212> TYPE: DNA
<213> ORGANISM: Mus Musculus

<400> SEQUENCE: 34
atttgggtag ctgttctgtg gaa                                       23

<210> SEQ ID NO 35
<211> LENGTH: 21
<212> TYPE: DNA
<213> ORGANISM: Mus Musculus

<400> SEQUENCE: 35
acggccaggt catcactatt g                                         21

<210> SEQ ID NO 36
<211> LENGTH: 23
<212> TYPE: DNA
<213> ORGANISM: Mus Musculus

<400> SEQUENCE: 36
cacaggattc catacccaag aag                                       23

<210> SEQ ID NO 37
<211> LENGTH: 21
<212> TYPE: DNA
<213> ORGANISM: Sus scrofa

<400> SEQUENCE: 37
agaccgcaac ctgaacacaa c                                         21

<210> SEQ ID NO 38
<211> LENGTH: 22
<212> TYPE: DNA
<213> ORGANISM: Sus scrofa

<400> SEQUENCE: 38
gggtgtccga aaaatcagaa ca                                        22

<210> SEQ ID NO 39
<211> LENGTH: 19
<212> TYPE: DNA
<213> ORGANISM: Sus scrofa

<400> SEQUENCE: 39
tggccaagca gaccaagag                                            19

<210> SEQ ID NO 40
<211> LENGTH: 18
<212> TYPE: DNA
<213> ORGANISM: Sus scrofa

<400> SEQUENCE: 40
tcccacttgg ccgagaag                                             18

<210> SEQ ID NO 41
<211> LENGTH: 20
<212> TYPE: DNA
<213> ORGANISM: Sus scrofa

<400> SEQUENCE: 41

```
gctgagctgt ggagggaact                                                   20

<210> SEQ ID NO 42
<211> LENGTH: 30
<212> TYPE: DNA
<213> ORGANISM: Sus scrofa

<400> SEQUENCE: 42
ttgaattctg tttacctctt ctttgtacac                                        30

<210> SEQ ID NO 43
<211> LENGTH: 22
<212> TYPE: DNA
<213> ORGANISM: Sus scrofa

<400> SEQUENCE: 43
ggacctgacc gactacctca tg                                                22

<210> SEQ ID NO 44
<211> LENGTH: 22
<212> TYPE: DNA
<213> ORGANISM: Sus scrofa

<400> SEQUENCE: 44
cgacgtagca gagcttctcc tt                                                22
```